US008822145B2

(12) United States Patent
Ryan

(10) Patent No.: US 8,822,145 B2
(45) Date of Patent: *Sep. 2, 2014

(54) IDENTIFICATION OF POLD2 SEQUENCES

(71) Applicant: Ryogen LLC, Suffern, NY (US)

(72) Inventor: James Ryan, Augusta, GA (US)

(73) Assignee: Ryogen LLC, Suffern, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/680,223

(22) Filed: Nov. 19, 2012

(65) Prior Publication Data

US 2013/0130252 A1    May 23, 2013

Related U.S. Application Data

(60) Division of application No. 12/533,164, filed on Jul. 31, 2009, now Pat. No. 8,313,900, which is a division of application No. 10/642,946, filed on Aug. 18, 2003, now Pat. No. 7,588,915, which is a continuation of application No. 09/957,956, filed on Sep. 21, 2001, now abandoned.

(60) Provisional application No. 60/234,422, filed on Sep. 21, 2000.

(51) Int. Cl.
| | |
|---|---|
| C07H 21/00 | (2006.01) |
| C07H 21/02 | (2006.01) |
| C07H 21/04 | (2006.01) |
| C12Q 1/68 | (2006.01) |
| C12P 21/06 | (2006.01) |

(52) U.S. Cl.
USPC .......... 435/6; 435/69.1; 435/91.1; 435/91.31; 435/455; 536/23.1; 536/23.2; 536/23.5; 536/24.31

(58) Field of Classification Search
USPC ........ 435/6, 91.1, 69.1, 91.31, 455; 536/23.1, 536/23.2, 23.5, 24.31
See application file for complete search history.

(56) References Cited

U.S. PATENT DOCUMENTS

| | | | |
|---|---|---|---|
| 5,541,060 A | 7/1996 | Bell | |
| 5,624,803 A | 4/1997 | Noonberg | |
| 5,972,334 A | 10/1999 | Denney | |
| 6,783,961 B1 | 8/2004 | Edwards | |
| 6,812,339 B1 | 11/2004 | Venter | |
| 8,313,900 B2 * | 11/2012 | Ryan | 435/455 |
| 2002/0048763 A1 | 4/2002 | Penn | |
| 2003/0077808 A1 | 4/2003 | Rosen | |
| 2003/0204075 A9 | 10/2003 | Wang | |
| 2007/0015162 A1 | 1/2007 | Rosen | |
| 2007/0031842 A1 | 2/2007 | Rosen | |

FOREIGN PATENT DOCUMENTS

| | | |
|---|---|---|
| WO | 9520678 | 8/1995 |
| WO | 0058467 | 10/2000 |

OTHER PUBLICATIONS

Sulston et al., Genome Research, vol. 8, No. 11, pp. 1097-1108 (1998).*
U.S. Appl. No. 13/680,178, Non-Final Office Action May 31, 2013.
U.S. Appl. No. 13/680,203, Non-Final Office Action May 30, 2013.
U.S. Appl. No. 09/957,956, Non-Final Office Action Dec. 4, 2002.
U.S. Appl. No. 09/957,956 Non-Final Office Action May 21, 2003.
U.S. Appl. No. 10/642,946 Non-Final Office Action Oct. 17, 2006.
U.S. Appl. No. 10/642,946 Non-Final Office Action Oct. 26, 2007.
U.S. Appl. No. 10/642,946 Non-Final Office Action Mar. 25, 2008.
U.S. Appl. No. 10/642,946 Non-Final Office Action Oct. 16, 2008.
U.S. Appl. No. 10/642,946 Notice of Allowance Apr. 28, 2009.
U.S. Appl. No. 12/533,105 Non-Final Office Action May 21, 2010.
U.S. Appl. No. 12/533,105 Final Office Action Nov. 29, 2010.
U.S. Appl. No. 12/533,105 Non-Final Office Action Mar. 5, 2012.
U.S. Appl. No. 12/533,105 Notice of Allowance Jul. 16, 2012.
U.S. Appl. No. 12/533,130 Non-Final Office Action May 20, May 20, 2010.
U.S. Appl. No. 12/533,130 Final Office Action Nov. 29, 2010.
U.S. Appl. No. 12/533,130 Non-Final Office Action Mar. 29, 2012.
U.S. Appl. No. 12/533,130 Notice of Allowance Jul. 24, 2012.
U.S. Appl. No. 12/533,164 Non-Final Office Action Jun. 15, 2010.
U.S. Appl. No. 12/533,164 Final Office Action Dec. 29, 2010.
U.S. Appl. No. 12/533,164 Non-Final Office Action Mar. 2, 2012.
U.S. Appl. No. 12/533,164 Notice of Allowance Jul. 11, 2012.
U.S. Appl. No. 12/533,087 Non-Final Office Action Apr. 6, 2011.
U.S. Appl. No. 12/533,087 Final Office Action Oct. 4, 2011.
U.S. Appl. No. 12/533,087 Notice of Allowance Jan. 12, 2012.
U.S. Appl. No. 60/231,498, filed Sep. 8, 2000, Venter. (Priority for US Patent 6812339).
Table 1 of U.S. Appl. No. 60/231,498, Sep. 8, 2000.
Table 2 of U.S. Appl. No. 60/231,498, Sep. 8, 2000.
Table 3 of U.S. Appl. No. 60/231,498, Sep. 8, 2000
Table 4 of U.S. Appl. No. 60/231,498, Sep. 8, 2000.
Table 5 of U.S. Appl. No. 60/231,498, Sep. 8, 2000.
Table 6 of U.S. Appl. No. 60/231,498, Sep. 8, 2000.
Table 7 of U.S. Appl. No. 60/231,498, Sep. 8, 2000.
Table 8 of U.S. Appl. No. 60/231,498, Sep. 8, 2000.
Table 9 of U.S. Appl. No. 60/231,498, Sep. 8, 2000.
Table 10 of U.S. Appl. No. 60/231,498, Sep. 8, 2000.
Table 11 of U.S. Appl. No. 60/231,498, Sep. 8, 2000.
Table 12 of U.S. Appl. No. 60/231,498, Sep. 8, 2000.
Table 13 of U.S. Appl. No. 60/231,498, Sep. 8, 2000.
Table 14 of U.S. Appl. No. 60/231,498, Sep. 8, 2000.
Table 15 of U.S. Appl. No. 60/231,498, Sep. 8, 2000.
Table 16 of U.S. Appl. No. 60/231,498, Sep. 8, 2000.
Table 17 of U.S. Appl. No. 60/231,498, Sep. 8, 2000.

(Continued)

*Primary Examiner* — Jane Zara
(74) *Attorney, Agent, or Firm* — Cheryl H. Agris; Agris & Von Natzmer, LLP

(57) ABSTRACT

Provided are isolated genomic polynucleotide fragments that encode human SNARE YKT6, human glucokinase, human adipocyte enhancer binding protein (AEBP1) and DNA directed 50 kD regulatory subunit (POLD2), vectors and hosts containing these fragments and fragments hybridizing to noncoding regions as well as antisense oligonucleotides to these fragments. The invention is further directed to methods of using these fragments to obtain SNARE YKT6, human glucokinase, AEBP1 protein and POLD2 and to diagnose, treat, prevent and/or ameliorate a pathological disorder.

2 Claims, No Drawings

(56) References Cited

OTHER PUBLICATIONS

Table 18 of U.S. Appl. No. 60/231,498, Sep. 8, 2000.
Table 19 of U.S. Appl. No. 60/231,498, Sep. 8, 2000.
Table 20 of U.S. Appl. No. 60/231,498, Sep. 8, 2000.
Table 21 of U.S. Appl. No. 60/231,498, Sep. 8, 2000.
Table 22 of U.S. Appl. No. 60/231,498, Sep. 8, 2000.
Table 23 of U.S. Appl. No. 60/231,498, Sep. 8, 2000.
Table 24 of U.S. Appl. No. 60/231,498.
Table 25 of U.S. Appl. No. 60/231,498.
EMBL database Accession No. Q9UESO May 1, 2000 SNARE protein Ykt6 (Fragment) *Homo sapiens*.
Table 24 of U.S. Appl. No. 60/231,498, Sep. 8, 2000.
Table 25 of U.S. Appl. No. 60/231,498, Sep. 8, 2000.
Ahmed, Proc. Natl. Acad. Sci. 96: 14795-14800. 1999.
Altschul, Nucleic Acids Res. 25: 3389-3402. 1997.
Burge, J. Mol. Biol. 268: 78-94. 1997.
International Search Report for PCT/2001/29454, filed Mar. 27, 2003.
Layne, J. Biol. Chem. 273:15654-15660. 1998.
Maestrini, Hum. Mol. Gen. 2: 761-766. 1993.
McNew, J. Biol. Chem. 272: 17776-17783. 1997.
Muise, Biochem J. 343: 341-345. 1999.
Nuttal, Bone 27: 177-184. 2000.
Ohno, Biochem Biophys Res Comm 228: 411-414. 1996.
Perez "Characterization of the 5'-flanking region of the gene encoding the 50 kDa subunit of human DNA polymerase δ" Biochem Biophys Acta 1493: 231-236. 2000.
Skidgel, TIPS 9: 299-304. 1988.
Stoffel, Proc. Natl. Acad. Sci. 89:2698-7702, 1992.
Sulston, Genome Res 8:1097-1108. 1998.
Tanizawa, Mol. Endocrinol. 6: 1070-1081. 1992.
Waterston, R.H. GenBank Accession No. AC0006454.4 (gi: 28261662) Submitted Jan. 28, 1999, bases 1-153203.
Waterston, R.H. GenBank Accession No. AC0006456.3 (gi: 21322189) Submitted Jan. 28, 1999, bases 1-75609.
Waterston, R.H. GenBank Accession No. AC0006454.2 (gi:4337283) Submitted Jan. 28, 1999, bases 1-151965.
Zhang, Genomics 29: 179-186. 1995.

* cited by examiner

IDENTIFICATION OF POLD2 SEQUENCES

PRIORITY CLAIM

This application is a divisional of application Ser. No. 12/533,105, filed Jul. 31, 2009, which is a divisional of Ser. No. 10/642,946, filed Aug. 18, 2003, now U.S. Pat. No. 7,588,915, issued Sep. 15, 2009, which is a continuation of application Ser. No. 09/957,956, filed Sep. 21, 2001, now abandoned, the contents of which all are incorporated herein by reference. Application Ser. No. 09/957,956 is a non-provisional application of and claims priority under 35 U.S.C. §119(e) to provisional application Ser. No. 60/234,422, filed Sep. 21, 2000, also incorporated herein by reference.

FIELD OF THE INVENTION

The invention is directed to isolated genomic polynucleotide fragments that encode human SNARE YKT6, human glucokinase, human adipocyte enhancer binding protein 1 (AEBP1) and DNA directed 50 kD regulatory subunit (POLD2), vectors and hosts containing these fragments and fragments hybridizing to noncoding regions as well as antisense oligonucleotides to these fragments. The invention is further directed to methods of using these fragments to obtain SNARE YKT6, human glucokinase, AEBP1 protein and POLD2 and to diagnose, treat, prevent and/or ameliorate a pathological disorder.

BACKGROUND OF THE INVENTION

Chromosome 7 contains genes encoding, for example, epidermal growth factor receptor, collagen-1-Alpha-1-chain, SNARE YKT6, human glucokinase, human adipocyte enhancer binding protein 1 and DNA polymerase delta small subunit (POLD2). SNARE YKT6, human glucokinase, human adipocyte enhancer binding protein 1 and DNA polymerase delta small subunit (POLD2) are discussed in further detail below.
SNARE YKT6
SNARE YKT6, a substrate for prenylation, is essential for vesicle-associated endoplasmic reticulum-Golgi transport (McNew, J. A. et al. J. Biol. Chem. 272, 17776-17783, 1997). It has been found that depletion of this function stops cell growth and manifests a transport block at the endoplasmic reticulum level.
Human Glucokinase
Human glucokinase (ATP:D-hexose 6-phosphotransferase) is thought to play a major role in glucose sensing in pancreatic islet beta cells (Tanizawa et al., 1992, Mol. Endocrinol. 6:1070-1081) and in the liver. Glucokinase defects have been observed in patients with noninsulin-dependent diabetes mellitus (NIDDM) patients. Mutations in the human glucokinase gene are thought to play a role in the early onset of NIDDM. The gene has been shown by Southern Blotting to exist as a single copy on chromosome 7. It was further found to contain 10 exons including one exon expressed in islet beta cells and the other expressed in liver.
Human Adipocyte Enhancer Binding Protein 1
The adipocyte-enhancer binding protein 1 (AEBP1) is a transcriptional repressor having carboxypeptidase B-like activity which binds to a regulatory sequence (adipocyte enhancer 1, AE-1) located in the proximal promoter region of the adipose P2 (aP2) gene, which encodes the adipocyte fatty acid binding protein (Muise et al., 1999, Biochem. J. 343: 341-345). B-like carboxypeptidases remove C-terminal arginine and lysine residues and participate in the release of active peptides, such as insulin, alter receptor specificity for polypeptides and terminate polypeptide activity (Skidgel, 1988, Trends Pharmacol. Sci. 9:299-304). For example, they are thought to be involved in the onset of obesity (Naggert et al., 1995, Nat. Genet. 10:1335-1342). It has been reported that obese and hyperglycemic mice homozygous for the fat mutation contain a mutation in the CP-E gene.

Full length cDNA clones encoding AEBP1 have been isolated from human osteoblast and adipose tissue (Ohno et al., 1996, Biochem. Biophys Res. Commun. 228:411-414). Two forms have been found to exist due to alternative splicing. This gene appears to play a significant role in regulating adipogenesis. In addition to playing a role in obesity, adipogenesis may play a role in ostopenic disorders. It has been postulated that adipogenesis inhibitors may be used to treat osteopenic disorders (Nuttal et al., 2000, Bone 27:177-184).
DNA Polymerase Delta Small Subunit (POLD2)

DNA polymerase delta core is a heterodimeric enzyme with a catalytic subunit of 125 kD and a second subunit of 50 kD and is an essential enzyme for DNA replication and DNA repair (Zhang et al., 1995, Genomics 29:179-186). cDNAs encoding the small subunit have been cloned and sequenced. The gene for the small subunit has been localized to human chromosome 7 via PCR analysis of a panel of human-hamster hybrid cell lines. However, the genomic DNA has not been isolated and the exact location on chromosome 7 has not been determined.

OBJECTS OF THE INVENTION

Although cDNAs encoding the above-disclosed proteins have been isolated, their location on chromosome 7 has not been determined. Furthermore, genomic DNA encoding these polypeptides have not been isolated. Noncoding sequences can play a significant role in regulating the expression of polypeptides as well as the processing of RNA encoding these polypeptides.

There is clearly a need for obtaining genomic polynucleotide sequences encoding these polypeptides. Therefore, it is an object of the invention to isolate such genomic polynucleotide sequences.

SUMMARY OF THE INVENTION

The invention is directed to an isolated genomic polynucleotide, said polynucleotide obtainable from human chromosome 7 having a nucleotide sequence at least 95% identical to a sequence selected from the group consisting of:

(a) a polynucleotide encoding a polypeptide selected from the group consisting of human SNARE YKT6 depicted in SEQ ID NO:1, human glucokinase depicted in SEQ ID NO:2, human adipocyte enhancer binding protein 1 (AEBP1) depicted in SEQ ID NO:3 and DNA directed 50 kD regulatory subunit (POLD2) depicted in SEQ ID NO:4;

(b) a polynucleotide selected from the group consisting of SEQ ID NO:5 which encodes human SNARE YKT6 depicted in SEQ ID NO:1, SEQ ID NO:6 which encodes human glucokinase depicted in SEQ ID NO:2, SEQ ID NO:8 which encodes human adipocyte enhancer binding protein 1 depicted in SEQ ID NO:3 and SEQ ID NO: 7 which encodes DNA directed 50 kD regulatory subunit (POLD2) depicted in SEQ ID NO:4;

(c) a polynucleotide which is a variant of SEQ ID NOS:5, 6, 7, or 8;

(d) a polynucleotide which is an allelic variant of SEQ ID NOS:5, 6, 7, or 8;

(e) a polynucleotide which encodes a variant of SEQ ID NOS:1, 2, 3, or 4;

(f) a polynucleotide which hybridizes to any one of the polynucleotides specified in (a)-(e);

(g) a polynucleotide that is a reverse complement to the polynucleotides specified in (a)-(f) and (h) containing at least 10 transcription factor binding sites selected from the group consisting of AP1FJ-Q2, AP1-C, AP1-Q2, AP1-Q4, AP4-Q5, AP4-Q6, ARNT-01, CEBP-01, CETS1P54-01, CREL-01, DELTAEF1-01, FREAC7-01, GATA1-02, GATA1-03, GATA1-04, GATA1-06, GATA2-02, GATA3-02, GATA-C, GC-01, GFII-01, HFH2-01, HFH3-01, HFH8-01, IK2-01, LMO2COM-01, LMO2COM-02, LYF1-01, MAX-01, NKX25-01, NMYC-01, S8-01, SOX5-01, SP1-Q6, SAEBP1-01, SRV-02, STAT-01, TATA-01, TCF11-01, USF-01, USF-C and USF-Q6 as well as nucleic acid constructs, expression vectors and host cells containing these polynucleotide sequences.

The polynucleotides of the present invention may be used for the manufacture of a gene therapy for the prevention, treatment or amelioration of a medical condition by adding an amount of a composition comprising said polynucleotide effective to prevent, treat or ameliorate said medical condition.

The invention is further directed to obtaining these polypeptides by (a) culturing host cells comprising these sequences under conditions that provide for the expression of said polypeptide and (b) recovering said expressed polypeptide.

The polypeptides obtained may be used to produce antibodies by (a) optionally conjugating said polypeptide to a carrier protein;

(b) immunizing a host animal with said polypeptide or peptide-carrier protein conjugate of step (b) with an adjuvant and (c) obtaining antibody from said immunized host animal.

The invention is further directed to polynucleotides that hybridize to noncoding regions of said polynucleotide sequences as well as antisense oligonucleotides to these polynucleotides as well as antisense mimetics. The antisense oligonucleotides or mimetics may be used for the manufacture of a medicament for prevention, treatment or amelioration of a medical condition.

The invention is further directed to kits comprising these polynucleotides and kits comprising these antisense oligonucleotides or mimetics.

In a specific embodiment, the noncoding regions are transcription regulatory regions. The transcription regulatory regions may be used to produce a heterologous peptide by expressing in a host cell, said transcription regulatory region operably linked to a polynucleotide encoding the heterologous polypeptide and recovering the expressed heterologous polypeptide.

The polynucleotides of the present invention may be used to diagnose a pathological condition in a subject comprising (a) determining the presence or absence of a mutation in the polynucleotides of the present invention and (b) diagnosing a pathological condition or a susceptibility to a pathological condition based on the presence or absence of said mutation.

DETAILED DESCRIPTION OF THE INVENTION

The invention is directed to isolated genomic polynucleotide fragments that encode human SNARE YKT6, human glucokinase, human adipocyte enhancer binding protein 1 and DNA directed 50 kD regulatory subunit (POLD2), which in a specific embodiment are the SNARE YKT6, human glucokinase, human adipocyte enhancer binding protein 1 and DNA directed 50 kD regulatory subunit (POLD2) genes, as well as vectors and hosts containing these fragments and polynucleotide fragments hybridizing to noncoding regions, as well as antisense oligonucleotides to these fragments.

As defined herein, a "gene" is the segment of DNA involved in producing a polypeptide chain; it includes regions preceding and following the coding region, as well as intervening sequences (introns) between individual coding segments (exons).

As defined herein "isolated" refers to material removed from its original environment and is thus altered "by the hand of man" from its natural state. An isolated polynucleotide can be part of a vector, a composition of matter or could be contained within a cell as long as the cell is not the original environment of the polynucleotide.

The polynucleotides of the present invention may be in the form of RNA or in the form of DNA, which DNA includes genomic DNA and synthetic DNA. The DNA may be double-stranded or single-stranded and if single stranded may be the coding strand or non-coding strand.

The human SNARE YKT6 polypeptide has the amino acid sequence depicted in SEQ ID NO:1 and is encoded by the genomic DNA sequence shown in SEQ ID NO:5. The genomic DNA for SNARE YKT6 gene is 39,000 base pairs in length and contains seven exons (see Table 4 below for location of exons). As will be discussed in further detail below, the SNARE YKT6 gene is situated in genomic clone AC006454 at nucleotides 36,001-75,000.

The human glucokinase is depicted in SEQ ID NO:2 and is encoded by the genomic DNA sequence shown in SEQ ID NO:6. The human glucokinase genomic DNA is 46,000 base pairs in length and contains ten exons (see Table 3 below for location of exons).

The human adipocyte enhancer binding protein 1 has the amino acid sequence depicted in SEQ ID NO:3 and is encoded by the genomic DNA sequence shown in SEQ ID NO:8. The adipocyte enhancer binding protein 1 is 16,000 base pairs in length and contains 21 exons (see Table 2 below for location of exons). As will be discussed in further detail below, the human AEBP1 gene is situated in genomic clone AC006454 at nucleotides 137,041-end.

POLD2 has an amino acid sequence depicted in SEQ ID NO:4 and a genomic DNA sequence depicted in SEQ ID NO: 7. The POLD2 gene is 19,000 base pairs in length and contains ten exons (see Table 1 below for location of exons). As will be discussed in further detail below, the POLD2 gene is situated in genomic clone AC006454 at nucleotides 119,001-138,000.

The polynucleotides of the invention have at least a 95% identity and may have a 96%, 97%, 98% or 99% identity to the polynucleotides depicted in SEQ ID NOS:5, 6, 7 or 8 as well as the polynucleotides in reverse sense orientation, or the polynucleotide sequences encoding the SNARE YKT6, human glucokinase, AEBP1, or POLD2 polypeptides depicted in SEQ ID NOS:1, 2, 3, or 4 respectively.

A polynucleotide having 95% "identity" to a reference nucleotide sequence of the present invention, is identical to the reference sequence except that the polynucleotide sequence may include on average up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence, the ORF (open reading frame), or any fragment specified as described herein.

As a practical matter, whether any particular nucleic acid molecule or polypeptide is at least 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237-245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identify, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence are calculated for the purposes of manually adjusting the percent identity score.

For example, a 95 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 5% of the sequence (number of bases at the 5' and 3' ends not matched/total numbers of bases in the query sequence) so 5% is subtracted from the percent identity score calculated by the FASTDB program. If the remaining 95 bases were perfectly matched the final percent identity would be 95%. In another example, a 95 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for purposes of the present invention.

A polypeptide that has an amino acid sequence at least, for example, 95% "identical" to a query amino acid sequence is identical to the query sequence except that the subject polypeptide sequence may include on average, up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the referenced sequence or in one or more contiguous groups within the reference sequence.

A preferred method for determining the best overall match between a query sequence (a sequence of the present invention) and a subject sequence, also referred to as a global sequence alignment, can be determined using the FASTDB computer program based on the algorithm of Brutlag et al. (Com. App. Biosci. (1990) 6:237-245). In a sequence alignment, the query and subject sequence are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

The invention also encompasses polynucleotides that hybridize to the polynucleotides depicted in SEQ ID NOS: 5, 6, 7 or 8. A polynucleotide "hybridizes" to another polynucleotide, when a single-stranded form of the polynucleotide can anneal to the other polynucleotide under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a temperature of 42° C., can be used, e.g., 5×SSC, 0.1% SDS, 0.25% milk, and no formamide; or 40% formamide, 5×SSC, 0.5% SDS). Moderate stringency hybridization conditions correspond to a higher temperature of 55° C., e.g., 40% formamide, with 5× or 6×SCC. High stringency hybridization conditions correspond to the highest temperature of 65° C., e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA.

Polynucleotide and Polypeptide Variants

The invention is directed to both polynucleotide and polypeptide variants. A "variant" refers to a polynucleotide or polypeptide differing from the polynucleotide or polypeptide of the present invention, but retaining essential properties thereof. Generally, variants are overall closely similar and in many regions, identical to the polynucleotide or polypeptide of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred.

The invention also encompasses allelic variants of said polynucleotides. An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The amino acid sequences of the variant polypeptides may differ from the amino acid sequences depicted in SEQ ID NOS:1, 2, 3 or 4 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain. Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, as well as these in reverse.

Noncoding Regions

The invention is further directed to polynucleotide fragments containing or hybridizing to noncoding regions of the SNARE YKT6, AEBP1, human glucokinase and POLD2 genes. These include but are not limited to an intron, a 5' non-coding region, a 3' non-coding region and splice junctions (see Tables 1-4), as well as transcription factor binding sites (see Table 5). The polynucleotide fragments may be a short polynucleotide fragment which is between about 8 nucleotides to about 40 nucleotides in length. Such shorter fragments may be useful for diagnostic purposes. Such short polynucleotide fragments are also preferred with respect to polynucleotides containing or hybridizing to polynucleotides containing splice junctions. Alternatively larger fragments, e.g., of about 50, 150, 500, 600 or about 2000 nucleotides in length may be used.

TABLE 1

Exon/Intron Regions of Polymerase, DNA directed, 50 kD regulatory subunit (POLD2) Genomic DNA

| EXONS | LOCATION (nucleotide no.) (Amino acid no.) | | |
|---|---|---|---|
| 1. | 11546 | --- | 11764 |
|    | 1     |     | 73    |
| 2. | 15534 | --- | 15656 |
|    | 74    |     | 114   |
| 3. | 15857 | --- | 15979 |
|    | 115   |     | 155   |
| 4. | 16351 | --- | 16464 |
|    | 156   |     | 193   |
| 5. | 16582 | --- | 16782 |
|    | 194   |     | 260   |
| 6. | 17089 | --- | 17169 |
|    | 261   |     | 287   |
| 7. | 17327 | --- | 17484 |
|    | 288   |     | 339   |
| 8. | 17704 | --- | 17829 |
|    | 340   |     | 381   |
| 9. | 18199 | --- | 18303 |
|    | 382   |     | 416   |
| 10.| 18653 | --- | 18811 |
|    | 417   |     | 469   |

'tga' at 18812-14
Poly A at 18885-90

TABLE 2

AEBP1 (adipocyte enhancer binding protein 1), vascular smooth muscle-type. Reverse strand coding.

| EXONS | LOCATION (nucleotide no.) (Amino acid no.) | | |
|---|---|---|---|
| 21. | 1301 | --- | 1966 |
|     | 1158 |     | 937  |
| 20. | 2209 | --- | 2304 |
|     | 936  |     | 905  |
| 19. | 2426 | --- | 2569 |
|     | 904  |     | 857  |
| 18. | 2651 | --- | 3001 |
|     | 856  |     | 740  |
| 17. | 3238 | --- | 3417 |
|     | 739  |     | 680  |
| 16. | 3509 | --- | 3706 |
|     | 679  |     | 614  |
| 15. | 3930 | --- | 4052 |
|     | 613  |     | 573  |
| 14. | 4320 | --- | 4406 |
|     | 572  |     | 544  |

TABLE 2-continued

AEBP1 (adipocyte enhancer binding protein 1),
vascular smooth muscle-type. Reverse strand coding.

| EXONS | LOCATION (nucleotide no.) (Amino acid no.) | | |
|---|---|---|---|
| 13. | 4503 | --- | 4646 |
|  | 543 |  | 496 |
| 12. | 4750 | --- | 4833 |
|  | 495 |  | 468 |
| 11. | 5212 | --- | 5352 |
|  | 467 |  | 421 |
| 10. | 5435 | --- | 5545 |
|  | 420 |  | 384 |
| 9. | 6219 | --- | 6272 |
|  | 383 |  | 366 |
| 8. | 6376 | --- | 6453 |
|  | 365 |  | 340 |
| 7. | 6584 | --- | 6661 |
|  | 339 |  | 314 |
| 6. | 7476 | --- | 7553 |
|  | 313 |  | 288 |
| 5. | 7629 | --- | 7753 |
|  | 287 |  | 247 |
| 4. | 7860 | --- | 7931 |
|  | 246 |  | 223 |
| 3. | 8050 | --- | 8121 |
|  | 222 |  | 199 |
| 2. | 8673 | --- | 9014 |
|  | 198 |  | 85 |
| 1. | 10642 | --- | 10893 |
|  | 84 |  | 1 |

Stop codon 1298-1300
Poly A-site 1013-18

TABLE 3

Glucokinase

| EXONS | LOCATION (nucleotide no.) (Amino acid no.) | | |
|---|---|---|---|
| 1. | 20485 | --- | 20523 |
|  | 1 |  | 13 |
| 2. | 25133 | --- | 25297 |
|  | 14 |  | 68 |
| 3. | 26173 | --- | 26328 |
|  | 69 |  | 120 |
| 4. | 27524 | --- | 27643 |
|  | 121 |  | 160 |
| 5. | 28535 | --- | 28630 |
|  | 161 |  | 192 |
| 6. | 28740 | --- | 28838 |
|  | 193 |  | 225 |
| 7. | 30765 | --- | 30950 |
|  | 226 |  | 287 |
| 8. | 31982 | --- | 32134 |
|  | 288 |  | 338 |
| 9. | 32867 | --- | 33097 |
|  | 339 |  | 415 |
| 10. | 33314 | --- | 33460 |
|  | 416 |  | 464 |

Stop codon 33461-3

TABLE 4

SNARE YKT6. Reverse strand coding.

| EXONS | LOCATION (nucleotide no.) (Amino acid no.) | | |
|---|---|---|---|
| 7. | 4320 | --- | 4352 |
|  | 198 |  | 188 |
| 6. | 5475 | --- | 5576 |
|  | 187 |  | 154 |

TABLE 4-continued

SNARE YKT6. Reverse strand coding.

| EXONS | LOCATION (nucleotide no.) (Amino acid no.) | | |
|---|---|---|---|
| 5. | 8401 | --- | 8466 |
|  | 153 |  | 132 |
| 4. | 9107 | --- | 9211 |
|  | 131 |  | 97 |
| 3. | 10114 | --- | 10215 |
|  | 96 |  | 63 |
| 2. | 11950 | --- | 12033 |
|  | 62 |  | 35 |
| 1. | 15362 | --- | 15463 |
|  | 34 |  | 1 |

Stop codon at 4817-19
Poly A-site: 4245-4250

TABLE 5

TRANSCRIPTION FACTOR BINDING SITES

| BINDING SITES | SNARE YKT6 | GLUCOKINASE | POLD2 | AEBP1 |
|---|---|---|---|---|
| AP1FJ-Q2 | 11 |  |  | 11 |
| AP1-C | 15 | 15 | 7 | 6 |
| AP1-Q2 | 9 |  |  | 5 |
| AP1-Q4 | 7 |  |  | 4 |
| AP4-Q5 | 36 |  | 5 | 43 |
| AP4-Q6 | 17 |  |  | 23 |
| ARNT-01 | 7 |  |  | 5 |
| CEBP-01 | 7 |  |  |  |
| CETS1P54-01 | 6 |  |  |  |
| CREL-01 | 7 |  |  |  |
| DELTAEF1-01 | 64 | 12 | 5 | 50 |
| FREAC7-01 |  | 4 |  |  |
| GATA1-02 | 19 |  |  |  |
| GATA1-03 | 12 |  |  | 6 |
| GATA1-04 | 25 | 6 |  |  |
| GATA1-06 | 8 | 5 |  |  |
| GATA2-02 | 10 |  |  |  |
| GATA3-02 | 5 |  |  |  |
| GATA-C | 11 | 6 |  |  |
| GC-01 |  |  |  | 4 |
| GFII-01 | 6 |  |  |  |
| HFH2-01 | 5 |  |  |  |
| HFH3-01 | 10 |  |  |  |
| HFH8-01 | 4 |  |  |  |
| IK2-01 | 49 |  |  | 29 |
| LMO2COM-01 | 41 | 6 |  | 27 |
| LMO2COM-02 | 31 | 5 |  | 7 |
| LYF1-01 | 10 | 13 | 6 |  |
| MAX-01 | 4 |  |  |  |
| MYOD-01 | 7 |  |  |  |
| MYOD-Q6 | 32 | 19 | 7 | 12 |
| MZF1-01 | 99 | 40 | 15 | 94 |
| NF1-Q6 | 5 |  |  | 7 |
| NFAT-Q6 | 43 | 8 | 7 | 8 |
| NFKAPPAB50-01 |  | 4 |  |  |
| NKX25-01 | 13 | 14 | 5 |  |
| NMYC-01 | 12 |  |  | 8 |
| S8-01 |  | 30 | 4 |  |
| SOX5-01 | 21 | 20 | 4 | 4 |
| SP1-Q6 |  |  |  | 8 |
| SAEBP1-01 | 4 |  |  |  |
| SRV-02 | 5 |  |  |  |
| STAT-01 | 6 |  |  |  |
| TATA-01 | 8 |  |  |  |
| TCF11-01 | 47 | 28 | 5 | 19 |
| USF-01 | 12 | 8 | 6 | 8 |
| USF-C | 16 | 12 | 12 | 8 |
| USF-Q6 | 6 |  |  |  |

In a specific embodiment, such noncoding sequences are expression control sequences. These include but are not limited to DNA regulatory sequences, such as promoters, enhancers, repressors, terminators, and the like, that provide for the regulation of expression of a coding sequence in a host cell. In eukaryotic cells, polyadenylation signals are also control sequences.

In a more specific embodiment of the invention, the expression control sequences may be operatively linked to a polynucleotide encoding a heterologous polypeptide. Such expression control sequences may be about 50-200 nucleotides in length and specifically about 50, 100, 200, 500, 600, 1000 or 2000 nucleotides in length. A transcriptional control sequence is "operatively linked" to a polynucleotide encoding a heterologous polypeptide sequence when the expression control sequence controls and regulates the transcription and translation of that polynucleotide sequence. The term "operatively linked" includes having an appropriate start signal (e.g., ATG) in front of the polynucleotide sequence to be expressed and maintaining the correct reading frame to permit expression of the DNA sequence under the control of the expression control sequence and production of the desired product encoded by the polynucleotide sequence. If a gene that one desires to insert into a recombinant DNA molecule does not contain an appropriate start signal, such a start signal can be inserted upstream (5') of and in reading frame with the gene.

Expression of Polypeptides
Isolated Polynucleotide Sequences

The human chromosome 7 genomic clone of accession number AC006454 has been discovered to contain the SNARE YKT6 gene, the human glucokinase gene, the AEBP1 gene, and the POLD2 gene by Genscan analysis (Burge et al., 1997, J. Mol. Biol. 268:78-94), BLAST2 and TBLASTN analysis (Altschul et al., 1997, Nucl. Acids Res. 25:3389-3402), in which the sequence of AC006454 was compared to the SNARE YKT6 cDNA sequence, accession number NM_006555 (McNew et al., 1997, J. Biol. Chem. 272:17776-177783), the human glucokinase cDNA sequence (Tanizawa et al., 1992, Mol. Endocrinol. 6:1070-1081), accession number NM_000162 (major form) and M69051 (minor form), AEBP1 cDNA sequence, accession number NM_001129 (accession number D86479 for the osteoblast type) (Layne et al., 1998, J. Biol. Chem. 273:15654-15660) and the POLD2 cDNA sequence, accession number NM_006230 (Zhang et al., 1995, Genomics 29:179-186).

The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) or long chain PCR may be used. In a specific embodiment, 5' or 3' non-coding portions of each gene may be identified by methods including but are not limited to, filter probing, clone enrichment using specific probes and protocols similar or identical to 5' and 3' "RACE" protocols which are well known in the art. For instance, a method similar to 5' RACE is available for generating the missing 5' end of a desired full-length transcript. (Fromont-Racine et al., 1993, Nucl. Acids Res. 21:1683-1684).

Once the DNA fragments are generated, identification of the specific DNA fragment containing the desired SNARE YKT6 gene, the human glucokinase gene, the AEBP1 gene, or POLD2 gene may be accomplished in a number of ways. For example, if an amount of a portion of a SNARE YKT6 gene, the human glucokinasegene, the POLD2 gene or AEBP1 gene, or its specific RNA, or a fragment thereof, is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). The present invention provides such nucleic acid probes, which can be conveniently prepared from the specific sequences disclosed herein, e.g., a hybridizable probe having a nucleotide sequence corresponding to at least a 10, and preferably a 15, nucleotide fragment of the sequences depicted in SEQ ID NOS:5, 6, 7 or 8. Preferably, a fragment is selected that is highly unique to the encoded polypeptides. Those DNA fragments with substantial homology to the probe will hybridize. As noted above, the greater the degree of homology, the more stringent hybridization conditions can be used. In one embodiment, low stringency hybridization conditions are used to identify a homologous SNARE YKT6, the human glucokinase, the AEBP1, or POLD2 polynucleotide. However, in a preferred aspect, and as demonstrated experimentally herein, a nucleic acid encoding a polypeptide of the invention will hybridize to a nucleic acid derived from the polynucleotide sequence depicted in SEQ ID NOS:5, 6, 7 or 8 or a hybridizable fragment thereof, under moderately stringent conditions; more preferably, it will hybridize under high stringency conditions.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, or antigenic properties as known for the SNARE YKT6, the human glucokinase, the AEBP1, or POLD2 polynucleotide.

A gene encoding SNARE YKT6, the human glucokinase, the AEBP1, or POLD2 polypeptide can also be identified by mRNA selection, i.e., by nucleic acid hybridization followed by in vitro translation. In this procedure, fragments are used to isolate complementary mRNAs by hybridization. Immunoprecipitation analysis or functional assays of the in vitro translation products of the products of the isolated mRNAs identifies the mRNA and, therefore, the complementary DNA fragments, that contain the desired sequences.

Nucleic Acid Constructs

The present invention also relates to nucleic acid constructs comprising a polynucleotide sequence containing the exon/intron segments of the SNARE YKT6 gene (nucleotides 4320-15463 of SEQ ID NO:5), human glucokinase gene (nucleotides 20485-33460 of SEQ ID NO:6), AEBP1 gene (nucleotides 1301-13893 of SEQ ID NO:8) or POLD2 gene (nucleotides 11546-18811 of SEQ ID NO: 7) operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

The invention is further directed to a nucleic acid construct comprising expression control sequences derived from SEQ ID NOS: 5, 6, 7 or 8 and a heterologous polynucleotide sequence.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

The isolated polynucleotide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The control sequence may be an appropriate promoter sequence, a nucleic acid sequence which is recognized by a host cell for expression of the nucleic acid sequence. The promoter sequence contains transcriptional control sequences which regulate the expression of the polynucleotide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, the prokaryotic beta-lactamase gene (VIIIa-Komaroff et al., 1978, *Proc. Natl. Acad. Sci. USA* 75: 3727-3731), as well as the tac promoter (DeBoer et al., 1983, *Proc. Natl. Acad. of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (WO 96/00787), NA2-tpi (a hybrid of the promoters from the genes encoding *Aspergillus niger* neutral alpha-amylase and *Aspergillus oryzae* triose phosphate isomerase), and mutant, truncated, and hybrid promoters thereof.

In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, Yeast 8: 423-488.

Eukaryotic promoters may be obtained from the genomes of viruses such as polyoma virus, fowlpox virus, adenovirus, bovine papilloma virus, avian sarcoma virus, cytomegalovirus, a retrovirus, hepatitis-B virus and SV40. Alternatively, heterologous mammalian promoters, such as the actin promoter or immunoglobulin promoter may be used.

The constructs of the invention may also include enhancers. Enhancers are cis-acting elements of DNA, usually from about 10 to about 300 bp that act on a promoter to increase its transcription. Enhancers from globin, elastase, albumin, alpha-fetoprotein, and insulin enhancers may be used. However, an enhancer from a virus may be used; examples include SV40 on the late side of the replication origin, the cytomegalovirus early promoter enhancer, the polyoma enhancer on the late side of the replication origin and adenovirus enhancers.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

The control sequence may also be a signal peptide coding region, which codes for an amino acid sequence linked to the amino terminus of the polypeptide which can direct the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide. However, any signal peptide coding region which directs the expressed polypeptide into the secretory pathway of a host cell of choice may be used in the present invention.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, the *Rhizomucor miehei* aspartic proteinase gene, or the *Myceliophthora thermophila* laccase gene (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the polynucleotide of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. An example of suitable selectable markers for mammalian cells are those that enable the identification of cells competent to take of the nucleic acids of the present invention, such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77:4216 (1980).

The vectors of the present invention preferably contain an element(s) that permits stable integration of the vector into the host cell genome or autonomous replication of the vector in the cell independent of the genome of the cell.

For integration into the host cell genome, the vector may rely on the polynucleotide sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional polynucleotide sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a polynucleotide sequence of the present invention may be inserted into the host cell to increase production of the gene product. An increase in the copy number of the polynucleotide sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, or a *Streptomyces* cell, e.g., *Streptomyces lividans* or *Streptomyces murinus*, or gram negative bacteria such as *E. coli* and *Pseudomonas* sp.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may be a eukaryote, such as a mammalian cell (e.g., human cell), an insect cell, a plant cell or a fungal cell. Mammalian host cells that could be used include but are not limited to human Hela, embryonic kidney cells (293), lung cells, H9 and Jurkat cells, mouse NIH3T3 and C127 cells, Cos 1, Cos 7 and CV1, quail QC1-3 cells, mouse L cells and Chinese Hamster ovary (CHO) cells. These cells may be transfected with a vector containing a transcriptional regulatory sequence, a protein coding sequence and transcriptional termination sequences. Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The host cell may be a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra). The fungal host cell may also be a yeast cell. ÖYeastÖ as used herein includes ascosporogenous yeast (Endomycetales), basidiosporogenous yeast, and yeast belonging to the *Fungi Imperfecti* (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980). The fungal host cell may also be a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology*, Methods in Enzymology, Volume 194, pp 182-187, Academic Press, Inc., New York; Ito et al., 1983, *Journal of Bacteriology* 153: 163; and Hinnen et al., 1978, *Proc. e Natl Acad. f Sci.s USA* 75: 1920.

Methods of Production

The present invention also relates to methods for producing a polypeptide of the present invention comprising (a) cultivating a host cell under conditions conducive for production of the polypeptide; and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. In a specific embodiment, an enzyme assay may be used to determine the activity of the polypeptide. For example, AEBP1 activity can be determined by measuring carboxypeptidase activity as described by Muise and Ro, 1999, Biochem. J. 343:341-345. Here, the conversion of hippuryl-L-arginine, hippuryl-L-lysine or hippuryl-L-phenylalanine to hippuric acid may be monitored spectrophotometrically. POLD2 activity may be detected by assaying for DNA polymerase activity (see, for example, Ng et al., 1991, J. Biol. Chem. 266:11699-11704).

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing, differential solubility (e.g., ammonium sulfate precipitation), SDS-PAGE, or extraction (see, e.g., *Protein Purification*, J.-C. Janson and Lars Ryden, editors, VCH Publishers, New York, 1989).

Antibodies

According to the invention, the SNARE YKT6, human glucokinase, AEBP1 or POLD2 polypeptides produced according to the method of the present invention may be used as an immunogen to generate any of these polypeptides. Such antibodies include but are not limited to polyclonal, monoclonal, chimeric, single chain, Fab fragments, and an Fab expression library.

Various procedures known in the art may be used for the production of antibodies. For the production of antibody, various host animals can be immunized by injection with the polypeptide thereof, including but not limited to rabbits, mice, rats, sheep, goats, etc. In one embodiment, the polypeptide or fragment thereof can optionally be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the SNARE YKT6, human glucokinase, AEBP1 or POLD2 polypeptide, any technique that provides for the production of antibody molecules by continuous cell lines in culture may be used. These include but are not limited to the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026-2030) or by transforming human B cells with EBV virus in vitro (Cole et al., 1985, in Monoclonal Antibodies and Cancer Therapy, Alan R. Liss, pp. 77-96). In fact, according to the invention, techniques developed for the production of "chimeric antibodies" (Morrison et al., 1984, J. Bacteriol. 159-870; Neuberger et al., 1984, Nature 312:604-608; Takeda et al., 1985, Nature 314:452-454) by splicing the genes from a mouse antibody molecule specific for the SNARE YKT6, human glucokinase, AEBP1 or POLD2 polypeptide together with genes from a human antibody molecule of appropriate biological activity can be used; such antibodies are within the scope of this invention.

According to the invention, techniques described for the production of single chain antibodies (U.S. Pat. No. 4,946,778) can be adapted to produce polypeptide-specific single chain antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity for the SNARE YKT6, AEBP1, human glucokinase or POLD2 polypeptides.

Antibody fragments which contain the idiotype of the antibody molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a particular polypeptide, one may assay generated hybridomas for a product which binds to a particular polypeptide fragment containing such epitope. For selection of an antibody specific to a particular polypeptide from a particular species of animal, one can select on the basis of positive binding with the polypeptide expressed by or isolated from cells of that species of animal.

Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Uses of Polynucleotides

Diagnostics

Polynucleotides containing noncoding regions of SEQ ID NOS:5, 6, 7 or 8 may be used as probes for detecting mutations from samples from a patient. Genomic DNA may be isolated from the patient. A mutation(s) may be detected by Southern blot analysis, specifically by hybridizing restriction digested genomic DNA to various probes and subjecting to agarose electrophoresis.

Polynucleotides containing noncoding regions may be used as PCR primers and may be used to amplify the genomic DNA isolated from the patients. Additionally, primers may be obtained by routine or long range PCR, that can yield products containing more than one exon and intervening intron. The sequence of the amplified genomic DNA from the patient may be determined using methods known in the art. Such probes may be between 10-100 nucleotides in length and may preferably be between 20-50 nucleotides in length.

Thus the invention is thus directed to kits comprising these polynucleotide probes. In a specific embodiment, these probes are labeled with a detectable substance.

Antisense Oligonucleotides and Mimetics

The invention is further directed to antisense oligonucleotides and mimetics to these polynucleotide sequences. Antisense technology can be used to control gene expression through triple-helix formation or antisense DNA or RNA, both of which methods are based on binding of a polynucleotide to DNA or RNA. A DNA oligonucleotide is designed to be complementary to a region of the gene involved in transcription or RNA processing (triple helix (see Lee et al., Nucl. Acids Res., 6:3073 (1979); Cooney et al, Science, 241:456 (1988); and Dervan et al., Science, 251: 1360 (1991)), thereby preventing transcription and the production of said polypeptides.

The antisense oligonucleotides or mimetics of the present invention may be used to decrease levels of a polypeptide. For example, SNARE YKT6 has been found to be essential for vesicle-associated endoplasmic reticulum-Golgi transport and cell growth. Therefore, the SNARE YKT6 antisense oligonucleotides of the present invention could be used to inhibit cell growth and in particular, to treat or prevent tumor growth. POLD2 is necessary for DNA replication. POLD2 antisense sequences could also be used to inhibit cell growth. Glucokinase and AEBP1 antisense sequences may be used to treat hyperglycemia.

The antisense oligonucleotides of the present invention may be formulated into pharmaceutical compositions. These compositions may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention, the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on EC50 as found to be effective in in vitro and in vivo animal models.

In general, dosage is from 0.01 ug to 10 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 10 g per kg of body weight, once or more daily, to once every 20 years.

Gene Therapy

As noted above, SNARE YKT6 is necessary for cell growth, POLD2 is involved in DNA replication and repair, AEBP1 is involved in repressing adipogenesis and glucokinase is involved in glucose sensing in pancreatic islet beta cells and liver. Therefore, the SNARE YKT6 gene may be used to modulate or prevent cell apoptosis and treat such disorders as virus-induced lymphocyte depletion (AIDS); cell death in neurodegenerative disorders characterized by the gradual loss of specific sets of neurons (e.g., Alzheimer's Disease, Parkinson's disease, ALS, retinitis pigmentosa, spinal muscular atrophy and various forms of cerebellar degeneration), cell death in blood cell disorders resulting from deprivation of growth factors (anemia associated with chronic disease, aplastic anemia, chronic neutropenia and myelodysplastic syndromes) and disorders arising out of an acute loss of blood flow (e.g., myocardial infarctions and stroke). The glucokinase gene may be used to treat diabetes mellitus. The AEBP1 gene may be used to modulate or inhibit adipogenesis and treat obesity, diabetes mellitus and/or osteopenic disorders. POLD2 may be used to treat defects in DNA repair such as xeroderma pigmentosum, progeria and ataxia telangiectasia.

As described herein, the polynucleotide of the present invention may be introduced into a patient's cells for therapeutic uses. As will be discussed in further detail below, cells can be transfected using any appropriate means, including viral vectors, as shown by the example, chemical transfectants, or physico-mechanical methods such as electroporation and direct diffusion of DNA. See, for example, Wolff, Jon A, et al., "Direct gene transfer into mouse muscle in vivo," *Science,* 247, 1465-1468, 1990; and Wolff, Jon A, "Human dystrophin expression in mdx mice after intramuscular injection of DNA constructs," *Nature,* 352, 815-818, 1991. As used herein, vectors are agents that transport the gene into the cell without degradation and include a promoter yielding expression of the gene in the cells into which it is delivered. As will be discussed in further detail below, promoters can be general promoters, yielding expression in a variety of mammalian cells, or cell specific, or even nuclear versus cytoplasmic specific. These are known to those skilled in the art and can be constructed using standard molecular biology protocols. Vectors have been divided into two classes:

a) Biological agents derived from viral, bacterial or other sources.

b) Chemical physical methods that increase the potential for gene uptake, directly introduce the gene into the nucleus or target the gene to a cell receptor.

Biological Vectors

Viral vectors have higher transaction (ability to introduce genes) abilities than do most chemical or physical methods to introduce genes into cells. Vectors that may be used in the present invention include viruses, such as adenoviruses, adeno associated virus (AAV), vaccinia, herpesviruses, baculoviruses and retroviruses, bacteriophages, cosmids, plasmids, fungal vectors and other recombination vehicles typically used in the art which have been described for expression in a variety of eukaryotic and prokaryotic hosts, and may be used for gene therapy as well as for simple protein expression. Polynucleotides are inserted into vector genomes using methods well known in the art.

Retroviral vectors are the vectors most commonly used in clinical trials, since they carry a larger genetic payload than other viral vectors. However, they are not useful in non-proliferating cells. Adenovirus vectors are relatively stable and easy to work with, have high titers, and can be delivered in aerosol formulation. Pox viral vectors are large and have several sites for inserting genes, they are thermostable and can be stored at room temperature.

Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, phosphoglycerate kinase (PGK) promoter, and the like. Alternatively, the promoter may be an endogenous adenovirus promoter, for example the E1 a promoter or the Ad2 major late promoter (MLP). Similarly, those of ordinary skill in the art can construct adenoviral vectors utilizing endogenous or heterologous poly A addition signals.

Plasmids are not integrated into the genome and the vast majority of them are present only from a few weeks to several months, so they are typically very safe. However, they have lower expression levels than retroviruses and since cells have the ability to identify and eventually shut down foreign gene expression, the continuous release of DNA from the polymer to the target cells substantially increases the duration of functional expression while maintaining the benefit of the safety associated with non-viral transfections.

Chemical/Physical Vectors

Other methods to directly introduce genes into cells or exploit receptors on the surface of cells include the use of liposomes and lipids, ligands for specific cell surface receptors, cell receptors, and calcium phosphate and other chemical mediators, microinjections directly to single cells, electroporation and homologous recombination. Liposomes are commercially available from Gibco BRL, for example, as LIPOFECTIN and LIPOFECTACE, which are formed of cationic lipids such as N-[1-(2,3 dioleyloxy)-propyl]-n,n,n-trimethylammonium chloride (DOTMA) and dimethyl dioctadecylammonium bromide (DDAB). Numerous methods are also published for making liposomes, known to those skilled in the art.

For example, Nucleic acid-Lipid Complexes—Lipid carriers can be associated with naked nucleic acids (e.g., plasmid DNA) to facilitate passage through cellular membranes. Cationic, anionic, or neutral lipids can be used for this purpose. However, cationic lipids are preferred because they have been shown to associate better with DNA which, generally, has a negative charge. Cationic lipids have also been shown to mediate intracellular delivery of plasmid DNA (Felgner and Ringold, Nature 337:387 (1989)). Intravenous injection of cationic lipid-plasmid complexes into mice has been shown to result in expression of the DNA in lung (Brigham et al., Am. J. Med. Sci. 298:278 (1989)). See also, Osaka et al., J. Pharm. Sci. 85(6):612-618 (1996); San et al., Human Gene Therapy 4:781-788 (1993); Senior et al., Biochemica et Biophysica Acta 1070:173-179 (1991); Kabanov and Kabanov, Bioconjugate Chem. 6:7-20 (1995); Remy et al., Bioconjugate Chem. 5:647-654 (1994); Behr, J-P., Bioconjugate Chem 5:382-389 (1994); Behr et al., Proc. Natl. Acad. Sci., USA 86:6982-6986 (1989); and Wyman et al., Biochem. 36:3008-3017 (1997).

Cationic lipids are known to those of ordinary skill in the art. Representative cationic lipids include those disclosed, for example, in U.S. Pat. No. 5,283,185; and e.g., U.S. Pat. No. 5,767,099. In a preferred embodiment, the cationic lipid is N4-spermine cholesteryl carbamate (GL-67) disclosed in U.S. Pat. No. 5,767,099. Additional preferred lipids include N4-spermidine cholestryl carbamate (GL-53) and 1-(N-4-spermind)-2,3-dilaurylglycerol carbamate (GL-89).

The vectors of the invention may be targeted to specific cells by linking a targeting molecule to the vector. A targeting molecule is any agent that is specific for a cell or tissue type of interest, including for example, a ligand, antibody, sugar, receptor, or other binding molecule.

Invention vectors may be delivered to the target cells in a suitable composition, either alone, or complexed, as provided above, comprising the vector and a suitably acceptable carrier. The vector may be delivered to target cells by methods known in the art, for example, intravenous, intramuscular, intranasal, subcutaneous, intubation, lavage, and the like. The vectors may be delivered via in vivo or ex vivo applications. In vivo applications involve the direct administration of an adenoviral vector of the invention formulated into a composition to the cells of an individual. Ex vivo applications involve the transfer of the adenoviral vector directly to harvested autologous cells which are maintained in vitro, followed by readministration of the transduced cells to a recipient.

In a specific embodiment, the vector is transfected into antigen-presenting cells. Suitable sources of antigen-presenting cells (APCs) include, but are not limited to, whole cells such as dendritic cells or macrophages; purified MHC class I molecule complexed to §2-microglobulin and foster antigen-presenting cells. In a specific embodiment, the vectors of the present invention may be introduced into T cells or B cells using methods known in the art (see, for example, Tsokos and Nepom, 2000, J. Clin. Invest. 106:181-183).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosure of which are incorporated by reference in their entireties.

What is claimed is:

1. A method of identifying a nucleotide sequence variant of a 5'-noncoding region, 3'-noncoding region or intron region of SEQ ID NO: 7, wherein said variant encodes a polypeptide that has human POLD2 activity, wherein SEQ ID NO: 7 consists of a 5'-noncoding region shown in sequence segment 1-11545 of SEQ ID NO: 7, a 3'-non coding region shown in sequence segment 18654-19000 of SEQ ID NO: 7, exon regions shown in sequence segment 11546-11764, 15534-15656, 15857-15979, 16351-16464, 16582-16782, 17089-17169, 17327-17484, 17704-17829, 18199-18303, 1653-18811 of SEQ ID NO: 7 and intron regions shown in sequence segments 11765-15533, 15657-15856, 15980-16350, 16465-16581, 16783-17088, 17170-17326, 17485-17703, 17830-18198, 18304-18652 of SEQ ID NO: 7 or its complementary sequence comprising (a) isolating genomic polynucleotide from a sample and
(b) determining the presence or absence of a nucleotide sequence variation in said genomic polynucleotide by comparing the nucleotide sequence of SEQ ID NO: 7 with the nucleotide sequence of the isolated genomic polynucleotide and establishing if and where a difference occurs between the two nucleic acid sequences thereby identifying a nucleotide sequence variant of SEQ ID NO: 7 or its complement.

2. A method for detecting the presence of: (a) a nucleic acid molecule 19000 nucleotides in length which is at least 99% identical to SEQ ID NO: 7 which encodes a polypeptide that has human glucokinase activity, wherein SEQ ID NO: 7 consists of a 5'-noncoding region shown in sequence segment 1-11545 of SEQ ID NO: 7, a 3'-non coding region shown in sequence segment 18654-19000 of SEQ ID NO: 7 and an intron region shown in sequence segments 11765-15533, 15657-15856, 15980-16350, 16465-16581, 16783-17088, 17170-17326, 17485-17703, 17830-18198, 18304-18652 of SEQ ID NO: 7; (b) a fragment of (a), comprising at least nucleotides 11546-18811 of SEQ ID NO: 7 which encodes a polypeptide having human POLD2 activity and (c) a nucleic acid molecule which is a complement of the nucleic acid molecules specified in (a)-(b) in a sample, comprising contacting the sample with a polynucleotide probe comprising at least 20 contiguous nucleotides that hybridizes to said nucleic acid molecule under stringent conditions and determining whether the polynucleotide probe binds to said nucleic acid molecule in the sample.

* * * * *

```
                              SEQUENCE LISTING

<160> NUMBER OF SEQ ID NOS: 8

<210> SEQ ID NO 1
<211> LENGTH: 198
<212> TYPE: PRT
<213> ORGANISM: Homo sapiens

<400> SEQUENCE: 1

Met Lys Leu Tyr Ser Leu Ser Val Leu Tyr Lys Gly Glu Ala Lys Val
1               5                   10                  15

Val Leu Leu Lys Ala Ala Tyr Asp Val Ser Ser Phe Ser Phe Phe Gln
                20                  25                  30

Arg Ser Ser Val Gln Glu Phe Met Thr Phe Thr Ser Gln Leu Ile Val
            35                  40                  45

Glu Arg Ser Ser Lys Gly Thr Arg Ala Ser Val Lys Gly Gln Asp Tyr
    50                  55                  60

Leu Cys His Val Tyr Val Arg Asn Asp Ser Leu Ala Gly Val Val Ile
65                  70                  75                  80

Ala Asp Asn Glu Tyr Pro Ser Arg Val Ala Phe Thr Leu Leu Glu Lys
                85                  90                  95

Val Leu Asp Glu Phe Ser Lys Gln Val Asp Arg Ile Asp Trp Pro Val
            100                 105                 110

Gly Ser Pro Ala Thr Ile His Tyr Pro Ala Leu Asp Gly His Leu Ser
        115                 120                 125

Arg Tyr Gln Asn Pro Arg Glu Ala Asp Pro Met Thr Lys Val Gln Ala
    130                 135                 140

Glu Leu Asp Glu Thr Lys Ile Ile Leu His Asn Thr Met Glu Ser Leu
145                 150                 155                 160

Leu Glu Arg Gly Glu Lys Leu Asp Asp Leu Val Ser Lys Ser Glu Val
                165                 170                 175

Leu Gly Thr Gln Ser Lys Ala Phe Tyr Lys Thr Ala Arg Lys Gln Asn
            180                 185                 190

Ser Cys Cys Ala Ile Met
        195

<210> SEQ ID NO 2
<211> LENGTH: 464
<212> TYPE: PRT
<213> ORGANISM: Homo sapiens

<400> SEQUENCE: 2

Met Pro Arg Pro Arg Ser Gln Leu Pro Gln Pro Asn Ser Gln Val Glu
1               5                   10                  15

Gln Ile Leu Ala Glu Phe Gln Leu Gln Glu Glu Asp Leu Lys Lys Val
                20                  25                  30

Met Arg Arg Met Gln Lys Glu Met Asp Arg Gly Leu Arg Leu Glu Thr
            35                  40                  45

His Glu Glu Ala Ser Val Lys Met Leu Pro Thr Tyr Val Arg Ser Thr
    50                  55                  60

Pro Glu Gly Ser Glu Val Gly Asp Phe Leu Ser Leu Asp Leu Gly Gly
65                  70                  75                  80
```

Thr Asn Phe Arg Val Met Leu Val Lys Val Gly Glu Gly Glu Gly
            85                  90                  95

Gln Trp Ser Val Lys Thr Lys His Gln Thr Tyr Ser Ile Pro Glu Asp
        100                 105                 110

Ala Met Thr Gly Thr Ala Glu Met Leu Phe Asp Tyr Ile Ser Glu Cys
    115                 120                 125

Ile Ser Asp Phe Leu Asp Lys His Gln Met Lys His Lys Lys Leu Pro
130                 135                 140

Leu Gly Phe Thr Phe Ser Phe Pro Val Arg His Glu Asp Ile Asp Lys
145                 150                 155                 160

Gly Ile Leu Leu Asn Trp Thr Lys Gly Phe Lys Ala Ser Gly Ala Glu
                165                 170                 175

Gly Asn Asn Val Val Gly Leu Leu Arg Asp Ala Ile Lys Arg Arg Gly
            180                 185                 190

Asp Phe Glu Met Asp Val Val Ala Met Val Asn Asp Thr Val Ala Thr
        195                 200                 205

Met Ile Ser Cys Tyr Tyr Glu Asp His Gln Cys Glu Val Gly Met Ile
    210                 215                 220

Val Gly Thr Gly Cys Asn Ala Cys Tyr Met Glu Glu Met Gln Asn Val
225                 230                 235                 240

Glu Leu Val Glu Gly Asp Glu Gly Arg Met Cys Val Asn Thr Glu Trp
                245                 250                 255

Gly Ala Phe Gly Asp Ser Gly Glu Leu Asp Glu Phe Leu Leu Glu Tyr
            260                 265                 270

Asp Arg Leu Val Asp Glu Ser Ser Ala Asn Pro Gly Gln Gln Leu Tyr
        275                 280                 285

Glu Lys Leu Ile Gly Gly Lys Tyr Met Gly Glu Leu Val Arg Leu Val
    290                 295                 300

Leu Leu Arg Leu Val Asp Glu Asn Leu Leu Phe His Gly Glu Ala Ser
305                 310                 315                 320

Glu Gln Leu Arg Thr Arg Gly Ala Phe Glu Thr Arg Phe Val Ser Gln
                325                 330                 335

Val Glu Ser Asp Thr Gly Asp Arg Lys Gln Ile Tyr Asn Ile Leu Ser
            340                 345                 350

Thr Leu Gly Leu Arg Pro Ser Thr Thr Asp Cys Asp Ile Val Arg Arg
        355                 360                 365

Ala Cys Glu Ser Val Ser Thr Arg Ala Ala His Met Cys Ser Ala Gly
    370                 375                 380

Leu Ala Gly Val Ile Asn Arg Met Arg Glu Ser Arg Ser Glu Asp Val
385                 390                 395                 400

Met Arg Ile Thr Val Gly Val Asp Gly Ser Val Tyr Lys Leu His Pro
                405                 410                 415

Ser Phe Lys Glu Arg Phe His Ala Ser Val Arg Arg Leu Thr Pro Ser
            420                 425                 430

Cys Glu Ile Thr Phe Ile Glu Ser Glu Glu Gly Ser Gly Arg Gly Ala
        435                 440                 445

Ala Leu Val Ser Ala Val Ala Cys Lys Lys Ala Cys Met Leu Gly Gln
    450                 455                 460

<210> SEQ ID NO 3
<211> LENGTH: 1158
<212> TYPE: PRT
<213> ORGANISM: Homo sapiens

<400> SEQUENCE: 3

```
Met Ala Ala Val Arg Gly Ala Pro Leu Leu Ser Cys Leu Leu Ala Leu
1               5                   10                  15
Leu Ala Leu Cys Pro Gly Gly Arg Pro Gln Thr Val Leu Thr Asp Asp
            20                  25                  30
Glu Ile Glu Glu Phe Leu Glu Gly Phe Leu Ser Glu Leu Glu Pro Glu
        35                  40                  45
Pro Arg Glu Asp Asp Val Glu Ala Pro Pro Pro Glu Pro Thr Pro
    50                  55                  60
Arg Val Arg Lys Ala Gln Ala Gly Gly Lys Pro Gly Lys Arg Pro Gly
65                  70                  75                  80
Thr Ala Ala Glu Val Pro Pro Glu Lys Thr Lys Asp Lys Gly Lys Lys
                85                  90                  95
Gly Lys Lys Asp Lys Gly Pro Lys Val Pro Lys Glu Ser Leu Glu Gly
            100                 105                 110
Ser Pro Arg Pro Pro Lys Lys Gly Lys Glu Lys Pro Pro Lys Ala Thr
        115                 120                 125
Lys Lys Pro Lys Glu Lys Pro Pro Lys Ala Thr Lys Lys Pro Lys Glu
    130                 135                 140
Glu Pro Pro Lys Ala Thr Lys Lys Pro Lys Glu Lys Pro Pro Lys Ala
145                 150                 155                 160
Thr Lys Lys Pro Pro Ser Gly Lys Arg Pro Pro Ile Leu Ala Pro Ser
                165                 170                 175
Glu Thr Leu Glu Trp Pro Leu Pro Pro Pro Ser Pro Gly Pro Glu
            180                 185                 190
Glu Leu Pro Gln Glu Gly Gly Ala Pro Leu Ser Asn Asn Trp Gln Asn
        195                 200                 205
Pro Gly Glu Glu Thr His Val Glu Ala Gln Glu His Gln Pro Glu Pro
    210                 215                 220
Glu Glu Glu Thr Glu Gln Pro Thr Leu Asp Tyr Asn Asp Gln Ile Glu
225                 230                 235                 240
Arg Glu Asp Tyr Glu Asp Phe Glu Tyr Ile Arg Arg Gln Lys Gln Pro
                245                 250                 255
Arg Pro Pro Pro Ser Arg Arg Arg Pro Glu Arg Val Trp Pro Glu
            260                 265                 270
Pro Pro Glu Glu Lys Ala Pro Ala Pro Ala Pro Glu Glu Arg Ile Glu
        275                 280                 285
Pro Pro Val Lys Pro Leu Leu Pro Pro Leu Pro Pro Asp Tyr Gly Asp
    290                 295                 300
Gly Tyr Val Ile Pro Asn Tyr Asp Asp Met Asp Tyr Tyr Phe Gly Pro
305                 310                 315                 320
Pro Pro Pro Gln Lys Pro Asp Ala Glu Arg Gln Thr Asp Glu Glu Lys
                325                 330                 335
Glu Glu Leu Lys Lys Pro Lys Lys Glu Asp Ser Ser Pro Lys Glu Glu
            340                 345                 350
Thr Asp Lys Trp Ala Val Glu Lys Gly Lys Asp His Lys Glu Pro Arg
        355                 360                 365
Lys Gly Glu Glu Leu Glu Glu Glu Trp Thr Pro Thr Glu Lys Val Lys
    370                 375                 380
Cys Pro Pro Ile Gly Met Glu Ser His Arg Ile Glu Asp Asn Gln Ile
385                 390                 395                 400
Arg Ala Ser Ser Met Leu Arg His Gly Leu Gly Ala Gln Arg Gly Arg
                405                 410                 415
```

```
Leu Asn Met Gln Thr Gly Ala Thr Glu Asp Tyr Tyr Asp Gly Ala
            420                 425                 430

Trp Cys Ala Glu Asp Asp Ala Arg Thr Gln Trp Ile Glu Val Asp Thr
        435                 440                 445

Arg Arg Thr Thr Arg Phe Thr Gly Val Ile Thr Gln Gly Arg Asp Ser
    450                 455                 460

Ser Ile His Asp Asp Phe Val Thr Thr Phe Phe Val Gly Phe Ser Asn
465                 470                 475                 480

Asp Ser Gln Thr Trp Val Met Tyr Thr Asn Gly Tyr Glu Glu Met Thr
                485                 490                 495

Phe His Gly Asn Val Asp Lys Asp Thr Pro Val Leu Ser Glu Leu Pro
            500                 505                 510

Glu Pro Val Val Ala Arg Phe Ile Arg Ile Tyr Pro Leu Thr Trp Asn
        515                 520                 525

Gly Ser Leu Cys Met Arg Leu Glu Val Leu Gly Cys Ser Val Ala Pro
    530                 535                 540

Val Tyr Ser Tyr Tyr Ala Gln Asn Glu Val Val Ala Thr Asp Asp Leu
545                 550                 555                 560

Asp Phe Arg His His Ser Tyr Lys Asp Met Arg Gln Leu Met Lys Val
                565                 570                 575

Val Asn Glu Glu Cys Pro Thr Ile Thr Arg Thr Tyr Ser Leu Gly Lys
            580                 585                 590

Ser Ser Arg Gly Leu Lys Ile Tyr Ala Met Glu Ile Ser Asp Asn Pro
        595                 600                 605

Gly Glu His Glu Leu Gly Glu Pro Glu Phe Arg Tyr Thr Ala Gly Ile
    610                 615                 620

His Gly Asn Glu Val Leu Gly Arg Glu Leu Leu Leu Leu Met Gln
625                 630                 635                 640

Tyr Leu Cys Arg Glu Tyr Arg Asp Gly Asn Pro Arg Val Arg Ser Leu
                645                 650                 655

Val Gln Asp Thr Arg Ile His Leu Val Pro Ser Leu Asn Pro Asp Gly
            660                 665                 670

Tyr Glu Val Ala Ala Gln Met Gly Ser Glu Phe Gly Asn Trp Ala Leu
        675                 680                 685

Gly Leu Trp Thr Glu Glu Gly Phe Asp Ile Phe Glu Asp Phe Pro Asp
    690                 695                 700

Leu Asn Ser Val Leu Trp Gly Ala Glu Glu Arg Lys Trp Val Pro Tyr
705                 710                 715                 720

Arg Val Pro Asn Asn Leu Pro Ile Pro Glu Arg Tyr Leu Ser Pro
                725                 730                 735

Asp Ala Thr Val Ser Thr Glu Val Arg Ala Ile Ile Ala Trp Met Glu
            740                 745                 750

Lys Asn Pro Phe Val Leu Gly Ala Asn Leu Asn Gly Gly Glu Arg Leu
        755                 760                 765

Val Ser Tyr Pro Tyr Asp Met Ala Arg Thr Pro Thr Gln Glu Gln Leu
    770                 775                 780

Leu Ala Ala Ala Met Ala Ala Arg Gly Glu Asp Glu Asp Glu Val
785                 790                 795                 800

Ser Glu Ala Gln Glu Thr Pro Asp His Ala Ile Phe Arg Trp Leu Ala
                805                 810                 815

Ile Ser Phe Ala Ser Ala His Leu Thr Leu Thr Glu Pro Tyr Arg Gly
            820                 825                 830

Gly Cys Gln Ala Gln Asp Tyr Thr Gly Gly Met Gly Ile Val Asn Gly
```

```
                    835                 840                 845
Ala Lys Trp Asn Pro Arg Thr Gly Thr Ile Asn Asp Phe Ser Tyr Leu
850                 855                 860

His Thr Asn Cys Leu Glu Leu Ser Phe Tyr Leu Gly Cys Asp Lys Phe
865                 870                 875                 880

Pro His Glu Ser Glu Leu Pro Arg Glu Trp Glu Asn Asn Lys Glu Ala
                885                 890                 895

Leu Leu Thr Phe Met Glu Gln Val His Arg Gly Ile Lys Gly Val Val
                900                 905                 910

Thr Asp Glu Gln Gly Ile Pro Ile Ala Asn Ala Thr Ile Ser Val Ser
                915                 920                 925

Gly Ile Asn His Gly Val Lys Thr Ala Ser Gly Gly Asp Tyr Trp Arg
                930                 935                 940

Ile Leu Asn Pro Gly Glu Tyr Arg Val Thr Ala His Ala Glu Gly Tyr
945                 950                 955                 960

Thr Pro Ser Ala Lys Thr Cys Asn Val Asp Tyr Asp Ile Gly Ala Thr
                965                 970                 975

Gln Cys Asn Phe Ile Leu Ala Arg Ser Asn Trp Lys Arg Ile Arg Glu
                980                 985                 990

Ile Met Ala Met Asn Gly Asn Arg  Pro Ile Pro His Ile  Asp Pro Ser
                995                 1000                1005

Arg Pro Met Thr Pro Gln Gln  Arg Arg Leu Gln Gln  Arg Arg Leu
        1010                1015                1020

Gln His Arg Leu Arg Leu Arg  Ala Gln Met Arg Leu  Arg Arg Leu
        1025                1030                1035

Asn Ala Thr Thr Thr Leu Gly  Pro His Thr Val Pro  Pro Thr Leu
        1040                1045                1050

Pro Pro Ala Pro Ala Thr Thr  Leu Ser Thr Thr Ile  Glu Pro Trp
        1055                1060                1065

Gly Leu Ile Pro Pro Thr Thr  Ala Gly Trp Glu Glu  Ser Glu Thr
        1070                1075                1080

Glu Thr Tyr Thr Glu Val Val  Thr Glu Phe Gly Thr  Glu Val Glu
        1085                1090                1095

Pro Glu Phe Gly Thr Lys Val  Glu Pro Glu Phe Glu  Thr Gln Leu
        1100                1105                1110

Glu Pro Glu Phe Glu Thr Gln  Leu Glu Pro Glu Phe  Glu Glu Glu
        1115                1120                1125

Glu Glu Glu Glu Lys Glu Glu  Glu Ile Ala Thr Gly  Gln Ala Phe
        1130                1135                1140

Pro Phe Thr Thr Val Glu Thr  Tyr Thr Val Asn Phe  Gly Asp Phe
        1145                1150                1155

<210> SEQ ID NO 4
<211> LENGTH: 469
<212> TYPE: PRT
<213> ORGANISM: Homo sapiens

<400> SEQUENCE: 4

Met Phe Ser Glu Gln Ala Ala Gln Arg Ala His Thr Leu Leu Ser Pro
1               5                   10                  15

Pro Ser Ala Asn Asn Ala Thr Phe Ala Arg Val Pro Val Ala Thr Tyr
                20                  25                  30

Thr Asn Ser Ser Gln Pro Phe Arg Leu Gly Glu Arg Ser Phe Ser Arg
                35                  40                  45
```

```
Gln Tyr Ala His Ile Tyr Ala Thr Arg Leu Ile Gln Met Arg Pro Phe
 50                  55                  60

Leu Glu Asn Arg Ala Gln Gln His Trp Gly Ser Gly Val Gly Val Lys
 65                  70                  75                  80

Lys Leu Cys Glu Leu Gln Pro Glu Glu Lys Cys Cys Val Val Gly Thr
                 85                  90                  95

Leu Phe Lys Ala Met Pro Leu Gln Pro Ser Ile Leu Arg Glu Val Ser
                100                 105                 110

Glu Glu His Asn Leu Leu Pro Gln Pro Pro Arg Ser Lys Tyr Ile His
                115                 120                 125

Pro Asp Asp Glu Leu Val Leu Glu Asp Glu Leu Gln Arg Ile Lys Leu
130                 135                 140

Lys Gly Thr Ile Asp Val Ser Lys Leu Val Thr Gly Thr Val Leu Ala
145                 150                 155                 160

Val Phe Gly Ser Val Arg Asp Asp Gly Lys Phe Leu Val Glu Asp Tyr
                165                 170                 175

Cys Phe Ala Asp Leu Ala Pro Gln Lys Pro Ala Pro Pro Leu Asp Thr
                180                 185                 190

Asp Arg Phe Val Leu Leu Val Ser Gly Leu Gly Leu Gly Gly Gly Gly
                195                 200                 205

Gly Glu Ser Leu Leu Gly Thr Gln Leu Leu Val Asp Val Val Thr Gly
210                 215                 220

Gln Leu Gly Asp Glu Gly Glu Gln Cys Ser Ala Ala His Val Ser Arg
225                 230                 235                 240

Val Ile Leu Ala Gly Asn Leu Leu Ser His Ser Thr Gln Ser Arg Asp
                245                 250                 255

Ser Ile Asn Lys Ala Lys Tyr Leu Thr Lys Lys Thr Gln Ala Ala Ser
                260                 265                 270

Val Glu Ala Val Lys Met Leu Asp Glu Ile Leu Leu Gln Leu Ser Ala
                275                 280                 285

Ser Val Pro Val Asp Val Met Pro Gly Glu Phe Asp Pro Thr Asn Tyr
                290                 295                 300

Thr Leu Pro Gln Gln Pro Leu His Pro Cys Met Phe Pro Leu Ala Thr
305                 310                 315                 320

Ala Tyr Ser Thr Leu Gln Leu Val Thr Asn Pro Tyr Gln Ala Thr Ile
                325                 330                 335

Asp Gly Val Arg Phe Leu Gly Thr Ser Gly Gln Asn Val Ser Asp Ile
                340                 345                 350

Phe Arg Tyr Ser Ser Met Glu Asp His Leu Glu Ile Leu Glu Trp Thr
                355                 360                 365

Leu Arg Val Arg His Ile Ser Pro Thr Ala Pro Asp Thr Leu Gly Cys
370                 375                 380

Tyr Pro Phe Tyr Lys Thr Asp Pro Phe Ile Phe Pro Glu Cys Pro His
385                 390                 395                 400

Val Tyr Phe Cys Gly Asn Thr Pro Ser Phe Gly Ser Lys Ile Ile Arg
                405                 410                 415

Gly Pro Glu Asp Gln Thr Val Leu Leu Val Thr Val Pro Asp Phe Ser
                420                 425                 430

Ala Thr Gln Thr Ala Cys Leu Val Asn Leu Arg Ser Leu Ala Cys Gln
                435                 440                 445

Pro Ile Ser Phe Ser Gly Phe Gly Ala Glu Asp Asp Leu Gly Gly
450                 455                 460

Leu Gly Leu Gly Pro
```

465

<210> SEQ ID NO 5
<211> LENGTH: 39000
<212> TYPE: DNA
<213> ORGANISM: Homo sapiens

<400> SEQUENCE: 5

| | | | | | |
|---|---|---|---|---|---:|
| ccagacatag | gcaaggcgca | aggtgataca | gtaggcagcc | accatggggg | ccaggaggct | 60 |
| ccagcagagg | ccacacaacc | agcccagaat | ccaggacaga | gagctggaat | ggagacaggg | 120 |
| aagccagata | ccaggccaga | ctggccaggt | gctacaggcc | tgtgggccag | gccaggcttg | 180 |
| gggacttcgt | cctgggtgtg | aaggagacag | gcacccctga | ggccttccct | ctgcatctcc | 240 |
| agcccaagct | aagcgcaaac | tcttaggttg | gagtaaggag | taaccccctg | ccaagtttct | 300 |
| cctgtcctca | ggctccaccc | accacctatg | ctgcctggcc | ccatggggca | cacgctcagg | 360 |
| cccagcctgg | gaaagcaact | gcacctgcct | gtgctatgct | ggcccttctc | agcctcaatg | 420 |
| ccctcctccc | tccccgacgc | accctcgtgg | ccccgctgg  | gccccctgat | gcaccctcat | 480 |
| gtctccatgg | caacctgctc | agagtgtggc | cctgcccttg | gctcccctcc | acacctgtgt | 540 |
| cccaggcagt | gccacggcac | tttcctaaac | agaaggatgg | gcttcaaaac | agtcccagac | 600 |
| actaaacaca | cctgcatttt | gggtccaagt | aacttctgac | aagacgagtg | cccctacaca | 660 |
| ctctcagtcc | tatccactat | gggcaaggag | cctgaaggat | cccccagaac | tggctaaagc | 720 |
| cctcagtctc | ctcctccacc | ctgagcacct | tcacgcggca | gagtggccct | ggatgtcagc | 780 |
| ttcttgctcc | ccatggtctg | cacctggaca | ggtgctctca | ggtgtgtggg | tgggcaggtg | 840 |
| gcaggtccca | agagccaggt | gcaaagaatc | taggccagtg | cccacgagtg | ctgcagtgtc | 900 |
| tgtccccagc | atggtatcta | gggctccact | tgcctatcag | ctgtaatcgg | aggaggcttt | 960 |
| ccaggccagg | cctcccccag | gaaggctgca | ggcactgcgg | atcgtgcgcc | ctcacatgca | 1020 |
| ttattcctga | ggcccttctg | cagatgccat | cagggcagca | actctgatga | ggtattaggg | 1080 |
| cacagcacac | agggctaagc | caccctgtac | tgggcaagc  | gctacaggca | aaaaggacac | 1140 |
| caccgacggg | catttcattc | atcgctttta | tttttatata | tttttgagag | ggagcctcac | 1200 |
| tctgtcgccc | aggctggagt | gcagtggcgc | gatcttggct | cactgcaact | tctccctcct | 1260 |
| gggttcaagt | gattcctg   | cctcagcctc | ccgagtagct | gagattacag | gtgcccgcca | 1320 |
| ccatgcccag | ctaactttg  | tattttagta | gacatggggt | ttcaccatgt | tggtcaggct | 1380 |
| ggtctcgaac | tcccgacctc | aaatgatctg | cctacctcag | cctcccaaag | tgctgggatt | 1440 |
| acaggcatga | gccactgcac | ccggcccatt | catcactttt | aaatagcacc | ctctgaacaa | 1500 |
| agctccctgg | gccacatgac | cctaagggtt | accccatccc | accccaaccc | aggtctggca | 1560 |
| ggtcctcaga | acaggaaaag | ctgagcactg | cccaaggctg | cttgctgggc | cagtcagaga | 1620 |
| ggtctctgcc | ttccaggatc | agaagtacag | gctgaaagca | gccttgggcc | cgcctccctg | 1680 |
| ggaggctaca | gaggcttcag | agggttccct | gaactcaaaa | ccagatgtga | gacttgaatt | 1740 |
| tgacttaccc | ctggttcacc | tcccaaccaa | agcagggtc  | agctttggct | cctccaggaa | 1800 |
| ccaggaagct | tccaggtacc | ctgtggagcc | cctctgctc  | ctgaaaagtt | gccacctgtg | 1860 |
| cttggtggga | tgccaggtgg | tctcagattg | accctggggt | cagcggtgag | ggacaggaag | 1920 |
| cctacacgcgg | gatcaggatg | gggatggggc | ctcctgtccc | atggctctgc | agctatgagg | 1980 |
| cagctttcct | agggtgggtc | tcctggctgc | agctaagacc | aggcaacagg | attcagcaat | 2040 |
| gacagggctt | cttctactcc | agggctccct | cacctggtta | acagcaaaaa | agaaaataca | 2100 |

```
gttcctgcta gcaaggtcta tagaaaggag gtgaaggagt caggcctgca gctacctctc    2160
ctggacagga gctggtcagg ataacttgga cccttgcatg cggcaggccc acaggcacac    2220
agcatgaggc cactctctcc cccggggaa gggcttggtg aagaaaggat tcccctgaag     2280
cacaaagaaa gcacaggacc actgtgaaat ttcaagacaa ctttatccag acaggcgcct   2340
ctcaaataga acacagggaa gttaggcagc agttactaaa atacagtctc gccaaatgat   2400
ttacaacaga acacaacagg agcagggat ctgtgggtgg ggctgggctg ggccctctat    2460
ctcacagggc ctgagtcaag ccagcccgcc ctgcaaggca ggggctgacc tgcaagcgga   2520
gatctcactt cctcttaccc caaattcata cctccatttt cccgccccc atctctcccc    2580 agggtcctca agtgggaaag ggagaggtag catccctcgg atccaggccc actccactcc   2640
gtctccggca ccagtgggca ggctgagtct gggcctcaag gggccctggg cttagggtat   2700
ctatggcagt aggaaaatga catggacagg ctcttcaggg gtaggctaaa gtcctctggc   2760
cagcagtacc cagagaaaat gggcagcagc aggtaaacca gccaggaggt ggagtcctct   2820
gaacccacag cagaccccac cctcctgccc agcccctgcc cacattgggg gtcaggacca   2880
ctgagactct ggtcaggaca gtgggtgctc tcagcagtgt ggcaagctca gagcagagct   2940
cccaaggacc ataccacact ggttcaaaac ccataggtga caccatccca gcagaagctt   3000
ccatgggtgc tggatcccag ggctgcatcc tgagcacagg tgggcagact ggaacataac   3060
actaggaccc aagggatcca gaacatttta ggcccatctc ctgggctgct ccagcctgtt   3120
gccatgactt gggcagtgag tgggcctcct gccaggtggc agggcacagc ttagaccaaa   3180
cccttggcct cccccctctg cagctacctc tgaccaagaa ggaactagca agcctatgct   3240
ggcaagacca taggtggggt gctgggaatc ctcggggccg gctggcaccc actcctggtg   3300
ctcaagggag agacccactt gttcagatgc ataggcctca ggcggttcaa ggcagtctta   3360
gagccacaga gtcaaataaa aatcaatttt gagagaccac agcacctgct gctttgatcg   3420
tgatgttcaa ggcaagttgc aagtcaaggc aagtgtccca gaggccctgg gcagctgagt   3480
gcacctgtgt ttgatcttcc cctgatgatg gacactccca gctgaccatc caaacaccag   3540
gaaaacatcc ccctttcctg ggctcagttc ctagtctact tgctggtacg aacccaaccc   3600
acacactccc cgcccacaat gcagctcctt ccaaatcctc ccacaagcca cctttgtggg   3660
acttggaagc tgcttaggat gggccctgcc ctctgcggga agccaatcct agcagaaagg   3720
taagctaaac aacagtctca gaatctgaga cccagtgact gttcccccg cccccaggcct   3780 tgggcctgaa gtgggggcct gcctgtggcc tctgtggtgg gctcactccc acccccaaca   3840
gtggccccag gagaggcttt cccaagagtc ttcaaactcc acccacccca gccctagcat   3900
cagggactcc ccaccccca ctggagtgtt aatatcatta atgtacaaat aagatccaaa    3960
gatataccaa agatcgagaa acagctggct ccgacctccc tcccacagag ccttcccagg   4020
gttagctgaa aaagagccct ttggcatcta cagaagccag tcgagtttta tggtttcatt    4080
tgcccaaaaa taccctttg gggacctcaa attctttcca agaatcacta ccacacatat    4140
gaatttgaac attcgccacc cttccaccat ccatttctcg caggaacttc aaaataaaaa    4200
tggccagtct gccccactc tggctcctcg tctatgctct tctcttcttt tccagggct      4260 gcagttctga tgtgaatgat ggtgccattc cagcattggg cctctggcag gctgcatcac   4320
atgatggcac agcatgagtt ttgtttccgg gccttggaaa aaacaaaga ggagctgaga    4380 aggaggactg acgaagtaag ggaagcccca atcctggcag gcgtggcaga gggagctcca   4440
```

```
caggacacag ccaggcagag aaactagcac tagaacaggg tggggtgga ggccttgagg      4500 gaagctgtcc acaagcaatt cccatcacca agcacaaggc gggccccggc ttccaaaact      4560
agtctgggat ccttttcct ttcttttctc acaccccatt aatgctatca aaaagtgagt      4620
aaaattccta cagttaggcc aggtacaaac aaaggaccaa taatacaaat gggattggca      4680
gaatatctta actttgcccc actcctgtct tcacacaatg ctatctgacc accacggtgg      4740
tgtttcttcc tagaagatgg tcctgaggac aacagatgtg gttcccactt gggatgtggt      4800
ttgtggggac cactgttgcc accttctctc ttgctttctg gtcacagact atcttcctaa      4860
tcccacctag ccatctccct ccaatgtgca catgaaagca aatgtgtgtg gacagaccaa      4920
gtaaatttgt ccctatgact atccaaccat gggccaacag tgccatctcc acataggaag      4980
acatgagcac tgacctgaga gaaagcggca gtcagcagca cccatccttg tcaattaaat      5040
attttctgtc aaagggaaat taaaagctta agaacctctt caggaaggct gaattgcttg      5100
catcttaaag acttatgtct actcagcaga aagaggaata agattcaaca gtaaatctct      5160
ggtgatcaga acttgaacca gccttcctgg actgggagta ggagttcaga aatcagccag      5220
agcagcagag ggcagagcag aggcaggagt ggaacaaggc ctcggcccgc atcgactcca      5280
acggcgccca agtgaactgc ctccaaccac ctgggcctga ggcgctcacc ttaggctctt      5340
gccgcacaag gaatcatcca ccatgattca acagtctaag aaagacccgt tcatagtgga      5400
gagtgccaga agcagcaagc tgcgactgct ctctagagag aacacccagg aggcagcagg      5460
tgctgggtac tcacagtttt atagaaggct ttagactgtg ttcccagcac ctcggatttg      5520
gacaccaagt catctagctt ctcacctcgc tctaacagag actccatggt gttgtgctgg      5580 acaaaaaga aagagaatc cagctctgtt cagtacgtgc cctgacatga gcccctcata      5640
tttcagtcat gggggaaagt gccttacctg ggttcctctc caacacacac aaacttcacc      5700
tctaggtgtc gagactcggt ccaagaatag ttactgtcca agtggatgga acagaacctg      5760
gtgacattcc cgtgaaatct agaagatcta actgggatgt agcagacttc ccaaaaagct      5820
gtccccagca caggcttaga taaccagcac tccaggaaaa ctcatatata tatatacaca      5880
cacatttata tatacatttg tgtgtgtgtg tgtgtgtgca cgcacatgtg cgtgtgcatg      5940
gagctttgga aaaagagta gctgggcact atatgattgt actgggttgg agagtgaccc      6000
acaccgcacc ccccaacccc aaccgcatcc cagaaattaa catccccaga atctctgaat      6060
gtgaccatat ttagaaatag ggtcttggca gatgtaacta gttaggaaga ggtaatactg      6120
gattagggtg gcatctaatt ccatgactga tgtcctggta agaaacggaa acacacacac      6180
agaaggtcac gtgacggcag aggcagagcc tgaagtgatg cacctctaat ccaaggaatg      6240
ccaaggatgg ccagcagcca ccagaggctg gagagaggcc tgggacagac actcagagcc      6300
ccaaaagaca ccagccaggc ccacagagct atctgttaaa agcaaatatt tgagggtttc      6360
tgttgacagc agccacagga acaaaaggc ggtgggaaat ggctattgag cacttgatgt      6420
gaggcaagtc caaactgagc agcgctctga gtacagacac accagatttc agatgcaaac      6480
tcacacatgc ttcattagta agttttatac tgaaaaaaaa acaagtttta taccgattac      6540
atgttggaaa aattgtattt ggatatactg cgttaagtaa aatatataat taaattaaat      6600
tctacctatt ttccttttat cattttaaaa tatggctcct agaaaattct aagttacaca      6660
catgccccaa atatatacca gacagcacta tgacagaaca tgtcctgcct tctaaatggg      6720
ctatgtccta aatgtcatca ctacaaactc tgacttagga aatgaaaaca ctgacccat      6780 gggaaggggt ctagagatgg agacctcaca agagccagca gctctgctgc cagggccctc      6840
```

```
aggaagcagc agctcgcttc tctcctcaga tggccactgc tgcagcagct agatgcacac    6900
atgaagcgcc atagaacaag gagccagcaa gaatgtcctt catccctaca cacagctgag    6960
cgactcaaat ttttaacaca gaaagttaac tgattcagat atgcacacca atcatctaga    7020
ttttacaact gcagctagat gaggctgggt gaataggact catccactcc ccaccgtggg    7080
gagaggagaa acagcgggtg tcccaggtgt catggtactc agactaggac ttgagcaaca    7140
gaaagagatg gcttgaggag aaaacggaga aatgccacct aggtggtaag aaagctcaca    7200
aggtttcaaa agacacagat accatgagac tttcacatct atcgttcatt ccaaagccac    7260
gttatttgga gtgcagtcag cacacctgtg tttgaagccc ctgggatgct ttttataaaa    7320
tgcaggttcc caggctccat cgcaggccaa caactccaac cccaggagac gctgatgtac    7380
acactaaagc tatgcctgtg taaatggtaa agctttgtat gtgggtttca atccactcca    7440
ggtatctatc aactgctgag catggtataa actaggcact gtatcatgag caggatggaa    7500
agatgtccca gtgctcatac gctggtcagg agacatgta  aacaagcagt gacaaaactg    7560
tgacatctgg tcagaaaggc ccaaccttca ggcgcctgtg tgtgagctgg caagaaagg     7620 gtataagaga gaacagggcc cagtcaggag actgtgagtt agtttgcact ttatcctggg    7680
gcggatctga gagctgctga agggttctaa gttgtgcaga tcaatgacta ctctctggtg    7740
gacagactgg aggtgagcag gaggcaaggg gaccacttag aggcaaaggc tgtaagagaa    7800
aaacctgaga aaaacagata gctgcttaca ttccacttgt atgcaaaaat ttaaaaaaaa    7860
agagttgaag caacagttac aaatcaggag atttcagctc aaaatgcagg gttctggctc    7920
ttttcaaagg ggcctatgtg acaaccctgg gcccatattc cagaagctgc cctgtggtca    7980
gtgcacggtg cttcaatctg ttcaccttca atgcaaacgc tgcaagggga ggcacctgtg    8040
gggtgtggag gcacccgaaa ccctaacaaa ggcaccaggg tgggaatcca ggtcttcaga    8100
agccaaaccc taggaaccca gtaaatggtc agacaggcag tagccatgag gaagggagac    8160
ttgagggttc cactggttcc cagcttggtc ccctagaaac aatgggtgcc attaaccaag    8220
agaagggtat aggaaagaca gtctgatgcc cggggtgggg gaaggggtgg gcaatcccac    8280
ttgctggaga gtgccgtggt tactattata ttaaaacgag gatggatctg tgcatgcctg    8340
gccagtggaa atcgcacccc cgcctcagtt cttgggcttg ctctccatct tcctgcttac    8400
cagaatgatt ttggtctcat ctagttcggc ctgcacttta gtcatgggat cagcttctcg    8460
tgggttctag gaaagagtga aaaataataa agtcaggact ggagtggcta cctgcaaaca    8520
aaacctaaaa ctgaggaagc tggacaaact ttcacaggtt aaaaaccaca gcctgggccg    8580
ggcacagtgg ctcacgcctg taatcccagc attttgggag gatgaggcgg gtggatcacc    8640
agagatcaag agttcgagac cagcctgacc aacatggtga accgtctct  actaaaaata    8700 caaaaattag ccaggcgtgg tggcacatgc ctgtaatccc agctactcgg gaggctgagg    8760
caggagaatc gcttgaaccc aggaggtgca ggttgagtga gccgagattg cgccactgca    8820
ctccagcctg ggaaacagag tgagactcca actcaaaaaa caaaaaacaa aaaaaaaac    8880 ccacagcctg tttaacatgt aacagaaacc caaagcctgc ctagagcttg ggttccccgg    8940
tctgaacgta gattctctgt tttccaaaca gtaaggcttg agagaggaca ccagcatcag    9000
aagctgtcag aagtaattag accagaacta tcagggcagt tggcttttc  agtttcacat    9060 ggattctggg ccacatggtg tctgctgaag cttcctttaa ccctacctgg tatctactga    9120
ggtgaccatc cagggctggg taatggattg tagcagggga tcctactggc cagtctatcc    9180
```

-continued

| | |
|---|---|
| tgtcgacttg cttggagaat tcatctagta cctgcaagac aaaggagact caacaagcct | 9240 |
| cccactgtgc actcaccagt ggtctcaatg acagggcttc acccctgagc acctcaccct | 9300 |
| gaatgaggct ccttggcctt cacagcccag gaaggaggaa tgaggggggac atataatggc | 9360 |
| aacagagaaa atctaggcta aagttctttc caaatttta tcattaaaac atatcctaaa | 9420 |
| tattctgaga atcaaaagta tgcccagccc gagatgaacc tcacttgggg agtaataaag | 9480 |
| gtatttgaat tttaaactac agatttccag aaaaagggg cactggtcct ctaattttcc | 9540 |
| aaagcaattt tttaaaaaag agaattaggt ccctagatt taagaaacca ccagattcca | 9600 |
| tgtgtttgga ggtattttgg tgctctgggg tataggatga agcctctgac ttcaaagagt | 9660 |
| taatattagt aattagcacc gtacgcaaaa aaatttaaag aatgcttagg tgctaagctc | 9720 |
| tgtggtgcaa ctgactgaca tcaaggtaga gggatgcagc aactgcagga ggcaatgggg | 9780 |
| agagtgaagg cattcaagag ggagactcct tgagcagaag cacaggggc gagaacacaa | 9840 |
| ggcacagctg tctccgaggg tcccatccca gagaatagat gctatgactc agtggcctag | 9900 |
| acccagctca catgagggac agcaccgggg aggaaaccca tacagggatg ccaaattgtc | 9960 |
| tcttggggttg cagggaaggg ggctgaaaaa tgtgttgact ttggacacat catttcatcc | 10020 |
| cttatgtctc agggactgcc atcaacccct gtcccagtcc ataaatgtgc ccattcatca | 10080 |
| tccaagtcca ggagaggcaa ataaaaaact caccttctcc agcaaggtaa aggccacccg | 10140 |
| ggatgggtat tcattgtcag caatgaccac acctgcaaga ctatcattcc ggacgtagac | 10200 |
| gtggcacaga tagtctaagg agacaagaga tcagacacat ggatgctgac atgagggctt | 10260 |
| cagacttctt ttaatccccc caaatcaaag catccaatgt taggcaaat gaagccactc | 10320 |
| ggaagctcaa tagctctggg caagtcttgt ggagaggctt agcagcacag cccaatgggc | 10380 |
| cacacacagg agcttggccc aacgcctgct ttaggaccag taaatacca gaggcccagt | 10440 |
| atgcaaagcc agggcttaaa gaaacagcca gtggtgcaga aaacacaccc ttgacaacat | 10500 |
| ggccccagga gcatttccaa gtgtattcct taagctcggg tcaggccaag ctatatctta | 10560 |
| gggatctgga gcccttgggg ctctgtgctg ctcccaaact tagggaaccc tggacaagcc | 10620 |
| aagaggcctc tgctttctta aaaaatcttt tcagagcagc caaaagacag gaaattaccc | 10680 |
| cccagggcct cagtcttcca tattatagca acctgctggg tttgctccac tctggtgggt | 10740 |
| gactgggagt aggggggtta gtctagaaaa agattagcta ctgccagcta aggcctccag | 10800 |
| agcactgtgc taaaatcctc atatgattga aaggtacagt tgtacaggtc ttccgcaaaa | 10860 |
| tattcacaat ccacaggatt gttcatttcc atcactttga aaggattcag agttgataca | 10920 |
| gctaaccata tccccaagga aagagaaatg taaggattac agcttacaaa taagaacctt | 10980 |
| cttgtcctta aggatctgac ccagaagatt ccaatgctaa acaacagaaa aacaaataaa | 11040 |
| agaggaggga atgatggtga gccctgaaa tcagaaaaga gcagagataa atgagaacaa | 11100 |
| gaatgaggag gaggaagagg acaggggggtt gtcaccaatg ctctccagat tttgtatacc | 11160 |
| atccccaatt aagattcaaa catggggtca aagtgcatac cctccaaaga aactgagaac | 11220 |
| ctggtcagtg gaggaattgt ctttaagtaa taaacgtggg aagggcaggc acagtttgaa | 11280 |
| gaacagagca agaacactga aatatttgtg atgcgatttc acttctatga tgttaatagc | 11340 |
| acagagatcc cacataaagt gtatatagtc aatcctgcct gtatcataac tgacatttat | 11400 |
| atcatcaatt cagtaactct atgtcacgtg acttgaggtt agcataagtg tgagatgatc | 11460 |
| tttgtcccta cctgatgaaa ctcatgtaac tcttctccctga tctgtctgta taacatacac | 11520 |
| atctaaataa atgcctaaac ctgaattatc agaaagaaaa aatagttttt tcagattcct | 11580 |

```
gatcaaaaaa tctacgatgc acagaataca tatagtacct caacagtgct agctggaaat    11640 cctttttga ggggtctgca actctgaaga ggatagggaa gaatacgata tgaaggctgc    11700
ttactgctcc aaaagagtca gaccctaatc ttaaatgagt ctaagtttga gggcaatttt    11760
atctgggaag ctcagacttc aacagtgggc acagaattct gcataaatag gaaaaggaag    11820
aggtgggaaa gagagaacaa gctagaggag gagtagggtc ccagtagaaa ggagaaagct    11880
gggtgctatg tgaggtgagg catggcagcc aggccagcac acgcacagaa gttggagggt    11940
cttcttacct tgttctttga cagaagctct agtgcctttc gatgagcgct ccacaatcag    12000
ttgactcgtg aaggtcatga attcctgaac gctaagaaac acaaaatgta tttattgcct    12060
acttcttatc accttgtccc caacacagtg gaaagtgacc tctgggctta tacattaagt    12120
agacattgct tcttggtttc attcctttcc ctcccatccc tagtaacaaa cactctataa    12180
atgagcacaa atactgataa ttatgaatta tcatcaccat gaaagctcca tctgtttgct    12240
acctggctca ccaaaacagg tgaattttct gggggttttt tccacaggat acagtcaatt    12300
ttacattttg gtgaatgcat aatttggaat gcaatggaaa aacaagaggc aggtcctgct    12360
ctcaaggtcc caataacttc caagaagcag gacatttata agaactgcac tagaagaata    12420
gtgtgcaaaa actgtcaggc agaaatgcac aaccatttat ggctgtgtcc acatgacaga    12480
ccctcgcaat gccacataca cccatagtga gtgctggctc aggtctgctg gggctcgtcc    12540
acagaacgag cgcaagacac tctggatgga acaaaggaa aactgctcat ccaagacaaa    12600
gaagtgggaa atggctcata caaagggtga aaggagaag gtccatcatg ggctcaacag    12660
agagatctat ccagaacaga acagtcacag gagatggtac agccagagga agaggtgctg    12720
acaaggagcc tccaactgag gatgtgatat aaagggcaac cagggccatc aaagcagggt    12780
gctcaaatgg gagtctgcag caggctccag cagagccata taggtaactg aaggcctgac    12840
tctgggcctg tgtgctgtgc ctccacatta aaaaatcaa gatttgtgca acagttaaac    12900
gaggtaatac gtgtaaagca cttggaacaa tgcctgcaca cacagtatta cttgttaata    12960
tcttgaggga ctgaagtgat caaaataacc cctcagaaaa gaagacctca acaaggaag    13020 gctttgcagt aaacctagag acagcatttg agacacggct ataaagagac aaaggaagaa    13080
ctgcattgtg acagcatgta tacaaagacc aaaaaagctg ggaaactact ttttcaactt    13140
tggaatcggg taattatagg gcacaaagga cgtaagtaaa gcggtcttat aagaaaacaa    13200
gctcaggccg gacgtggtgg ctcaagcctg taatcctagc actttgggag gccaaggcag    13260
gcggatcact tgagctcagg agttcgagac cagcctggct aacatggtaa accccatct    13320 ctactaaaaa tacaaaaatt agccgggtgt ggtggtgcgc gcctgtaatc ccagctactt    13380
gggaggctga gcaggagaa tcacttgaac ccaggaggcg gaggttgcag tgagctgaca    13440
ctgtgccact gcactccagc ctgggtgaca gagcaagact ccatctaaaa taaaataaat    13500
aaataaataa atcagctggg acatgtgttg ttttaagaca tattagtaga gatgtccctt    13560
tagtgttgca gctgttagtc attggaaact agtgtgggca tcccaagcag gtgaggtata    13620
agtcctacaa gtgaaatctc tgagaatctt aagtactaat gggaaggaaa aaggaaaaag    13680
aatcagagcc aagttggcac caaaagttcc atctgagaaa agcaacaaca cagagcagtg    13740
aatgtaggcc atggtaaaga ctgcaaagac caagaaccc aagaaggagc taaaagataa    13800
tgcagcaatt ccgcttctgg gtaaatacca aaaaaatgcg agcagggtct tgaagagata    13860
tttgtacatc catgttcata gcagtatcat tcacaatggc tgaaatgtgg aagcaaccca    13920
```

```
ggtgtccact gacagatgaa cagataagca aaatgtggtg aataatacaa tggattattc   13980
agccttaaaa aggaaagaaa ttctgatata tgcaacaaga tgcatgagcc ttgaggacat   14040
tatgctacat gaaataagcc agacacacaa aaactatatg attccattta tctaaggtcg   14100
ccagaaaagt caaaatcaca gagacaaatt agaatggcag ttgccatggg ctgggggaga   14160
agggaatgtg tttaatagac acgaatttga taaaaaggag ttctggagac gattgacagt   14220
gatggctgca caacactatc aatctatttc atatcaatgc actcactaca cgcttaaaga   14280
tagtgaagat aaattttgtg taccatttta ccacaattaa aaatattttt ttaaaagaac   14340
tcaaagaagc agaaagtttc aacaaaataa cattttttt tttttacatc cagcaagtcc   14400
ttggcaaaga actctcatca agaaccagct gcactgaagc agggaaaaca gaatccaaac   14460
ggcagattcc atcagatttt gagacaagat gaccatagat accgaccatg tagggtcctc   14520
cttctttcgt gcctgagtca ccccaatccc tcccacgaat ggtctggaag tgtctgtgtt   14580
acttctaaca cgttccagca attaaagcgc cccagaaaca agtaaaagcc tgtaagccct   14640
acagatccca tgcttcattt gcatcttccg tgtggaatcc ttttgtacca ctagtgtcca   14700
actaaaaagc gttaaacctg ctttcagtt ctagctggtt gtgatataac ctcttggtac   14760
ctcagtgact tcacccatta aaacaaaca aaaaaaagta tatcactatc tctcatacag   14820
aattgttggg aagccccgca agaaaatcaa aatatggctc tcaagatgcg gcacccaagc   14880
tcccagagtc agaatcactg ggtgggaagt gttggtctaa aatataaata ccgaggcctc   14940
aatctactaa ttcagaacat cttggcatga agcttggaaa tctgcactac ttcacagtct   15000
ccttaaaatt tttacacgac agaaatttga aaaacactga gtagagaact atattctaga   15060
atggtataag ctcttaaaga gctaatgttg gttcctcaaa ggtagagtcc acggccagat   15120
tccattatag gagaccaagc ccggacagca gaccccgggc cctccccacc ccgccccgcc   15180
tctgactcgg acaccagcct tctcagaccc cgggcactcg gccacccgc cctgccccta   15240 cccttggcct cctccaccct cccctcatcc ctccgccgac cccaggccca ctccgactcg   15300 gaccccacc ccagtcctct ccgcccgacc gccacggccc accagcctgt gccgctcacc   15360
tggatctctg gaaaaagctg aaggaagaca catcgtatgc ggctttgagc agcaccacct   15420
tggcctcgcc tttgtagagg acgctgaggc tgtacagctt catggctccg cgccctcagg   15480
ccgcccgcct gcccagctgc gggacccgtt ctcagggagc agcgcggccg ccgcccctcg   15540
ggaccgccgc cgcctaccgg cctctcagca gccggctgct gacggggcca ccgccggctt   15600
cctcctcctg gctcgcaatc cacttccgga tccggtcagc ctggttgagg gttctcatac   15660
tccggatgca gaaatgtgag cccggaagta caatgcagcg aggggcggga tgccacgcct   15720
cgcgtaagct tggcccctcc ctgctcgcca ggtggagtcg ggcgcgcggc gggataccgt   15780
actgtcttgt gctgggtggt gctgggcctc ccacagcggc ctgaacccctt cttttttttt   15840 tttttctttt ctttcttttt ttaaagtaag catttttttt attattatac tttaagttt   15900 agggtacatg tgcacaacgt gcaggtttgt tacatatgta tacatgtgcc atgttggtgt   15960
gctgcaccca ttaactcgtc atttagcatt aagtatatct cctaatgcta tccctccccc   16020 ctcccccac cccacaacag tccccggtgt gtgatgttcg ccttcctgtg tccatgtgtt   16080
cttattgttc aattcccacc tatgagtgag aacatgcggt gtttggtttt ttgtccttgc   16140
aatagtttgc tgagaatgat ggtttccagc ttcatccatg tccctacaaa ggacatgaac   16200 tcatcattt ttatggctgc atagtattcc atggtgtata tgtgccacat tttaggagga   16260
gcttgtacca ttccttctga aactattcca atcaaaagaa aaagagagaa tcctccctaa   16320
```

```
ctcattttat gaggccagca tcatcctgat accaaagggt ggcagagaga gacacaacaa    16380
aaaaagaatt ttagaccaat atccttgatg aacattgaag caaaaatcct cagtaaaata    16440
ctggcaaacc gaatccagca acacatcaaa aagcttatcc accatgatca agtgggcttc    16500
atccctggga tgcaaggctg gttcaacata cgaaaatcag taaacgtaat ccagcatata    16560
aacagaacca agacaaaaa ccacatgatt atctcaatag atgcagaaaa ggcctttgac     16620
aaaattcaac aaccctcatg ctaaaaactc tcaataaatt aggtattgat gggacgtatc    16680
tcaaaataat aagagctatc tatgacaaac ccacagccaa tatcatactg aatggacaaa    16740
aactggaagc attcccttg aaaactggca caagactggg atgccctctc tcaccactcc     16800
ttttcaacat agtgttggaa gttctggcca gggcaatcag gtaggagaag gaaataaagg    16860
gtattcaatt aagaaaagag gaagtcaaat tgtccctgtt tgcagatgac atgattgtat    16920
atctagaaaa ccccatcgtc tcagcccaaa atctccttaa gctgataagc aacttcagca    16980
aagtctcagg atacaaaatc aatgtgcaaa aatcacaagc agtcttatac accaataaca    17040
gacagagagc caaatcatga gtgaactccc attcacaatt gcttcaaaga gaataaaata    17100
cctaggaatc caacttacaa gggatgtgaa ggacctcttc aaggagaact acaaacgact    17160
gctcaatgaa ataaaagagg atacaaacaa atggaagaac attccatgct catgggtagg    17220
aagaatcagt atcgtgaaaa tggccatact gcccaaggta atttatagat tcaatgccat    17280
ccctatcaag ctaccaatga ctttcttcac agaattggaa aaaactaaag ttcatatgga    17340
accaaaaaag agcccgcatt gccaagtcaa tcctaagcca aaagaacaaa gctggaggca    17400
tcacactacc tgacttctaa ctatactaca aggctacagt aaccaaaaca gcatgctact    17460
ggtaccaaaa cagagatata gagcaatgga acagaacaga gccctcagaa ataatgccgc    17520
atatctacaa gcatctgatc tttgacaaac ctgacaaaaa caagcaatgg ggaaaggatt    17580
ccctatttaa taaatggtgc tgggaaaact ggctagccat atgtagaaag ctgaaactgg    17640
atccctccct tacaccttat acaaaaatta attcaagatg gattaaagac ttacatgtta    17700
gacctaaaac cataaaaacc ctagaagaaa acctaggcaa taccattcag gacataggca    17760
tgggcaagga cttcatgtct aaaacaccaa aagcaatggc aacaaaagcc aaaattgaca    17820
aatgggatct aattaaacta aagagcttct gcacagcaaa agaaactacc atcagagtga    17880
acaggcaacc tacagaatgg gagaaaattt ttgcaaccta ctcatctgac aaagggctaa    17940
tatccagaat ctacaatgaa ctcaaacaaa tttacaagaa aaaacaaac aaccccatca     18000 acaaatgggc gaaggatatg aacagacact tctcaaaaga agacatttat gtagccaaaa    18060
aacacatgaa aaaatgctca tcatcactgg ccatcagaga aatgcaaatc aaaaccacaa    18120
tgagatacca tctcacacca gttagaatgg tgatcattaa aaagtcagga aacaacaggt    18180
gctggagagg atgtggagaa ataggaacac ttttacactg ttcgtgggac tgtaaactag    18240
ttcaaccatt gtggaagtca gtgtggcgat tcctcaggga tctagaactg gaaataccat    18300
ttgacccagc catcccatta ctaggtatat acccaaagga ttataaatca tgctgctata    18360
aggacacatg cacacgtatg tttattgtgg cactgttcac aatagcaaag acttggaacc    18420
aacccaaatg aacccttctt tttgcttgcg ttgttgaaag aaggcaagtc tatggatagg    18480
aatgagtgag gcacagctcc ctgaggatgc catatcttgc ccgtttcttg tgtattaagt    18540
gacatcacgt gttaccaaac taaaccggct gcatttgcct gcgcacaaca taaaccaaa     18600 cacccaagca ttggattttt gtagcaagaa agatgtattg ccaagcagcc ttgcaagggg    18660
```

```
acagaagacg ggctcaaatc tgtctcccaa tacttgcttc gcagcagtag atttaaggga    18720
gagattttgg aagtggagtt tcgggctgga cggtgattgg ctgaaacgaa gaagtgttta    18780
gaaaatctct tggtcatgag ctgttgcttc ttcatgctgc ttcaagggtc acatgcagat    18840
tcaggaggtg gtataaaaca agctgtggga atttgggctg tgacatcaaa gggccgctcc    18900
tcgggctagt aagtctattt tgcacaggct ccagtcagcc atattggttc caacctgttc    18960
cagcaagttg tataagcaga ggggattata gcaaactgtt tccttatcgg ctgccctgca    19020
agacaagctc aagatttctg ttagttacca gtttctttaa ccctgtcggg cacagtttca    19080
catgtaatca gaaaggaact tgcaagacac atacaactga agaaacttg gtctttggaa     19140
gttgtcagta aggtcacaaa gttgtgatgc tagaagcagc cgtatctgag attatgggaa    19200
agagatgata tattggaaaa acaacagcat cactttaaac attactctaa atcaaggttt    19260
ctcaaccttg gcactattga cattttgggt tagatagttc tttcttgttg ggagactgcc    19320
ctgtacattg tgtaggcagc atctcaggcc tttgtagaaa tgtcagtacc aacccacccc    19380
ctccccactg cacaatcaaa aacgtcaaaa tgtcctttgg gagcagtagt tttgagaaac    19440
attgctttgc agatatatat gtttgtttgt ttgttttgct ttgtgacagg gtcttactct    19500
gttgcccagg cagaagtgca atggtgtgat cccactcact gcaacctctg cctcccaggt    19560
tcaagcgatt ctcatgcctc agcctcccga gtagctggga ttacaggaat gcatccatac    19620
acgcggctaa ttttttgtatt tttaatagag atgggatttc accatgttgg ccaggctggt    19680
ctgaaactcc tggcctcatg tgatccaccc acctcgacct cccaaattgc tgggattaca    19740
agcttaagcc actgcgccca gctgagaaac attgctttaa ataatctgtg gtgaaaggaa    19800
gttcccacca cctgcccact cactcagtac ctctgtcacc aaccctcttc cctgggtgtt    19860
tccaagtaca gagggtggaa agggcttttc cacatttccc ctgttttggt agtaaacatt    19920
aggaacagcc attggccgtg gctaggctca gccacccaca gatatggaca cagtagtctg    19980
acaagctggg ttgctgggtg ctatcagtcc aggctcaact gcttgcactg acaccatttc    20040
cctataggag gcaggtgaga gccatttctg aggaaagtct ctggagcccc tcttccttcc    20100
actgaaagtt gtgcaaaaag atcaggaaga cagcgcttgg atggaataaa tttcagtgta    20160
tccacttgac acattatagt ggctgtccca agtttacct tatgccaagt actttccatg     20220
tgccacatca tttaatcctc acaaaaacag gggaaaatat tattgccacc ctacagacat    20280
agagactgag attcaattta aggagatggt tggtaaggga cagagttggg gttcagatgt    20340
caacagtgaa atgcttaaca aactgtcatg cagcccactc ctggcaactc ttcctgctcc    20400
tctctggcct cactcagcct ctactgttcc aggaagcctc attcatagtc atgtggttgc    20460
agacttccca agctcactgt gttaccaaaa agcaagacct gccttctgct gcatcgcccc    20520
agctgtcacc caacttggat tcagtcccag cactgacaca tcacaaaatc acaaaagtga    20580
gcaaaccatt acctccctga gtctccttt gtttttatct ataaaactag aaaaatattc      20640
tttccatagg aatgttgttg gaaataataa aacattatat tacaagctct agtcattgtt    20700
gatgtttaac aggtaacagt gataattatt tgtcttctca ttaatgaaga aaggattat     20760
taatcataga gggtggaagg catctatggg aagtagagat ttgaagatag gctaaaaccc    20820
aagtaaggcc tctagattag ataatagtat tgtatctatt ttaatttcct gctttccatc    20880
actgtgccat ggttatataa gagaagtctt tgtttatagg aaatatacac aagaatttag    20940
aagtaaaggg acattgtgtc tgcaacttac tcttacaggg tgtgtgtgtg tgtgtgtgtg    21000
tgtgtgtgtg agagagagag agagacagag agagagagag acagagagaa agagaatgat    21060
```

```
aaagcaaata caggaatcag gatgaagcgt atctgtttgt ttgttttgct ttgtgatagg   21120
gtcttgctct gttgcccagg caggagtgca atggtgtgat cccgctcact gcaacctctg   21180
cctcccaggt tcaagcgatt ctcatgcttg tattgttctt gcacctgttc tgcaagtaca   21240
acattgtggg aatggaaaat gcaggaaatg ggcagtaagg ctatgaacga agcccgcaca   21300
ggagtgtggg tagcagagtt ctctagtcca ggctcccacc tgaggtgctg ggacctagaa   21360
gaaaagcctc tctgcagaca gaactggagt taacgctgtc cacgataaat ggcccaggcc   21420
ctgttaagtt tgccccattg agcaaaacaa gtacccaccc gcctttgcag ccttgcctag   21480
ctcacataag gtgccagccc ttgctgtaca gcagaacctt tggggagctg acaaaagcc    21540 tatcaaggag catacccccca ggaagcccag tccaggtggg gagcccagcc acacaatggc   21600
ccttgccccc acacctcctc attcagtcag ctaaggccat ggcagctgag ctgcctccac   21660
agctcatata ggaaaagggt gtggaaaggg gccaccaatg tggtcaggcc tccatggcct   21720
gagtaggtca ccaagcctca ggtgcacaga cttgatgtca tcaatcaggg tctgtcagca   21780
cacctagccc tcaggaacac tgctcccac  tgcaacccca caccaaggca tcctgggctc   21840
cctctgggtt ctccaggccc cagggaagac agacagagtc tgccaccaaa ggtttgagct   21900
ctgccactgg ctacgaagca atagggggatg tcagagcaag ggaggaacag gacaggagta   21960
tacgtgggca ggaagggatt acagccaagg aagacaggag gcaggtgccc tgattttgag   22020
gctgtgcccc agcaggggct tcccagaagc tgtatttgtc ctaagacacc cctctgcagc   22080 tgagggggcta gagatggata tgtagctgtg ttaggccatt cttgcattgc tataaagaaa   22140
tacctgagac caggtaattt ataaagaaaa gaggtttcat tggttcacag ttctgctggc   22200
tttgcaagag gcatggtgct ggcatctgct cagcctttga ggaggcctca ggaaacttac   22260
agtcatggcg gaaggcaaag gggaagcagg cacatcacac agtggaagca ggagtgagag   22320
agagagaggc actgggaggt gccacacttt taaacaacca gatctcgtgt gaactcagag   22380
caagagctga ctcatcacca aggggatggc ccaagccatt catgagggat ccaccccccat   22440 gactcagaca cctcccacca ggccccacct ccaatattgg ggattacaat tcagatgaga   22500
tttggtgggg acacatatcc aaaccatatc agttatcagt agccatactg gatgaatgcc   22560
aggaacttag aattaggaca catggtcatt taggcaagtg gcttgtcctg tcaatggtac   22620
cctgatagtc gtggggttgc cccgtacaaa aagcgagagg aagtctacag agctgtcaaa   22680
gaggggcagg tggaaaggcc tgcagaggag tccctgctc  cacaaccagg cgtgcacctc   22740
ccacatcctc ggggctgtag gccccacatg agagcagaaa gaaggatgca gaggaaggcc   22800
aagaacacaa ggtgtgccct tggaaaggct gggcacacca aacacaacct aataaacaac   22860
agcaatgagc acacagggaa agtactcaca gggaaaccat catgaactag aggctgatcc   22920
cacaccctgc cacatggggc cccaggcccc agcctatcaa ccagtggtcc ttattgccac   22980
agcgattggt ctttggatag gcacctgatg caagcttcag ccaatcaaca ggccactcag   23040
ctggccatca gtaggccatc caatcagagc aaagcccagg actttcttcg actcttaaga   23100
aaagagaagc aaagtaactg gcacagattg gagaggatca aggaacccg  agctggatac   23160 atacaaactt tgggttaaca tggatgatta aatacatatg tttatgtgaa ccacctccca   23220
aatatgctcc actataatga cacaagacaa agggcagggg gagaccaatt gcaaggtggc   23280
gcaaatgaga gatgctacca agggtggcgg gggagagagg ggagcagttg tcaagttagg   23340
aggcaacagg ctgagggaca gggaccagca gacggggagg gaggggctga agcagaagtg   23400
```

```
tccagtgtct ggagggatgg ggccagaaag gcaaggggca tcctgaagaa gctatacctg   23460
gggagggcag ctctctcccc acctgctccc caattcatca gccaggaatg ccccatccac   23520
cccaccccag ggaggaggac agaggacttt cgtttgggag cattgaatgg ttcagagatt   23580
ctgcaactct gcggtcccca actaaactgc tcattgtttc aagcagtccc tgttgggtaa   23640
atgtccccca ttgtaaccgg actcggattc caccgcttga aagccaaata caagaggaga   23700
ggtttggtgg gaggaaaagt ggttttaact agagccagca aaccaagaag atggtgaatt   23760
gttgttttaa agcattcaat tatctcaaat tttaaaattt atcataggat tctgaaagga   23820
aaacttggta tgggacatac gtgggagcag tgcagggtac agggtctatg tgtcttgatc   23880
caatggctgt cttgagtatc acctatcctg aggtctggtt ggtgttatct ttccttcggc   23940
cagatggtgg tgggtgaatt gtttcgactc cccctaagtt ggaggattcc gcagggttc    24000 cgtgtctggt ttttgtttca agattagccc ctggaattcc caaataagca tagagttaga   24060
taagcgggca tggtgcaaag gagtgtctag tgggaaaggg agagaagcag agtttcaaag   24120
tacatttcaa ggttacattt taagactaaa gaaaaagcct taaaatgcat tttaaagct    24180 gatttaatgc ttggctacac taggctgtgg ccagtgtgca gtgtggctgc tcttggatca   24240
ggtgatgttt catcagctgt gtccaggag ggcagggcca tgtggcagaa cctgggacct    24300
ctgtgtgagg gactaccttg ccccctgtcc ttagcaggaa gctatggtaa ggaacccta    24360 gggagacatt aaattgggga gaccgtccct gccaatcctt taacctcccc agcctcagcg   24420
acctcagttg gaaagtggtg gtaataatac taccactgac caggtgtggt ggccagacat   24480
tccacacttt ggcttcagcc gctccctccc cactctactg taatcccagc actttgggag   24540
gaagaggtag gcggaacctg aggtctggag ttgagaccag cctggtcaac atggtgaaac   24600
cccatatcta ctaaaaagaa agtacaaaaa attagccagg tgcagtggca cacgtgtgtg   24660
gtcccagcta ctcgtgggtc tgaggcatga aaattgtttg agcctgggag gcagaggttc   24720
cattgagtgg agatcgagcc actgcactcc agcctgggtg atagaacgag attctgtctc   24780
aaaaaaataa aaataaaata ataataataa taccactgcc tgccacacta agattgtctg   24840
attagatgac agaatgaatg caaaagtact ttgtgaatca taaatgtttt catcaatatt   24900
agttataatg acaattgctc cttctcctaa taaatgtatt gcctttcttt aggaataaat   24960
ataacaagaa atgtgtaaga tatatatgag aaaaataata aaattcacct gaaggacata   25020
aaagaagacc aaaataaatg aaacaacaca tacttctaga tgagaaaact caatattata   25080
aagaggttag ttctctaaaa tgaatcccta aacccacaaa gtcaatgtat ttccaatgaa   25140
attgtcaaca gcattatttt ccgaagtggg atgagtagtg ctaagattta taagaaagcc   25200
aacattccag agcagtgggg aagggattgc ttcaccacca aatagccata ttagagattc   25260
ccttgcacca tacccaaacc accatctccc aggacccggg agagcagaaa agaggaatga   25320
gaagaaaggc gaggatgtga ggtgtgccct cataatggcg gtgcacgcag cacaagcaat   25380
tgcagaaaga ctaaagtact gaacaaatag aaaacttgga aaaatattag aaggaaatgt   25440
gggagaacat tttttgcaatt tggggattgg aaacggtttt cttaacaaga tataaaaacc   25500
ccaaaacaag aaaacaaagg ttgaaattca taaaaactag atacttctgt atgatgaaag   25560
acacgattaa tcaagttgtt aagtttagca atagactagg ggagatatca tagtatattt   25620
aacagacaaa ggattaatag atactacaga tgaaatataa aatagtttct ccaagtccat   25680
aggcagaaga taatccaata gcaacatagt taagtaatgt aaacaaatca tccttagaag   25740
aagaaatgca atcaccaaga aacacatgaa aaggtgtcca gcattttgca attcaagcaa   25800
```

```
caatgaggtg acagatcggc aaaaaactca taaagattta tcatctgaag gattggccaa   25860
gataaagcca aacttctcgt gttggcagaa gaaactggtg aagccatgtg aagaggccac   25920
gtggtcctgc ctaccaagat gtaaaatgtg tacagcattt gaactagcaa ttcagcctcc   25980
aggagccatc cagaagaaac actgacacac acttagactc cggtgaaatt caaggacttc   26040
tgccacagcc tgcttcgtaa tagtgaaaat ctgaaactgc ctcaatgacc gtcaatagga   26100
agttgatttt aaagtgttac agcacatctg tctggagaga tcgcactggc cactcctcct   26160
caccccctct gctggacctc tgagcgtagg tggcctggag ctgggtcctg agccctcttt   26220
ggtctatacc gacactaccc aatatggtag ccaccagtca cgctggacac ttgaaaagtg   26280
gccgatcctg actgagaagg gccacgagtg ggaaaaacac accagacctc agtgacttag   26340
gcagaagtat gttttgttcc agactattga ctgagcccgc agctgagttg gctccagcac   26400
cctggccccc tgctccatcc actcactggg actccccact gcacagggca acctctccag   26460
gggcacttgg gctgcgaagg ggagagtggg tggcatccca ggctgaagct tcctgagcag   26520
ggccagagga ggagccagtc cctgtgggcc tctgttctga cagtgtcaac ctcagccagg   26580
cttgtgtggg ccaggtgtac tgttctggtt cagatttcaa ggagatagtc agggcaggcc   26640
gcgccaaagc cctccgatgg gctcccctac tgcctggcag acctgtccag ctttggactc   26700
tggccctgcg acctggaagt caggctgcca agaggtccag gcagtggcct ccactgtgga   26760
gggtctctgg agagtttaca gccctagata ggggggttag ggatgtgaga tggtcccagg   26820
ggcctgctcc tgagccacgc caagctgcct gctcccttc ctctgcttcc agactcacgg   26880
gatcctctgc tcatcagaac aggagtgtgg gagaccctga cactgccc caggatctga   26940 acaggtggca aaggcttaac aggctagcgg tcactgtagt gacaaggcga ttgagtggtc   27000
accatggtga tggggatgga ggctcttgc caccagtccc agttttatgc atggcagctc   27060
taatgacagg atggtcagcc ctgctgaggc cactcctggt caccatgaca accacaggcc   27120
ctctcaggag cacagtaagc cctggcagga gaatccccca ctccacacct ggctggagca   27180
ggaaatgccg agcggcgcct gagccccagg gaagcaggct aggatgtgag agacacagtc   27240
acctgcagcc taattactca aaagctgtcc ccaggtcaca gaagggagag gacatttccc   27300
actgaatctg tctgaaggac actaagcccc acagctcaac acaaccagga gagaaagcgc   27360
tgaggacgcc acccaagcgc ccagcaatgg ccctgcctgg agaacatcca ggctcagtga   27420
ggaagggtcc agaagggaat gcttgccgac tcgttggaga acaatgaaaa ggaggaaact   27480
gtgactgaac ctcaaacccc aaaccagccc gaggagaacc acattctccc agggacccag   27540
ggcgggccgt gacccctgcg gcggagaagc cttggatatt ccacttcag aagcctactg   27600 gggaaggctg aggggtccca gctccccacg ctggctgctg tgcagatgct ggacgacaga   27660
gccaggatgg aggccgccaa gaaggagaag gtatctcgcc ctccattggg cattctggga   27720
gtgtttgctt gcctgtcccc aacattccat ggtttgtttg agcctcagaa tctgatttta   27780
tgcacaggct ctttgagaag ggtcttgcca ggggtgcctt ctggggcagg aaggccccta   27840
ctgcctggca gacccatcca gctttggact ctggtcctgc gacccggaag tcaggctgcc   27900
aagaggtcca ggcagtggcc tccactgggg aggggctctg gagagtttag agccctagat   27960 gtggggggtta gggacatgag gtcttgtgga caaagcccac tacctgattt tgagacaaca   28020
ctcactagac atggtgacaa gtcaaagatg ccttgcctcc taccaggaat cacttcgcag   28080
ggagcccgag ggctgctgtg gcctgctgag gagtgcaggg cagttacttt ttccaaaaac   28140
```

```
aaagagaaat ccaggcatgc tctgagccag ccctgagccc agcagtgagc aaggagagag  28200
ctggagacag gggactttgc tgtgaaacac tgggggaat gtgcctgcat caccccagct  28260
gggggcccag gcagagtggg ggagaagggg taagtgggca gagccagtca ctttgggcat  28320
gcttccctct cgcctctgtg tgaaatgacc aggtcagcat aaaccccggg ctggctgtgc  28380
ttctggcaga gctaatgatg ttaggaggaa acaaccaac ccaagtgaga gggtgcgcag  28440
ccagacagct ggaccggccg aggccccaac caagtcccag atctgcctgt cactggtgct  28500
atggcagcaa tttggatgag aaatcctgcc caaagggccc cttcaggcca cccggggaga  28560
aggaagcggc tgtctttggc atgaccagaa agatggctcg gagctaggga gaggtggaca  28620
tgtgggctgt ggagatctgg cactttcccc aaacaaggag agaaagcata gtgtgcctat  28680
gtgtgaatgt gctatgtgtg catgtttgtg cctgtgcata cctgcatgtg tacatgcatg  28740
tgcacatatg tgtgcacagg gaatcacttt aataaaggcc acagcagagc tgtccctgag  28800 cccccttgcat tcacagtggc atgtgagtga accaccttct taggctgggc atccagtctc  28860
agactctggg gctgcccatg ccccatcctt tatctgctcc acgtgtgagg ggttgctggt  28920
cctgaccagg gccagctgtg aaccccagaa tcctgggaag tcactgacat tcttgtcagg  28980
gccaagagtg gagcaaggca atgcctcggg cacaaacttt aagggtcac cagaaacatc  29040 aatcatcaag atatatgcta ttttaaataa tcaaaatgaa tgcaaaaaaa atttatgatg  29100
gacaacatac caaattctaa acaaaggcag gatgagtatc actggcttct gcacttttct  29160
ccacccagtc tacccctctt ctagtgcctg gatcgcaggg tgccaaggcc tggatgaggg  29220
aagcgtggag ctgcaatggc cactcctgtc tgcctgttct ggctgcacag aggactcagt  29280
ccttgtcttg ggggaaccta tcttggtttt agggtcatcc taaggatctg atgttttcca  29340
agtgagctgc ctgtccaggc ccacccaggt tcagtccagt cctgtgtctc tgggaagtgc  29400
tgcccctacc ccaagccagt gtttgacctt ggagcaatga gcaatgccct ccttccactt  29460
tcaaagttgt ccccaagacg tcagctgtgg ttgtctctgt gcagacaccg aggaggaact  29520
gtcttctttc tccttttggt tgctttggag gaaagtaaag tgttgctggt ttccctcttt  29580 ctacttctttt gattgagagc agccgtcttg ccggtaccaa ccttccagat cttacctgtg  29640
gttgcaggag cctgtggcct cagtcctgtg cccagtgact tctccatgtg gatgtcagct  29700
ccttaggggc aagcctgatt ccactgacac tactcccacc cctcataagc ccttccttac  29760
cagctgcagt tgcctggtac cccaccatcg ctgactcatt cctttggcat caaggttcat  29820
cccttactgg gccaccactt ctgggtggcc tgaaataggg ccctgggcat ccctcttggg  29880
gaccttttgg tctatatttt cactctcacc tcactaagga cagatgagta aatctggtta  29940
actttgcctg atagatttgg tgacctttt tcaggaagga gcctggaaag atgagattca  30000
ggtgtattgg tcagcttaga ctgccataag agaataccat ccactgatgg cttagaaaca  30060
acagaaatct atttctcact attctagagg ctggacgtcc aagatcagat gccagcatgg  30120
tcaggttgca ggggggctc tcttcctgac ttgcagaccg ccaccttctt gctgtgtcct  30180
cacatcgtgg agagagagtg aaaacaagct ctctggtgtc tcttcttata agaatgctaa  30240
tcctatgatg ggggctcccc ctccttacct catctaaacc taattatctc ccaaaggtct  30300
catctccaga taccatcaca ctggggttag ggctttgaca tatgaatctg ggggacaca  30360 attcaatctg taacaccagg agggcatgcc gggaggaact gaccttcctc cctccagctg  30420
ccctggacac ctttgcccca ttgaaggagc aggctcagaa gtggaatgag gatgaataa  30480 ggtgcactcc atcatgctta cccacatccc tggcaggaat tgtcctgggc cccagcagga  30540
```

```
gagatgcccc cccatactgc catggcacct gctctgagac aggtgtgcag agtgcaaagc   30600
tccaggtggc ccccaagcag gtgtgctggg aggaggggcc cgtgtgggag gagcaggcag   30660
cgccaaggcc tagcggagca gtgacaggtc cctgacttca gggaatgggc acgctgtggg   30720
caggcagctg gtgtgggggt gagggctggg gctgcatctg tgggaccagg gctgggccat   30780
ccatcatatg ccgtgtcaca accccagtgc ccctgctgta gccaggacag gaggctgggc   30840
caggctggga ggtgacaaga gtgggggctg tccccaggag aagcactctg ctgcctgtgc   30900
ccaggcctct ggggatgagg acccctcaga aggagtagct atgtctagga agccccaggg   30960
caggagcaag ccaaagggga catcattagt gagatccagg ggatcagtgg gccacagaag   31020
ccccagcgtg agccctctg actgatgcag ctaggcccac acctgcacct gcccacagca   31080 agaccccag gaggagaggg gacagatgga gagaggcaca aagtgcccct ggcctctgcc   31140
ttgaagccac cccaaggcaa gagagatttg agccctgtt tagtgacctc caggggaaca   31200
ttctggccca tctgatgtgg gaagcccctt gtggagtctg tcattcctca gctgagccag   31260
gcctttggag gcagcccagg catgtcccct gtgtgctcct atccctgtgt tgggacacct   31320
ggcccagccc ctccttctgc ctttctcttc ccttcccttc tcaggagtgg acacttcctc   31380
ctttagcccc ctcacagctg tgtgaacttc tctgtatctc tctctttctg tctctttctc   31440
cccctctctc tctgtctcat tgtctctctg tgtgtctgtc tgtagtattc tctctctgtc   31500
tctgtcactc tgtctctctc tctctctgtg tctacctttc tgtatttcgc tttgtttctt   31560
tttctctgtg tgtgtgtgtg tgtatctgtt tttctcactc tctctctgtg tctatctttc   31620
tgtatttcgc tttgtttctt tttctgtgtg tgtgtgtgtg tatatctgtt tttctcactc   31680
tctcaatctc tctctctctt tctgtctctc ttttgctggc ctgagcaaag agggagcccc   31740
atcctgatgc tacataaccg tgaaccagca cagacagaat tgtaggaaag tcctgcaagt   31800
agaaggatag aaggatgagg gaagaaacgc catgtgagtc atgacagatc cctttccagg   31860
agccactgac tcaccctgcc tcctgccctc ccactgtgac actattactc acagacaggc   31920
ccggattaaa cctatgttcc aggtgccctg tggttcccac agtgtggctc cctgggtctg   31980
gcctcaggct ccacaggtgc ccagccctgc caaagtctcc agagcagctg tccagctggg   32040
gagctgcggg gccccttcac agagcgcatg ggaagaagtt ccatcctaca cattacatcg   32100
agagggacgt gcctgagaag gggagctgga gcccgtgcag cccctgctt gcgtgcagaa   32160 catagtgtac cctgagcatg ccatgaaaaa cacaaacgca caaagttgta aagaaaaaag   32220
aaatgacagg tggctgtaaa atcagttata gcccacgaga ggcccactaa tgagtggtga   32280
tttcagctga ttacaaagaa atgatggtgt ttctgtaatg aactaaacat gcactcgtgc   32340
gtgcacacac gcgcacgtat agtcacataa ctgaccagcc ctatgcatca cttgttaatt   32400
acttagtaac tgtaacaata atagtttcca ataagtgagc cttagtctct gcgcaagggt   32460
cagtttattg agcacacggg ggccttgcag tgggggcagg tgatctgctc ctgggagccg   32520
ccagcctctc ctctcctgct cttcatcttc ctccgtggtg ggaaattgtc tcactgcttc   32580
tacacctgag gctgaacatc tccctttatt tcagtctgaa acacatgtaa aaatatactg   32640
gaatgaatta aggttgcaat tattgatatc aggcagtgag tacatcaggg tttattatac   32700
tatctccttt acttacttcg aagttctcta ttaccaaaaa attaaaaact ataaagaaa   32760 gaaaaaggaa atgaggctag attcaacaca gattactctt accaaccct tcgtagtccc   32820 aggagtcccc taacacaagc acttgtgacc tggagtgata ttcacagcat tccttacctg   32880
```

```
gcaatacctg agtattagcc cccccagtgg gatctttgtt gtagacaacc agcaactatc   32940
agcccagcca ataaacaagt aggaaagggg agtgctggag aggccaagaa gtgggatttt   33000
ccatgctcct gggctgtgat ccagagggca cggctgtgag gctgatctca atgaacactc   33060
tgtcttggaa gtacagggat cctctgctac ctgaaaacgt tctgagtatt cactttcatg   33120
gattgcaaag tcatttaccc aaaattcact ctccaaatga aaagtgagta tgatgaatca   33180
gtattcaagt tccacctggg tcctgggaga gggcatggac atcatatccc agctgttccg   33240
acaggaggac ccaatctgag tctcactgcc tgcctgcatc gtttgtctgc tgccagcctg   33300
cacagtagga agggaaaaca tgatttgtat ctgttttagg tcaggttccc aagaagtaga   33360
gcctgagatt ggaattcttg gaaaatggtg tttgcgggag cgctgtcagc agaagctata   33420
aggaagttgg ggggacagaa aacgagaggt aagaagccag tcaaaaaggc aggtccagct   33480
taagtccgcc tcagtctggt tccacaaggg ctctgatgca tgaagaatat cacagggttg   33540
tccctcctgg gagaggggcc agcctattgt acctgtatca aagccaccag ctgagggcca   33600
gtggggaggg aagatcttcc aggcatttcc aggaaactct caggagaagg gtgtagctgt   33660
gagcagtctg cagctgctgc tcactgcggc taaaggctgg gtgtgcaggc cagtcagcca   33720
gtgaggtgcc aacagcaggc actacagtcc accccttgac tgctcagacc tactgctttc   33780
cactttaagc tctctccatc caggcacagc ttcagggaaa acttacaatt ggagaaacag   33840
agggatgaac tacaatgccc acttctgcat gtgattgtaa gactgtcact gatactcacc   33900
atcatgcccc atccccacca tccattctag tgtccccttc cccttggcta acactgctgg   33960
tctaggtgac ttccctagag caggagccaa acccttatcc ctgaggcatc tgaatcctgg   34020
attcctttat caggctattg ttgttgtaag ttgtccattc ccaattacaa ctggacatga   34080
gactaccaag aaacaccctg gcaaatcatc tgagtgcaag ccatattctt cctgctccat   34140
tatgtagcgg tagtcctacc tcctaatgac aagggtaaat tgccacattt tgctccttgt   34200
gccaggatga taatacccttt ctctacctgc ttggctactg gcacaaggaa gcacagcatg   34260
accaggaggc aattgtagct gtacatttag tgaatgtgtt aatgtatcac ctggtggaag   34320 gacccctct gagaaccagg acttctagac ccacaaaacc taaagttgtg aatggcggaa   34380
gcacaaattt cccaagtgga tcatggagag tgatgaagag ttcttggttc ccaaacccac   34440
atattttacc tttcaggaac atggcctcat cccatagcca ttagagtgca tattgcattc   34500
tggaggagac tgggccctcc tcatgggtgt catcttcaag atgacagctc cactgtgcct   34560
ccaagaggat gctccaccac cctatctgtg attccttggt tagcaggaca ggctgctgca   34620
ctgagggtag gaaaggcaag tccattgatg gctggaatac atgtcaatcc aagtcaagag   34680
aaaatgccgc ccttttccagg ttggaagggg cccgatttag ccaacttgtc acccagtagt   34740
ggctggttgg tctcctccag gagcagtgtt ataccaggaa ttcagcacca gtcgctattg   34800
ctggcagttc ttacattcaa cagcagcaaa actaggtcag ccttgatgag agggaatgta   34860
tgcttctggg cacaggcatg gcttccttct ctgactccat gactatctat ttctgagtgc   34920
atggtggccg acattcagct gcctgcccat cctatccact tggttattat tgcctcttcc   34980
acaagaagtg gttctggct gtcattaatg tctcatactt tgtgcccact cacacaggtt   35040
tagctctaca acttttcccc atgccaccac ttttccacaa tcttctaatg ttgctccttc   35100
caagctactg aagaacgagc taagctattc accaatgtcc atgagtctat atttaccta   35160 ggccacatct ctctccacac aaagtgaata agcaggtgca ccctccaaaa ctctactaag   35220
aggatttctt ctccccagtg tctttcaggg ccaccttgag tggggctgaa gtacagcaga   35280
```

```
agtccatttc cagcttgcat caacattcca aactaaccta tccatgatca atgcatagat   35340
gggtttttcc ctcctccagc agctagacaa aagacacccc ccaccaggag gccatatttg   35400
catgtgggtg aaagagaggc acaggggcca atattcgtgc aacagtggta gatggcaggt   35460
gggtctgggc cacctgtccc tgcagcttat ctgtgccatc tggacctgct caagcctgat   35520
tccagatata ccatttccat cttatgatgg atggcttatg acctagtggg tctgacagca   35580
ccaaactcat aatgggcagt tatgccaca  tggtcactta atgtcctatg gtcagacact   35640
ctgctgagtg gcatgccagg aaatgcttta caagtggtgt ttggttctct gctgcagatg   35700
gcatgacctt ggtccggagc cctaggggtt tggacagtga ctcctgttgg ggcctaatct   35760
cacattccat gcagagtatc atcagatttg ccaatcacat agcctaaggg tcaggactga   35820
tccaaccagt ttttgcagag atcaaactgg agaatgaaag gttgatatga tgtgaccatc   35880
atatcacgtt tttctctctt gaaaagtatg cagatgtctg aaagagacaa gtgccccagg   35940
agaaaatgca tgccttcctc aggatcggcc cccacctccc ctcctggcca caggagggt    36000
caaatctcag catggcccaa cttggacctg tcaaggaaga agaaaaaaat tgtatgccaa   36060
aggaactcag tctttggcta acaagtacta gacatccttt aagtctttga gaatggtaat   36120
aatttctgcc atccctccag atttgtgttt ttctgttttg gctgggtggg aatgcagcat   36180
tttcactttg ccttttgttat tacaaatgtt gcttattcta taaatcaagg aaccattgta   36240
agggctcttc tgatggttaa gtatatccat tccaatgatt tattcgggat ccaaggaaat   36300
gatttctggg tgaatacaca gaactagtgg atccaatttg agacatacct gggccagaac   36360
tatatttgtc gtcttacccc aataagcctg cactctacta ggacagccat gacagcactt   36420
tgggacccta gatataagtg tgaattgctg gctgggcatg gtggctcacg cctgtaatcc   36480
cagcattttg ggaggctgag gcaggtagat cacctgaggt caggagttga agaccagcct   36540
ggccaacacg gtgaaacccc atctctacta aaaatacaa  aaattagctg ggcgtggtgg   36600
tgggtgcctg taatcccagc tactcgggag gctgaggcag ggagaattgc ttgaacccag   36660
gaggcggagg ttgcagtgag ccaaaatcac accactgcac tccagcctgg gtgacagagc   36720
gagattccat ctcaaaaaaa gaaaaaaaa  agtgtgaatt gctatgaaat cactatcaaa   36780
agatctgagt gttacccta  ctcagtgtgg tcgaatataa atagccatag gttcctgtta   36840
tacacacttg ctgtggtgct acagagtctt tcctcatggg aacccagtcc ctctttcagt   36900
caatgggttc tggttcgaga actggctgag gtttggaaac tgtgcctttc catcataact   36960
ttccactggg gtgactgacc ttggccttct gttcatcctt tctagcccct aagaatccaa   37020
cactctatta gccttctcct tagaccccta taagctaatc ccttctagtt gttagtctga   37080
ccttggtgcc caatatgata attattccca ctttgcttct gatatgcttc taagtgctgc   37140
ccctggtctc tgcccttaag tgatctatca tccccactgc cattaggggg agaagctctg   37200
aaaaagagtt gtctcccatc aactctggtc tacaaaggac agccctactg agcctcagcc   37260
atgtgcccga caccagcaga ttctttacag cctgggaagc agagtgtctt ccctgccttt   37320
ccagggaaca tagccagctt acaggctttt tgatcttata gagtaggtca gttatatttt   37380
gccccatttc ttttatcctt ttgatcactt cctcttggcc caccatgtaa actcaagcat   37440
ccctgcttca tttaatcgag ctgttgcttt ttctaagcta ccaagagcaa ccccagcaat   37500
atatcagagc cctctcttgg gaccctttgct agggtgttaa atcctgcatc ataggagaat   37560
gcccccacat cagcaaagtc cccttatcct cttgatatcc cacctgcccc agtccagcac   37620
```

```
cttcaggatc tggtctcaat cacaggatcc agcacctttg ggactgttgc aagcataaga    37680
tccagcactt tgggatcta gtctcccact tcctgctagt acttgttagc aaagactga     37740 gttcctttgg catacaattt ttttcttctt ccttgacagg tccaagttgg gccatgctga    37800
gatttgaccc tccttgtggc caggagggga ggtaggggcc gatcctgagg aaggcactca    37860
ttttctcctg gggcacttgt ctctttcaga catctgcata cttttcaaga gagaaaaggc    37920
ctccttctca cagcaagact acttctgtag atgcaggtgg ctcgtgggaa tctggcaatt    37980
caaaattctc aagtgtactc actagcacat tagaaaacca gtagtacaca tctctttcca    38040
aatcttcatt cagtgacact atgtcagtag ctggaaatgg gccatggtgg gtgtatttaa    38100
accatgaaaa tcagaaaatg ctacaaacca gggcatcccg catctctaga cagcagattg    38160
ttggccattt cccagcatac cattgtgtat actccttccc atcagggccg tggcttgcct    38220
tggtggagga ctcagccctt gctgaagttc tgctactgct cttacaattg agtcctatgc    38280
ctggtctcca gctctgcctg cctcactaca ggagacaagc atctctttga acactgccga    38340
gaagaccctc tggctctcag gcttggcttt aaatcgatag acctgagcct gccattttct    38400
cttttccatg catcactcca ctgatccaca ggtctcagtg gcatagtcct tcgggttagc    38460
atctccccca caccctcggt gccagagaca ctgagtaaga aagtacctcc ctgtctaccc    38520
ccatccccgc tccccacagg cagggccttg gcgatccact gctgcaatgt gccagagact    38580
gtcagtactc ctaccaccag tgaggtggca accagctggg aagtgatcca actccagagt    38640
cccgccctca taggctgatt tctaggacca cccctggtat actgtgttag gttcttgaag    38700
cagagcctga gataaggatt ctggcacctg tgattgagtg ggagggtgct ctcaggatga    38760
gatggggtag aaataggcaa aggtacagat tcagcagcag ttgagcctca gtctgaccca    38820
gcagggagct ctcaaatgtg aatgacatca cagagttgtc cctctgaggc aggggccagc    38880
ctttgtgctc ctacatgagt cagtcactgg ctggaggccc ctggggaaag gctagggctg    38940
ccagctttag caaataaaaa attagggcac tcagttaaat tgaatttcag ataaacaaca    39000
```

<210> SEQ ID NO 6
<211> LENGTH: 45980
<212> TYPE: DNA
<213> ORGANISM: Homo sapiens

<400> SEQUENCE: 6

```
actagcacat tagaaaacca gtagtacaca tctctttcca aatcttcatt cagtgacact      60
atgtcagtag ctggaaatgg gccatggtgg gtgtatttaa accatgaaaa tcagaaaatg     120
ctacaaacca gggcatcccg catctctaga cagcagattg ttggccattt cccagcatac     180
cattgtgtat actccttccc atcagggccg tggcttgcct tggtggagga ctcagccctt     240
gctgaagttc tgctactgct cttacaattg agtcctatgc ctggtctcca gctctgcctg     300
cctcactaca ggagacaagc atctctttga acactgccga gaagaccctc tggctctcag     360
gcttggcttt aaatcgatag acctgagcct gccattttct cttttccatg catcactcca     420
ctgatccaca ggtctcagtg gcatagtcct tcgggttagc atctccccca caccctcggt     480
gccagagaca ctgagtaaga aagtacctcc ctgtctaccc ccatccccgc tccccacagg     540
cagggccttg gcgatccact gctgcaatgt gccagagact gtcagtactc ctaccaccag     600
tgaggtggca accagctggg aagtgatcca actccagagt cccgccctca taggctgatt     660
tctaggacca cccctggtat actgtgttag gttcttgaag cagagcctga gataaggatt     720
ctggcacctg tgattgagtg ggagggtgct ctcaggatga gatggggtag aaataggcaa     780
```

| | |
|---|---|
| aggtacagat tcagcagcag ttgagcctca gtctgaccca gcagggagct ctcaaatgtg | 840 |
| aatgacatca cagagttgtc cctctgaggc aggggccagc ctttgtgctc ctacatgagt | 900 |
| cagtcactgg ctggaggccc ctggggaaag gctagggctg ccagctttag caaataaaaa | 960 |
| attagggcac tcagttaaat tgaatttcag ataaacaaca aattattttt tagtatatgt | 1020 |
| cccaaattgt gcataacata atgtgttttc tccgccagcc ctgggaaggg cgtaacttcc | 1080 |
| caggtatttc taggtgaagt aactttgtag atcaggagta agtcccagga agaagtcca | 1140 |
| gctcttctct tcagccctgg gcagctgggg gtaggcacag gggcccagca ggcacccata | 1200 |
| gcatctccta cagcatctga aatgaacagg gtcatcacgt actacataca aatgtaccca | 1260 |
| ctgctgagtt cttcagggat tatatcatta ggtacttggt atttaaata cattacatta | 1320 |
| tgcagaagtc ctttgtggat tgctatattt ggagagtttt tgatattgg ggggattaga | 1380 |
| tggagttttc agatgggcat catacggttt ttcatttaaa accctagagt attgtaatcc | 1440 |
| tagggagtga tcctgcgatt agtaaattag ctctccaata gattttcaat gtggttgcaa | 1500 |
| aggacatgca tgtggttcac cctcccagga aatccagaag ggcagcattg gcctgagtgg | 1560 |
| cctgagtttg gctggttggg ctggtaatgc tggacaaaga caatgggtgg aatggtttgc | 1620 |
| ttccctcagt cctttcagac acagcccagc ccaccacgtc aagccagtgg gtgcatctgc | 1680 |
| aaccaatccc catgagaact gcagcctctc agaggtgggc aagttggccc gggtgggtca | 1740 |
| ggaggatcag atgttgagga aatctttgga ttggaggcag gcagagcagg gaagcatcgg | 1800 |
| gtgattctat gacagaccca gggctccaag ctgcagttca ggaggggcac tggcacggcc | 1860 |
| tctgctcaac tcccccttga gtgacatcag gtgaagtgcc gacaacacag aaggcagcaa | 1920 |
| atgctgccag tcaggtctgc ttcccaggac agccagttgc taaccttcct ccagcacagc | 1980 |
| actggatttt ggtcacctgg ctgggagctc cacctcccca gctgctgcct cacctgcttt | 2040 |
| tccaaacccc accctgtaaa cggtaactac attttgtgcc cactacgcct cgtttccatc | 2100 |
| tctttggagc acctctcacg tggagctgaa cagaacgacc tgttaagccc accgtgtctg | 2160 |
| ttaggggttgt ctaggctgta tcagataccc aactaaaact ggattcacca acaggtattg | 2220 |
| tcaaagcaca taagaaagag tccagaggca ggcagctctc agcctggtgt caggctctgg | 2280 |
| gtcagctttc cagattctct taaccttccc cacatctgcc agatgccgcc acaggcacag | 2340 |
| gaggtacaaa caaacccaaa aatgttctgg aaacaagaag ggaaggggat ccccaccata | 2400 |
| tctccccaga ggccttcctt ctcacatctc actgtactga agccagctct agcagaagac | 2460 |
| agcagggtga atttgtccag ggtattcagc ccccagtgct gggtccatta ctacttgacc | 2520 |
| cctgaataaa acagaggttc catgagcaag aaggaagggg aactggatgt tagagggcaa | 2580 |
| gaatgtatcc atcccacccc taggagcacg catggacaac tgcccatttt ttgctcctat | 2640 |
| tgcagcccag ggctagccc agagaccttg ccagtgctga gtcacaagat gctgggaaag | 2700 |
| tgagaccaga gcctggtctt ggggaacagc tcaaggccgc attggtctgc aggtcataga | 2760 |
| gcagctgctg agcagtgaga gcccacgatg ggccaggccc tgggtcttgg agacctgaat | 2820 |
| gagatagact gggttcctgt tctcctgggc attgcctctt agagggcaaa gacaattaac | 2880 |
| aataaacaaa tagaacatga agtgttttcc gatagtgact gatatacttt ggatatttgt | 2940 |
| cctctccaaa tctcatgttg aaatgtaatt ccttatgttg gaggtggggc ctggaaggag | 3000 |
| gtgtctgggt catgggggca gatccctcat gaatggttta gtgccatccc cttggtgatg | 3060 |
| agtgagttca cgtgagagct ggttgtttga aagagcctgg cccctctca ttctcctgct | 3120 |

```
cccactcttg catgagacac ctgctccccc ttctccttct gccatgattt taagattcca   3180
gggacttcac aagaagcaaa tgctaacgcc atgcttcttg ttctgtctgc aaaactgtaa   3240
gccaattaaa cctcttttct ttgtaattta tccagtcttg ggtatttctt tataacagca   3300
caagaacagc ctaatacagt gatgctctcc aagtgacctt tgggctgaga cctgaagaag   3360
aaggggaagc agttaggtct gatagctcat gcctgtaatc ccagctcttt aggaggctga   3420 agtggggagga ctgcttgagc ctaggagttg aagaccagct tggaaaacat agcaagaccc   3480
tggctctaca aaatatttt ttaattggcc aggtgtggtg gtgcacacct gtagtcccac   3540
ctacttggaa ggctgaggca ggagcatctc ttgagcccag gaggttgaga ctgcagtgag   3600
tcatgttcac accactgcac tccagcttgg gtgacagagc aagacctgtc tcgaaaaga   3660 agaaagaaga aagtaggaag aagaagaaga agaagaagaa gaagaagaag aagaagaaga   3720
agaagaagaa gaagaagaag aagaggaaga ggaacaagaa caagaagaag aacaagaaga   3780
acaagaagaa gaacaaggag aacaagaaga agaataagaa gaagaaggag aagaagaaga   3840
aggagaggaa gaagaagaag aggaagagga ggaagaggag gaggaggaag atgaggagga   3900
ggaagcagaa gcagaagaaa aagaaagaaa agaaagaaag agaaagaaag aaaagggaag   3960
gagggaagga aggaaggaag gaaaaggga aggaaaggga aggagagggga gagggagaag   4020 gaagaacaaa gaagaaagaa ggagaagcag aggcttgtgc tggatagcct tgcttttgcc   4080
aatgaccttg ctgatttca gggggtcctg gtgtcttagt ccatttgtgt tgctgtaaag   4140
gcatacctga ggctggataa tttacagaga aaagaggttt atttggctga gagttctgca   4200
ggctctacaa gaagcatggc accaatgcct acttctgatg agggcctcag tctgcttcca   4260
ctcatggcag aaggtgaagc agagcctgca tgtgcagata tcacatggtg agagaggaag   4320
cacgaggggg cagggaggtg ccagcctctt cctaatagta agctgtcttg agaactaata   4380
gagtaagaaa taactcacac cctgccccca aggaagggca ttaatctatt catgaagtat   4440
ctgcccccat gacccaaaca tctcccatta ggccccccac ctccaacatt gaggatcaaa   4500
tttcaacatg aggttccggt gggcaaacat ccagctataa tactgggcaa tgctgaccag   4560
actcttcccc tctcaggccc agagctcctt ggccctgtaa caacagaaaa ttgcgtttga   4620
gtgtcaagat tttccttta gtccccatgc agctccttag aatgaggtgg catcttctcc   4680 ctttttcatag gtgaagaaac agaagctctg gaggaacgaa tcattcatcc aaggtcaggt   4740
agctagtaag cgtcccacca gctccccaga tctcctgttt cctgtcccaa gtcccactga   4800
gtgagctgga acaatggctt cactggcacc tgccgggaat ggtggcaggt gcctataatc   4860
ccagctactc gggaggctga ggcatgagaa tcacttgaac ccgggaggca gaggttgcag   4920
cgagccaaga tcacaccact gcactccagc ctggataaca aacggagatt ccatttaaaa   4980
aaattaacat ataatataca tacagtaaca ttcactttt aagtgtacag tttgatgagt   5040
tttatcaaat gtatatggtt ataaccac catcaccatt aaggcagaat cttcccatca   5100
ctcaaataat tccctcagcc ccacctcttg ctgtcaatca cttctcccac cctagccact   5160
ggaaatcatt catctgtttt ctgtcccctt ggttttgcct tttctagaat gttctataca   5220
tgagaccact gagaatatag tcttctgtgt ctggcttctt tcacttaaca taatgcctag   5280
ctcagcagtg tgtcaatcct ccctcccttg ccattgctga gcagtgagta ttccactgta   5340
tggctgtgct acggtgtgtt catccattta ttcattcacc agctaatggg catttggatt   5400
gtttccaggc tttggctatg atgagtgaag ctgctgtgaa tgttcaagta caagtctttg   5460
tgtagacagg ggttttcaat tggcgggata aatacctagg agtagtatcg tgtggttaag   5520
```

```
cgtacgttta aacttagaaa aactgtcaaa ctgttttcca atgtggcctg taccatgttg    5580
catttccatc agcagtgttt gagaattcca attgctccac atcctcctcc cgacacttgg    5640
tttcacccat cttttaaata ttagccactc tggtgactgt gtagtgatat gtcagtgtgg    5700
ttgtaatttg catttctatg attgactaat aataatgttg cagatatttc tgtatgctta    5760
gtgggcattt ttggtgagtt tttaaaaatt gggttgttgt caccgtctta ttgagttgga    5820
agaattcttt atatgttctg gatgtttatt catgtgtgtg tctgctaaga ggtgagactg    5880
gttctaccct ggtcctaaca agcaccctgg gcctgcatcc cttttgtgt ctgtgagctg     5940 ggtctgcagc cctctcctcc cactacctac tgcccagcag tacccctcac ccatcactgt    6000
ggctcctgca atgacatctc agcctgtctc tccctccctc cagctagcca gaggcaggat    6060
ggctcagtga cacagggtgg gccctgaaga cagagtgcca gggtttggac cttgtattag    6120
caagagtcac aagggaaact tactttatct ctccatagct ctgttgtgag gatccaataa    6180
attaatccat agaagagctt aggacagcac ctggcacaaa gtatacatga gctattatga    6240
tgttattctt ccaacccatt gtttctgtgt tgtcataaac atgaatgcag gactcagtgt    6300
cccagctctg tgtccctcgc atacattccc taacagccca caggtcttgc ctgtcaccgc    6360
ctcattcaat aagtgatgac tctgcctctt ccttggctgg ggccttgcat tggacatttc    6420
tgtatccata tttgttttt aaaaactagc tgttggccgg gcgcggtggc tcacatctct     6480
aatcccagca cttgggaggc agagacaggt ggatcatgag gtcaggagtt caaggccagc    6540
ctggccaaca tggtgaaacc ccatctgtac aaaaaatacg aaaattagct gggcgtggtg    6600
gcatgcacct gtaatcccag ctacttggga ggctgaagca ggagaatcgc ttgaacctgg    6660
gaggcagagg ttgtagtgag ccaatatagc gccactgcac tccagcctgg gcaacacagc    6720
aaaactccat ctcaaaaaaa aaaaaaacaa aaacaacct agctggactt gacactcttg     6780
ttagaggaag atttttccac atctgttaac ttttcttcta ttgttatcca tctgtgcagg    6840
tttttctgtc ctcctgagtc atttttgataa tttatattat attttgaaaa tcatccattt    6900
cctatagttg tttattagtg tcttctctgt tatatttgat cagattacca aatcttgctc    6960
attgattgcc catttatttt attgtgttta ttttttttgag acagggtctc actcgacagc    7020
ccaggctgaa gtgcagtggt gcaatcatgg ctcactgcag ccttgacctc ctgggctcaa    7080
gcaattctcc cacctcagcc tcctgagtag ctgggacctc aggcacacgc caccacagct    7140
ggctaatatt ttatttattt atttatttat ttatttttgt agagatgggg tctcactatg     7200
ttgcccaggc tggtttcaaa ctccttggtt caagtgatcc tcctgcctca gcttcccaaa    7260
gtactgggat tacaggagtg agccaccatg cccagcccct atttacttta tagtaagtgc    7320
cttcatgggc ataaatgttc ctctgagaca gctttggcta ttagccatac ttttaatatt    7380
ttgtacattc atggttattc atttataaat ggtctgtaat gcaatgcaga tttccccttt    7440
ggcccaaatg ccatttacag cagcactttt ctctttctga gcagacagaa tattttggtt    7500 tccctctgt tgtttatttc tcgtctgcct cgcctcattt gctaggtgtt cccttggtgt      7560
gccttaagta tgagccactc aaatatttgt gtttctctaa acaccctga cactgtcctg      7620 ctggtttctc tatctggaat atccttccct tcttggccag ttcccctag tgcatcaaag      7680 aaatcctgct cttttgcctt cagaaaacaa acaaaacga aacctatcag tctccttatg      7740
tccccaaaga catagctttg ctggtatctg gttgtattga gctgttcatt tgtctcttct    7800
gctagatggt aagctccttg gaaactaaaa actaatcact tttctaactt cagactgagc    7860
```

```
acaaattagg ttctcaagaa acattgaata atgagtgatc cggtatcccc ttccaacata    7920
tttttggtca ttgataccat cattctgagt agttactagg gaacacttca ctgcagtaac    7980
caatacagca aaacgtgaaa tacagttaca tagtagaatt gtatttcttg cccatataat    8040
agtcaagtgc agttcttcat cagctgggag gttctcctcc acacagtcat ttaggaatcc    8100
agggaacata gcagaggttg ctagctctag acccaaaccc atgtcctctt tgtccacagt    8160
gaggacaatg ccagcaacag ctggccagct gttctgtagt tctcagcctc cctcgcagtg    8220
agatgtctcc atgcaatttc agtggagcaa catataccat ttccatttcc aggtgtaggc    8280
tcctaagaag agggtggctt cttcatgttc tttctcacct ttccgtaggc tagctgcaga    8340
taatgatgag gctttaggga gtgggtggag ccataaagta gaagcctgga ttcctaaatg    8400
acggtgtgaa gtgttcccta atttcacgta attgtttctt aatttcctgt ttgggttatt    8460
tgttgctaag gtataaaaaa accctgattt ttgtgtgttg atatttgtgt gctgcaactt    8520
tgctgaatta gcttattagc tcaatttgat ctcagatatt agctcaaata ttttgggaga    8580
ttatttatgg ttatctacat aagatcatgt catctgaaat aaagatagtt ctatttcctt    8640
ctttctatct tagtccattt gggctgctgt aacaaaatgc cataaattgg aggctgagaa    8700
gtccaagatc aaggcccaag ctaattcact gtctgatgaa ggcctgcttt ctggttcata    8760
catggcacct tctagctgtg tcctcacatg gtggaaaagg caaggtagct ctctgggatt    8820
cctttttgtt tgtttgtttg ttttgttgtt tttgtttgat tttttgagac agagtctcac    8880
tctgtcacca ggctggagtg cagtggcaca atctcggctc attgcaacct ctgactccct    8940
ggttcaaacg attctcctgc ctcagcctcc tgagtagctg ggattacagg tacccatcac    9000
catgtccagc tacttttttgt attttttagta gagacagggt ttcaccatgt tggccaggat    9060
ggtctcgatc tcttgacctc gtgatctgcc caccttggcc tcccaaagtg ctgggattac    9120
aggcatgagc caccgtgcct gtcctccggt attctttta taagggctct ttttcttttt    9180
atgtgggctc taccctcatg acctagcacc ttctaaggcc ccacctctta atatcatcac    9240
acagcagatt taatatatga attttgaggg gacacattct ttccatagca ctttccagta    9300
tggataccct ttatttattt ttcttcccta attgctttgg ttagaaatgt cttccctaat    9360
tgctccacta ctatgttgaa aagaagtggc aaaagtgggt attcttgtct tgctcctctc    9420
ttaggaagaa agtttaagtc ttttgccatt aaatatgacg ttagctatgg ggttttcata    9480
tatgacattt atcatgttga ggaaattttc ttcttgtttc aatgatgaca gggtgttgag    9540
ttttgtcaga tgcttttttct gcatcaatca atatgaccat gtagtttctt tgttttattc    9600
cattattgta gtacattaca ttaattttg catgttgaac tattcttgtg ttcctgggat    9660
aaatttcact tggttatggt gtataatcca taaccataac ctgaagatat gctgaagagg    9720
ctaagtgcca tggctcatgc ctgtaattcc aacactttgg gaggctggtg tgggaggatc    9780
acctgaaatc aggagtttta gaagagcctg gcaagtaaaa caagatccca tctctacaaa    9840
aaattgaaaa ttaccgctgg gcatggtggc tcacgcctgt aatcccagca ctttgggtgg    9900
ccgaggcagg cagatcacct gaggtcggga gttctagacc agcctgacca acatagaaaa    9960
accccgtctc tactgaaaat acagaattag ccaggcgtgg tggcacatgc ctgtaatccc   10020
agctactcag gaggctgagg caggaaaatc acttgaacct gggagacgga ggttgcagcg   10080
agccaagatc atgccattgc actccagcct gggcaacaag agcaaatctc cgtctcaaaa   10140
aaaaaaaaaa gaaaagaaag aaagaaagaa aagaaaagaa agaaaattag cttgatgtgg   10200
tggttgtgca cctttagtcc tagctactca ggaggctgag gcaggaggat tgtttgagcc   10260
```

```
caggaggttg aggctgcagt gagccatgat tgcaccactg cactccagcc tgagcaacaa   10320
agtaagacct catcactaaa aacaaatttt ttaatactga agaattttat ttgctggtat   10380
tttgttgagg attttgcatc tatattcaca agaaatatta ctctgtagtt tttcttcttg   10440
tagtatcttt gtctggtttc agtatcaagg caatgctggc ctcatgagat caatcaggaa   10500
gtgttacttc ctctttta tt ttttggaaga atttgagaga attggtgtta attcttcttt   10560
aaatggttgg tagaattacc agtgtagaca tctggtcctg ggattttctt tgttgggagg   10620
ttttttagta ctaattccat ttccttactt gttattagtc taatgagatt ttctgtttct   10680
tcttgagcta gttgtagtag ctcatgtgtg aattttt ct atttcatcta agttatccaa   10740
gtttacctaa gttaaagttc cattttatct aacttgggta agccaacaaa caatactaaa   10800
ttgttcatag tattctctca tagtcctttt tttctctaaa gtcagtaata acgttcactc   10860
tttcattttt tcattcctga ttttaataat ctgagttctt tctctccccc tccctgcaat   10920
tgagagtcat ttaaaagtgt cttgattaaa ttttatatat ctgtgagttt tccagttttc   10980
cctctgttat tctcttctag ttttatttca tgtgatccaa aaagatactt tatatgattt   11040 caatttttt t acatttacta agacttgttt tgtgactaaa atatccttga gaatttccat   11100
gcacatttga gaaaaatgca cattctgctg ttgttggaca gagtgttctg tatatgtctg   11160
ttaggtctaa ttggtttaga gtattgttct agtcctctct ttccttattg atcttctgtc   11220
tagttgttta atccattatt caaagtagtg gccgggcacg gtggctcaca cctgtaatcc   11280
cagcactttg ggaggccgag gagggtggat cacaatgtca ggaggttgag accagcctgg   11340
ccaacatggt gaaactccgt ctctactgaa aatacaaaaa atttgctgga catggtggca   11400
cacgcctgta atcccagcta ctcaggaggc caaggcagga gaatcacttg aacccaggag   11460
gcagaagttg cagtgagctg agatcgcacc attgcactgc agcctgggca acagagcaag   11520
actctgtctc gagaaacaac aaaaacaaaa acaaaaaaca aagtagtgta ctaaagtctc   11580
caactactat tgtagaactc tatttctccc ttcaatgttg caaaattttg tttcatgtat   11640
tttggtgttc tgttctttat aatttttata tcttcttaat ggatgaaaac tttatcaac   11700 atataatgtt ctttgtctct tgagacttt t tttttaact taaaatctat ttgggctgat   11760
aatacagcca ccacaactct catattggtt gttattttca tagaatatct tcttccatcc   11820
ttctacttta aaattcttct atctttatat ctaaagtgag cctcttgtag atagcatata   11880
ggtggataat gttctcttta ttcactctgc caatatctgc cttttaactg gagtttaatc   11940
tatttatata taaaataatt actgattagg aaggacttac ttctaccact cagctatttt   12000
ttttctgtgt gtcttataca tttttaagtt tctcaattcc tccattactg gattttttt t   12060 tttacttctt gattttgtgt ctgtgttgtt acatttgat tatttctcc ttttgatagc   12120 ggcaggaggc agccaaatgc ctggcagata gaagcttgtc ccccatgaaa ccccaccttc   12180
aagccaaaaa atagcctgaa ggctgaaaga ccggactgct ggtcccagat gaaacccatg   12240
atccagagtg agaacttcca ttcctgtttg cctgccctct aaataatccc ttttaaccaa   12300
tcgaatgttg ccttttccaa tactacctat ggcctgcccc tccccattc tgagcccata   12360 aaagccctgg aatcagccac attgggggca ctttgccaac ttcaggtagg gggaccacct   12420
ctgtatccct tctctgctga agctgttttt catcactcaa tgaaactctc accttgctcc   12480
ctctttgatt gtcagcgtat cctcattttt cttgggtgtg gtacaagaac tcgggaacca   12540
gtgcacaagc cagacttggt ctgggcagca cgggttagtg ggccatctcc cacagcaggt   12600
```

```
agcatggcca agtgaggcct gggcagggca tcaccaaggt ccctggcttg caaagtgacc   12660
aaggaaaaaa tcctgtgtca cttttccttt ctcatatttt ttagttattt tcctaatgat   12720
tgccttgagg atggcaatta acatcttaca cttataagaa gctagtttga ataatagttc   12780
caatagtaca tgaacactct actcctatat atctccatcc ttcttccttt atattgttat   12840
tcccacaaat tatgttttta tacattatat cctcactaac ataaacttat tattatttc    12900 tgcatttgcc tttaaatca tacaggaaaa caagaatcac aaagaaaaac tacattaata    12960
tttgctgtta tatttaccta tatagtgaca tttaacagtg tattttatg tcttcagatg    13020 tctttgaatt actacttagt gtcttttcat tttagcctca atgtttccct ttagcatttc    13080
ctatagggca ggcctgccgg taattaattc cctttggttt tctttatctg aaatgtctaa    13140 tttcttttt attcttgaag aatagttttg ctggctataa gattcttagt taatagtttt     13200
tttcccagca cttcaattat tattaaagtg ttattattat tattattatt attttgagat    13260
ggagtctccc tctgtcactc aggctggagt gcagtggcgc aatctctgct cactgcaacc    13320
tccgcctccc aggttcaagc aattctcctg cctcagcctc ccgagttagc tgggattaca    13380
ggtgcccgcc accatgccca gctaattttt gtattttag tagagacggg gtttcaccat     13440
gttggtcagg ctgatcttga actcctgacc tcaagtgata cacccacctt ggcctcccaa    13500
agtgctggga ttagaggcat gagccaccat gcctggtcta aagtgtaatt attattacag    13560
ctgccatttg gcctccttgg tttctaatga gaaatcatct gttaaactta ttgcaaatcc    13620
ttggtatgta tgctatgtgt catttctctc ttgctgcttc caagattctc tctctgtctt    13680
tgtcttttga caattgact ataatgtgtt tcagtgtgaa tttcttagag tttatcccac     13740
ttggatttca ttgagcttct tggatgtgta cgtttgtctt tcaccaaatc tgggaaatta    13800
tttcaccatt tctcaaatat cttttcttc ccctttccat ctctcttctt ctggagctcc     13860
cgtatactta gttggcatga ctgatggtat cctactggtc cctcaggttc tgttcatttt    13920
tcttctttct tttttctgc tctgcagact ggataacttc aatcgccttt tcttcaagtt     13980
caatgattat ttcttctgcc tgctcaaatt ggccatttaa cccctccagt gacttttca     14040 tttcagtatt gtacttttca gatccagaat ttctatttgg ttcctctttta ataaattctt   14100 tttattgtca ttccccatct gttcatacat tgctctccca atttcctgta gttctttgtc    14160
catggttttc tttagttaat taagcatatt taagacagtt gacttaatgt ctttgactag    14220
taattccaat gtctaaaatt ccttatggat agcttctttt aaattatttt tgtcctgtta    14280
gagagtcata tcttcctctt tatttgcttt gtaatacttt gttgaaaact taacattttg    14340
agtagtaaaa tgtggtaatt ctgaagccag attctccccc tcctttgaga ttggttttgt    14400
tgtttgttga gggctgcagt tgtccatttg tatagtgact tttccaaacg attttttgcaa   14460 agtatgtatt ctctcttgtg tctggtcact gacgtttctg ttctggtgcc tctgcagtca    14520
gcctatgacc tggaagagca ttccttaaat gcatagattt ttttaaaacc caagaaacaa    14580
aaaacctagc atgtatgtac ctttttaaaa atcttctgat agatgccacc tggaaggctg    14640
ctgctgcctg aaggggcaga aacaaaggca agctctactc tgagccctca gggaaccacc    14700
agataaacaa aagaaatttg attctccaaa tttctggaag acaaggtcct ttctgcccac    14760
tcctgctcca gccagctgct ctaggaacac aattactgtc cacatggcca caggaatgtt    14820
gaagaatgca ggatggtagc tggtttgccc acaccactca cttatgagcc atcagcatgc    14880
ctctcccttc atcgagcact cccatggttg ctgtaagtgt ccaatcaggt tccagaattc    14940
tgaaagagtt gactcttaca ggattttttt cttttctaac ttgctggttg tttagataga    15000
```

```
ggaaccaatt cctgaagttt cctacgttgc cagcttcatg aggatcattc cctagtaact   15060
cttttcagac aaaaagcttc attgatttac tgtaggacta gcatcaaaga gtctatgcca   15120
cctagtctgt ctccttaaaa cacagaaata atcagtatgc attggggtag gagtttggca   15180
ttagatctgc cgtaaatcaa gagctgggga cagcccatgt cttaaactct gacccaaggg   15240 ctaaatatc ctttggtagc aacaacagct acaaactatt gaacaacttg tatgtgccaa    15300
gagccttacc tgcattatcc cattgaatcc tctcaacagc cctgtgaggt agtagaattg   15360
ttgcctgccc cttactgagg cctagaaaca ttaaggaatt tgcccgaggc cctagagcca   15420
gtgagtggca aagccagtct ccagactcag gctggagatc ctacagttct gtgttacccc   15480
agtgttatcc tgcctctcag cacagagtct tggatgattc tcctaacccc tccctaggca   15540
atgcacaggg ctgctccctg cacccttact catgctctgc tcttcaaccc caacagtgct   15600
ggccttaggc tttatccctg acacccagcc ccaggctcca ttccatctgt tgacagaggc   15660
aaacactggg gcaaaactga cctctgtgga taccactgtg tccacctcca ccagcttcag   15720
ctgaagcctc tgaacatctc cagcatggaa gaagccccaa aggatatttc ctgtccccca   15780
gcatatgctt gaccctgaag ccctcccat ctagtcaaga agaccaaaact gttaacaatc    15840 ctggagtcag agtgacccat gggtgaatct tagccaagtc actcatagct gttgcatcct   15900
agtaaatccc ttaactccca taggcttcag tttccctgca tataaaatga cagccttcag   15960
ctcatcggcc agtttcaatc catctaaagg gtctagcaca tcccctggca tgtggaagcc   16020
acagggcaca cactagttgt ggtcatttga tcctggcatg ctctgctgtc tctcggctct   16080 cccccttgcct cttcccctga tgtcctggcc atcagccact gcctaacacc ctcccactca   16140
ccaggccctt agcctgcccc ttagcacaag agcacagccg gtctcaagtc taccctgctg   16200
taagcaaaca cttgcaacat catgctgacc tccaggccct gttgcatcag cgtgcccaca   16260
cttggtgccc agctggtact gagggtatca gggaacaggc cagtggtgga agggcggaca   16320 cttttgggttc cctggtttcc tggctcccaa tatctttccc aatggcatat ggggtctagc   16380
agcttggctc atttaactgt gaacctctac cctttagaat ctgggcctcc aggcttgctt   16440
ctgtgcaaaa tggcagataa ggctcaacct ttctttttt aacttcattg ttaaatatta    16500
ctccattaat acccatttac tgcagaaaag gtaggaaata cagataagca aaaggaaaa    16560 taaattaaaa tcctcatacc accatcatca agataattac tgtcaccatt ttggtatatt   16620
tcctcccaat acatatatta tctatatcgt atatacgaca aaaatggatc atactatgtt   16680
tcctgttctt ccctgtgtt agtcatctat tgctgtataa caaactgcct caaaacttag    16740
tggcttcacc tttccgtgta ttatgatgac aagaatgtgg tatgacactg tcttatatct   16800
ggatcatatg ctaaaagata gaaaatggtt tctaaactta tttgttctgt aataacaaaa   16860
ttttatttca taaagtgttt ttaaaaaaaa ccatagtagc ttgaaacaac aaaccttttgt   16920 tatctcacac agtttctgta ggtcaagaat tcagaagcag cttagctggg tggtctggct   16980
tggtgtctct cctgaggtca gggttttggc tggggctgca tcacctgaag gcttgactgg   17040
ggccagagga gctgcttcca aagtggtcca ctcacatggc tggcaagttg gagttgcgta   17100
ttggcaagag acttcgcttc ttctcaatgg atcttcccag agttcttgta ggcaacctca   17160
tagcatagca gttggcttcc cccagaggga acagtccagg agagaacaag gcagaaacca   17220
cagggtcttt tctggcttag gctccaaagt catactccac catttctgca ttatcatatt   17280
agttacacag gctagaccta ttctgcatgg aagagactat accatggggt gaataccaga   17340
```

```
agcagggcta attgaaggcc agcttcaagg gcggctacac attcccttc aacagtatgt    17400 catgaacatc tttccatgcc aatagagcag atgaatctta ccatttttaa tgactacatg    17460
taagtgtagc ataatttatt taaccaacct cctgtagttg ggtatgtggg ttgtgtctcg    17520
ttttttgata gtagaattaa tcatcttgaa tatccatcac caaacttgtc atattatttt    17580
cttttgatga atgaaaaaga aaatcaagtc atgtctgtca atcagaaccc tgagcaacta    17640
agaaatgggg gtaccactgg gacatagagc aaggtccctt ctgattctgc tcttgtcttt    17700
ctctccccat gaaatgggga gttcactatc tactgagaca tcctagccca cagctgcaca    17760
gttctgtctt tttagaaagc tctaagcaga aacaatgttc atccatcctc ctcgggacag    17820
cccttgagct actgaagact ctaagcatgt cctggtcatc ctccatgagc catcatctct    17880
gaggccctcc ccttcttggc ccctcttctc tggacaggtt ctggacagtc ttgcccttcc    17940
aaaattcctg gaaagcagga actgttcctg ctacaatgac tctcaactcc agtgcagtac    18000
agactgttgg tgtcacccct tatcctgaag aagaggcact gagacaggac aagggtgggt    18060
gcccaggagg gctggcatga gtcatgagaa tctggtcccg gagaattaga cggtgtgggg    18120
aagtaggggt gttgggccgc tttctggcct catggatgcc aatgaatatc agcaggtggc    18180
tcccagaaag gaactctagg ggatgcctgt tgctctaaat agaggctaga gagggcactg    18240
gcagttcagt caaccaagaa aggggggccca cttgcctcag cttcaggctt tgtacacatc    18300
ctcagccttt cttgagaact gaatttagat tctcctcccc tgtgctgtgt gcttggccca    18360
gaagaagggc aagtctcgct gggtggctgc ttcttggcct ggctgaacca gaaggcccca    18420
gtgccactcc aaacctgggt gtgagccctg cccccatgag caaacagtag ctcagagctg    18480
ggggctgtgg gggtcagtgg cctgtcacat gagatctgat gaggccatct ctgctctata    18540
ttgggaaagg gatcaattgt atcaagggct ttccttggga tgatcactct ggccattggc    18600
gagagacctg gcattctgac aaggcaccct ccatacccctg acccacttgc cagctccagc    18660
taattttagc aggctttggc aggtgccagc aagtacatag catgtggatg tcactcccag    18720
gtgagcccaa ggagaggcct gggccagagc ctggaagtca tggtctatgc ccatggaggc    18780
acccaaagca agcctgaggc ctggactttg cagtcacaaa attaagaatg ataccccttgt   18840 ttttttgtttg ttttttgatca gttggccacc ttcctccacc accccttccc caagttccat    18900 acagaccccct ggattgtatg aaatgcaaat cgaacctctc tgcagatgaa aatccactgg    18960
ggatcccctt gcctccaaga gcaagtccag acctgcacca gcgcgggcca ggccccctta    19020
ggaccccctc cctgtccaag ggcatttcag taagtgttct gtggccaagg cagcctggtg    19080
actttctgcc cgcacaaggc tgaggaatgg aagatgggta ggctggctct gcacacccc     19140 tcctgctggg cagcaatccc taccccatgt tcacagagtg tggccggctg ccccatggct    19200
ctgtccccgt ggccctgtca actgttaccc acatggccta ccctccctt ctgccctgcc     19260 tctgaccccca tggcagggg cagagtattt gagcagccgc caggctgagc cctttcagtg    19320
cagaagccct gggctgccag cctcaggcag ctctccatcc aagcagccgt tgctgccaca    19380
ggcgggcctt acgctccaag gctacagcat gtgctaggcc tcagcaggca ggagcatctc    19440
tgcctcccaa agcatctacc tcttagcccc tcggagagat ggcgatggat gtcacaagga    19500
gccaggccca gacagccttg actctggtaa gggtcacacc aaagttaggg actttgcact    19560
gggagagcag cacccagggc agggcccttg gttttgcaga ttaccaaaac taaggctggg    19620
ggcagggaag gcgagcaggc ttggggcacc ttggaaggag gcacatgggc cttggggtc     19680 ctggctaggg cagctgtgcc tgccactggc cctctgccca ccaccccctcc tcactgtggc    19740
```

```
tatccagtgt ccagcctctc gagggggttct agggtactta ttcctggagc taacggtgac   19800
ccaggacacc agtgtccggg gcctggcctg gggcttttat gggggggagct ggctggctgc   19860
ccagggctgt ctggctctct gggggctctg catggcattt ccaggggttg gtggatcagg   19920
gattctgtcc ctcaggagaa tgtgggcact agcccaaggc cactcacttc tgtgtacata   19980
gccacctgag ggcccaggaa tggagggggc caggctacag ctggacatct ggcactcgga   20040
tgggctctgg agccccagg cctgcagcat ctgcccaggg actgccctgg ccctttggcca   20100
tttcctcagg gacccacagc tccaccagcc ggcccctccc agtgctggaa tagacagttc   20160
ctcagtccac atctgccaaa ggcggcacta aaggcatcc tgccttttt actgcgttct    20220
ggaggtgggg tcacaaagca ctgctcactg cataaaaggg acagcatcct gcccctggca   20280
gccctgcctg accagctccg cctctcccac tgctatccaa cctgtacacc ctggtgacca   20340
tgtccaggcc agtggcctta aggactgtct ctgtactgat ggctccacat ctacctctcc   20400
agccagactc tcctctgaac tcgggcctca catggccaac tgctacttgg aacaaatcgc   20460
cccttggctg gcagatgtgt taacatgccc agaccaagat cccaactccc acaacccaac   20520
tcccaggtca gatggaacct cttcttccca ggcccttctg ttcctctcct cagcccctcc   20580
cacctccctt cagaataagt ctagactctt atcgctttca ccaagcctgc gcccagcatc   20640
cctgcacagg gattgttagg acagcctgac gccctgcttc cacctgccc caagatgccc    20700
ctgctctgca gcccggcgcc tccaggcttc tcacctcctg ctgctcacag ctcagcctca   20760
ctccctccct ccccgcctct gctccagcct cagtgcaggt cccctgctcc catcttctgg   20820
cagcagctgc ccgacctggt ccctcttcat ctgtccccat tccttcaccc cccagcctgt   20880
ccccaacttg actgaggttc tttcctgcag atccccgccc ttgagagggg ttggtcccac   20940
tgtcaactct gcttctgtgc cctgtgccgc acctggcatt cagtgagcat ctgctgaaga   21000
gatgagggtc agatgccctg cagggagtgt ggggcgtcc tcaggcaaga aaagttgtac   21060
gtttggctgt gggccctgat tatgtgtcct gtgacctctt gggtgaggtc agcaagagaa   21120
acctctgcaa gctggctggg gctgcctccc agaggctgcc aggggagggg acaggctctg   21180
tctgtgctct tcttccgagg ctacacctgg ggcgccaggc tctcagggct ccccaggtac   21240
caccacattt cctacactgc ttgggaaagc cctgtaagtt tgcacagaca cccagcatga   21300
ggctcgccag agagatactt gtagctgggg tctgggcacc aggaacagct tggtgctggg   21360
cctgaagtcg ggcaggatgc agcctggcca ggtgagagga aagcttggag ccagtgcctg   21420
ggttcaaaact cctctgtggc ctatggttct gtgggcttgg ggaagggttt gtacctctgt   21480
gtccagtttc ctcacttata aaaaaggag ataataaaag tacccatgtc ccagggtggc    21540
tgtagcaata atagggaggg gtgcccgagag caggtctggc acacaggaag tgtgcatcag   21600
cctcagtccc tgccattggg cttgtcctgg gagtctgtga agccaacctc tgctccacaa   21660
tgtgaccccc aggcttgtga gaccaagctg ggtcagagct tcctcctctg ggttgcacc   21720
aggaggggaa cttctgcagg cccagatgca ccctgaggaa agggcttgtt cccaccaaga   21780
acaaggctca cctttggagg atgctccca catgagaggt gaaccccag gtctactggt    21840
gactgcagcc tcggaagctg acagcatcta tcctccaacc catgcccact gggaagtgtg   21900
tgaggggtcc tcataggccc tgcggtgtgg acaatgcaga gaccctgtag catctggcta   21960
gggcggggcc cagataagag ccctgtgcca ggagagcctg gccggttctg ccactgtggg   22020
gagacaggct ccccacccc atgtcccctg cttccctgca gcccacagag aatacagacc    22080
```

| | | | | |
|---|---|---|---|---|
| tacttttaca | gaaatccaga | tttttgtgta | aaagtgtctc | tattttaagt | agattttaag | 22140 |
| tggtggcagc | aaatttaagc | ttttgagaat | attatacaga | acaaatcaga | ttcacaggcc | 22200 |
| agatgcaact | ttatttacag | aaatgggatc | aggtcctacc | tcaggtccca | tctcacgttt | 22260 |
| tcacttatgc | ctatacgtct | ccttcacggg | aaaggccaca | agaggccctg | cggtaagtgt | 22320 |
| cccggtgttg | atttaaagtc | cccaacagtg | aatatgaggg | tcctcactgt | tgcagcaaga | 22380 |
| ggatacccc | ctgtgtatct | tggaaatgcc | tgcagccctc | ttgctgcaga | acagattctt | 22440 |
| aggagagaaa | ctgtcagatc | aaagttaaac | ttagagaaac | tccaaattgc | cctctgaaca | 22500 |
| gacggtatca | gtttgacatc | atccaatacc | gggattcctc | ggggagaact | ttctggccta | 22560 |
| gaaggcagta | gagccaggac | ttcacccagt | cagtggcagg | gccacacgtg | ggccttgata | 22620 |
| cagaggggga | agacttgagc | ctcctcgaca | ccctacaggg | cccagcctcc | caacatgtga | 22680 |
| taagagaaac | aacagccaac | ttgtacctag | ctctccttat | tctccaaggg | ctgggccagt | 22740 |
| tctccccaca | gccctgcaag | ggaggatcac | tcaagggccc | caactgtctg | acaatacagc | 22800 |
| cacactctga | tcagccacct | gggcataggc | tccatgccat | tgtcctccgc | caagacctca | 22860 |
| gactgaaatg | ttggctcctc | ccatgaagaa | cctggggcca | aaggaccaga | gtccaggtcc | 22920 |
| gtggctgcca | ggatgggcca | cttggagaga | ggcacaaggg | tggtgccagg | caggtgtgag | 22980 |
| ggctggacct | ttgcaagagc | agcatcactt | ttgttgagag | cccacaggta | tcttataatt | 23040 |
| gggtcctagg | acttcctgcc | agtagccatt | gtgtgcatgg | atttgggtgc | tggcctcacc | 23100 |
| atggtgtgct | ggctgcccat | gcctgcaata | atgacttctg | taagccttc | ttcatctgca | 23160 |
| agatgggtgc | tgctggcacc | tcctcccgg | tgctgtggtg | acagggcata | gtgtgtgagg | 23220 |
| ctgctatgtg | aagcacctaa | tgcagggcct | ggcatatgga | ggaattcagc | aaatgacaga | 23280 |
| tgccttcaca | gttagttcct | ggcatcctct | acattggtgg | gtgtaggaaa | gaaagacaga | 23340 |
| ggaggcaaaa | gttgtagctg | tggggcattg | aggacagcct | ggattgttcc | acagagccct | 23400 |
| gaggacatct | ccaggggtgt | gctctgcagg | ggcagctgga | ttggagggtt | aggggtcggg | 23460 |
| gagggcgtgc | actcccaccc | atgctcacag | cctcggaaca | gtgcctgctc | agccaacatg | 23520 |
| ggtgtttgat | tctgtgtctt | ttgtcacaga | ctttatcagc | cccatccctt | tctgaccttg | 23580 |
| cctcagttta | aattttacat | gtggggcctc | attaagagac | atggttctta | actaaagatc | 23640 |
| tgtatccatt | aggaatgctt | tgggctgcag | gaagacaaac | acctgactca | ctgtggcata | 23700 |
| agtggtttgc | gtctgctccc | ataagctgca | cgtggagggt | ggatctggca | ttactctctc | 23760 |
| ttccctacat | ttgcagtatg | ctaacagctt | taacctccag | ccttgttct | tcatggttgc | 23820 |
| agggtggcta | tcacagcgct | ggccatcaca | tccttacaca | gctgtgttta | caaatttagg | 23880 |
| gggacattga | agctcctccc | ctgctaaaat | caggcttccc | ttcacctgtc | attggccaga | 23940 |
| actgggtgaa | atgcccaact | ctagaccgat | catcagtaag | aggagtatag | aattgctgtg | 24000 |
| cccaccttag | attaatcatg | gcgcaatgtg | ctccccatac | caacaaaatc | tgagttctag | 24060 |
| aaactgagga | agaagaggaa | aatggccgtc | ttgcctcctg | gctgggattc | agagcatctc | 24120 |
| caaccctctg | agcttatgtg | taagactgtg | ggcaaaagtg | tgtgagtttt | tgtggaatgg | 24180 |
| atccacggct | tttatcagag | catctttcct | tttttctttt | gattcaagat | gaaaatattc | 24240 |
| ttatgattat | tttctcacc | actgcccaga | gataaccagc | acattaacat | ggccttttct | 24300 |
| ccatgaatag | cactagggtg | cccagtggac | agacacatag | ctgtccacac | accagcttgc | 24360 |
| tggggatgca | taggcagagt | cacatctgca | ctcacgcct | gtcctcacac | tgccatgtgg | 24420 |
| agagccagca | gccacaccat | gggccgtcca | tgctcacggg | agtggcagta | tcagatctga | 24480 |

```
gcttcgtgtg cccaggcgtc tctcacatca gtgcataggg accctctttg ttctgtggcc    24540
cagtgtgccc atgccacaga tggcttcagt cagcagacac ctccttctag acactcacac    24600
tcactcctgg ctggcccctta gcacacctgt gcagacaggc ccatttattt tcttgtgtaa   24660
atcccaagta ggaggactgg gtctctctga cagcaatgcc agctgcctgg caccctccag    24720
acaggtggct caagcccac ctcgccagct ctcccagtta gccctccttt tccctggctc     24780
tgacctgagg gacgaagcag ggtgctacag gacgctgtgc cacagggata tcgtcaggga    24840
cagaagctac tctgccctct gctgctcacc cctccaacac gctgtgggct gcatttgttg    24900
agtggctggt accagactct gctcttctga ctttccagct ggttttacct gtagtaaagt    24960
ttgagaagat gggtcatcct gaccccgggg tcagaagaca aaggaggcc catggcgtgt     25020
gggggagatg cccgtgagg ccctcggtgt cagatgcct ggtgacagcc ccaccctgag      25080
gtccccagcc taccccctcc ccagcccgac tgctcccatc cccctccctg tgcaggtaga   25140
gcagatcctg gcagagttcc agctgcagga ggaggacctg aagaaggtga tgagacggat   25200
gcagaaggag atggaccgcg gcctgaggct ggagacccat gaagaggcca gtgtgaagat   25260
gctgcccacc tacgtgcgct ccaccccaga aggctcaggt accacatggt aaccggctcc   25320
tcatccagaa gcagctgtgg gctcagccct agctgggaga agcacccag gcactcccag    25380
actcacagcc agcccgagac agaatctcct ggggagcaat gaagtcctcg acttgggcca   25440
gttctcaccc ttggctcctc tggtccggcc ctggggcact cgggctcacc ctggagctgg   25500
caaacctcag gaaaactggc gtttaaatc tcactcctgg ccaggtgcag tggctcaccc    25560
ctgtaacttc aacactttgg gaggccaaag caggcggatc tcttgaggcc aggagtttga   25620
gaccagcctg cccaacatgg tgaaacccg tctctactaa aaatacaaaa attatccagg    25680
catggtggca cattcctgta gttccagcta ctcgggaggc tgaggcataa gaattgcttg   25740
aacccgggag gcgaggttg cagtgagcca aaatcgcgcc actgcactcc agcctggggt    25800
gacagggtga gacaccatct caaaaaaaaa aaaaaaaaa gacctcactg ctccccatgg   25860
gcacttaggg aactctccca gcccagttct gcagctgggc cattgcacta gatcctcagt   25920
tggtccctgg gctctcggtg actgtccagg gcaggagttt cccattgact tttccctggt   25980
tgaccttgga cccctccac agttgacact ggtgtcccca ggtgtctggt ggccccttgt    26040
ccagctccct tagtcccttg tgccttccct cctcctcttt gtaatatccg ggctcagtca   26100
cctgggccc acccagccca aggccagcct gtgggtgtcc ctgaggctga cacacttctc    26160
tctgtgcctt tagaagtcgg ggacttcctc tccctggacc tgggtggcac taacttcagg   26220
gtgatgctgg tgaaggtggg agaaggtgag gaggggcagt ggagcgtgaa gaccaaacac   26280
cagatgtact ccatccccga ggacgccatg accggcactg ctgagatggt gagcagcgca   26340
ggggccgggg cagggggcca aggccatgca ggatctcagg gcccagctag tcctgacggg   26400
aggtgccacc tgtctaccag gggtggggag agcgggggct ggaggaccac ccagcctcag   26460
aggcagctgg aggcctgggt gaacaggact ggccaacatg tccccaagtc ccacagtcac   26520
catctggcca gcattgagag gggaacgggc tgaggaagag ttagtggcaa gaggaacccc   26580
agccagtcac accttgtcca gtttaccaga ggaaaaacca atgtgtaaga acagaaatgt   26640
gacccggcag ccagtgcact gcccccctct ccaaaggcca cccctcaccc tccaccagca   26700
tgcacagaaa gtggggtgac agcaatcaca atgtctaccc aggcagcaag gacccctgac   26760
catggggagg actggggtgc agggaacata gaagcagaat gaggcctagg gggagttggg   26820
```

```
caaggccaga gccctagctg cagccaagca catggccaag gccagctcct ggaagggcag    26880
ggctccgagg caggaggcag gaggctgccc gtggctaccc gtcctcacac ccctgcagct    26940
tgctagtctg tctgtgggct gggtgtgaat caaggcagtg ggatggtgtg gggacctccc    27000
tggccccagc agccagtgag gagcctggtc agtcagcaga gcattcagca gtatccagtt    27060
ccatggagag gcccgtgtga ggggagtcgg ggctggtctt cagtaaggat gggtggccag    27120
ggcccctaga agtagaaaag gagactccgg gtgctggaga cagaaatcaa ggatgtgcct    27180
ccatgtggag cctcaggaat agctggccag gcctgaggct gaacctcaca aggttcagct    27240
gggagggcta ggctgacaga gcacagccgg gccaggacc agcctgccct gtgttgcctt     27300
gtcccgaggg ccactgtcag caggtctctg gcatggggga ggcttagggc ctgagcccaa    27360
caagcagcag cggaagagga gagggaaact gtggacaggc ctggcattca gtggccaggt    27420
gttgcagtgt ccctgaggaa tagcttggct tgaggccgtg gggagggctg ccggccagcg    27480 cacccccca tgccagatgg tcaccatggc gtgcatcttc cagctcttcg actacatctc     27540
tgagtgcatc tccgacttcc tggacaagca tcagatgaaa cacaagaagc tgcccctggg   27600
cttcaccttc tcctttcctg tgaggcacga agacatcgat aaggtgggcc gggtggaggg    27660
gcagaaggca gatgagggga ggcacaggca ccccagagga actctgcctt caaatgtagc    27720
ccccatacca tgtgctcaga agggagatct ggattcaaat tgtggccatg tcacctgcca    27780
cctctaatgc tgtggaaaag aagcatcaca ttagctaatt ctggctgtgc gccttgtgag    27840
gcaccagcta tgatcacccc actccagtgg aaagagcagc tggcagtagg gtgggctca    27900 aactcaggca gccgggctct gggtcacctg caggccacgg tcatgtcaca ctgcctctag    27960
ctgagtcaga aatgtgaagg aactgagatt ctacccttcc tgcaagctag caaagtggcc    28020
tgccagttac atctgtgcat gcacacacac acacagttat atatgcacac acataaaaca    28080
cgagaccttt gggtcaggga gaaagccaga tcctcactca cggcagaagc agcagccaaa    28140
gcaacatctc atgtggtttt ccaagcccca gtccctacag agacagagag gccaggtgg    28200 cacctgtgca tgcagcgggg taccttgcag gagggaaatc ctgattttac acaaagctgc    28260 tcccccacg ccctgccttg actctgggat gacgtctcag agctgtgcag tacaacattc     28320
ttaaattggc tgggactcag ccctgcagaa atatgatatc ttcaaggaga atcgttccca    28380
aaacctctca aagctatggg gctgctctga gcctgtttcc tcagctgtaa agtagggtgc    28440
atacttttat ggccctgtgc aggaggtagt gacaggccct agcaccctgc ctccagtata    28500
tgttagcagc cacgaggcct atctctcccc acagggcatc cttctcaact ggaccaaggg    28560
cttcaaggcc tcaggagcag aagggaacaa tgtcgtgggg cttctgcgag acgctatcaa    28620
acggagaggg gtgaggggc acctgtacct gccgggggg ctgccctggg ccacccaccc     28680
cagcactgcc tgcctttctc cttggcttcc agcactgcag cttctgtgct tcttggcagg    28740
actttgaaat ggatgtggtg gcaatggtga atgacacggt ggccacgatg atctcctgct    28800
actacgaaga ccatcagtgc gaggtcggca tgatcgtggg taagggctcc ttgcaccct    28860 gccccttcca gactgctgag gctccctgtg tacaacaggc ttcaagggcc ctgtggggtg    28920
aggaccaaac tacttaacaa ccggtgatgt cagagcagag cctggtgcta cagcctgggt    28980
ggtcttgggg tatcaagatg gaagcaccgt gtacagtagg aagcatttca acgccatgat    29040
gccacattcc tgcatcagat ggtatgccag ctgcatatcc acctcaccca tcaggattat    29100
aattaaaaca cttatctggt aaaattgacca actggacaga ttggtccaag tggaagagga    29160
taagcaaaag tggtaccatc tccacccgaa tggtctttcc acgggcctgc ccctgcccct    29220
```

```
gcccccaccc aaagtgaagg caggtaccag gaaagggagc agcagtccgc ccctcccagc   29280 agagggtct  tccacaccaa ctcggacctt tctcagaagt tccggaggtc attataacca   29340
gccttcactg aggagcaatc caatcagatc agttatctgc tgtgcgcaca gccgtgtggt   29400
tctatacttc tcttacttcc atttttcacct ttcagaagga acgttgtctt taaatccagc  29460
atctaaacgt gagccccagc catccctggc tgtgatcccc ccagcccttt ccaccctatc   29520
ctctggaact gcctggggct ccccaagaca cttccacatg aattcccacc aagccaagct   29580
gcagctgctg ggcccaggca taaccectcc tggggcagag gtggcaagga gtgacccacc   29640
actcacatct gccccacatc cactcttgac tctgctcagt gtttaaaaac atgtttataa   29700
caattaccaa gatctgaaaa ttaggagaat tcacatcaaa gtctggattt ctgtttgttc   29760
ataaaaaact agaaggcagc caggcaaggt ggctcacgcc agtaatccca acactttggg   29820
aggctaaggc aggcgggtca cttgaggtca ggatttgaag actagctggc caacaaggtg   29880
taacctcgtc tctactaaaa atacaaaaat tagctgggtg tgatggcgca tgcctgtaat   29940
cccaggtact caggagactg aggcaggaga attgcttaaa ccctggaggc agaggttgca   30000
gtgagccaag atcacgccac tgcactccag cctgggtgat ggagtgagtg agactctgtc   30060
tccaaataaa taaataaata aataaaaact ggaagtctaa gcatcactga gccctgattc   30120
ctatgtggca gctcgactga ccagcatttg agttgctgtc cctgacagct ttggggtgt   30180 gcagcccaca cagtcatgct agcttgaggc tctgctgtca gcagtttgaa actcttaata   30240
acttgtgaac aaaagactcc atgttgtcac tctgcacagg ggccagcaaa ttacaaaatt   30300
ccatatccgg aattgtctac aggagcctct gggctgctcc caagggccca caccatgcct   30360
tactcacttt ggggttgccat ccaaacatgt ctcatgacaa agaagctcaa acatgtgcat   30420
ggacagtgcc agaaaacaag ggtcgtacat agacaaaata aaatgataac gtcccacaac   30480
catttctttg atacacactg tttctctcag tcctcccaac cacctaggta acaggcaggg   30540
aaggtgttac tgttgcctgt taggaaagag gacagccctg aaagctgtcc ctggccactg   30600
aagcaaccca ggtcttccag ccccaggggag agccgccttt ccattgttcc agacaaagca   30660
gagacaggca tgggggagcg ggagagggac tcctgtgggc aggaaccagg ccctactccg   30720
gggcagtgca gctctcgctg acagtccccc cgacctccac cccaggcacg ggctgcaatg   30780
cctgctacat ggaggagatg cagaatgtgg agctggtgga gggggacgag ggccgcatgt   30840
gcgtcaatac cgagtggggc gccttcgggg actccggcga gctggacgag ttcctgctgg   30900
agtatgaccg cctggtggac gagagctctg caaaccccgg tcagcagctg taaggatgcc   30960
ccctcccccc acaacccagg ccctgggccg ctctggtgca gcggcagatg ggagccgggc   31020
cattgcagat aatgggcttg tttttaaaca actctgggga aaagcaaact gacaatccgt   31080
tcgtaagctc catcccttct gctcagtcat gacctgcccc tgtgagagat gaagggttag   31140
tcccagttgt gatgtgataa gcccagacct cttttccttcc gacaggtgat cgtgcatgca   31200
gaggaggctc tgagacgccc ccagcaaggt tcctgggttt aacccaacat tccccaaagt   31260
atgtatttgg ccacattcac agaaagaata ttagtctttt gtggaatgct gcgggttgac   31320
agtcacagct tggaaaccaa cccacagaga gctcatcatt aatcatggct atcacttgtt   31380
taccacctac tgtgccaggc ctatgctaat tactttatta gcgtcctctc tgccgctcgc   31440
aggcctctat tattataggt cagtagtatt cgatttattt aaattaaata cggaaggtca   31500
tagattaagc aagaaagtgc cagcaacatg gtgcgtgcct ctgactgggc actaaccctc   31560
```

```
caagtcttag tttcccaac cataactggc caatgaacag cagctctgga tgcagctaaa   31620
ggaagactga agctgtaggt cccgtgctcg gcgcagggcc ccctgcaagg aaggtttcgg   31680
agggactgga tggggtcttt gaactatctg tctttcccctt tactgcagtg ggcccagggg   31740
caggccaaag ttgctcccgt gattgacttg aacgtgcacg ttcctaatcc ctgacatttc   31800
taaagctctg gctcattaac gagggaaaga cgtgaaccag ctgggggagt ggggatcgca   31860
gtgcccacg tggccgcctc gtgacctcag tggggagcag tggggccggc tcccggcttc   31920
cacctgcatg aggggccctc cctcgtgcct gctgatgtaa tggacctgcc ctatgtccag   31980
gtatgagaag ctcataggtg gcaagtacat gggcgagctg gtgcggcttg tgctgctcag   32040
gctcgtggac gaaaacctgc tcttccacgg ggaggcctcc gagcagctgc gcacacgcgg   32100
agccttcgag acgcgcttcg tgtcgcaggt ggagaggtgt gcggaggagg agggtgggtg   32160
caaagggcag gggctgggga cgcccgggca ctgcagactt ggtctcaggg cgacgctgag   32220
tcccaggccc ggggcgcagg gatgggaaac tagggcctgg ggcgggattc cgggcgtggg   32280
cggggcccgg ggcggggcac aggggggcggg ggagtggggcg gggcccgagg ccgggcgctg   32340
gaggcgaggg cggggcaggg acgggtccaa gggcaggagg ctgggacagg acggggatgc   32400
aaagggaggg gcggggcccg agacggggag gaggggggagg gcccaagggg aggaggcggg   32460
gtccggacgg ggatgccaag agcagggatg ggagcgagcc tgcgtccggg cactggtccc   32520
catccgtgag tcccctcggt gctccctgcc cgccgtggcc atcctctcac atcactcaca   32580
accccaaggc gcggcatggt tgacaccccc acgttaggac ggagaccctg ggcttagtta   32640
gagggggcag tactaaccag tccctggcgg aaacgctttg gctgggtgag gtgagcggga   32700
tcgcccccat ttctccagag aggggtcccg gctcagcgag ggaaagaggc cgccgctggg   32760
gggacgctg gccggggccc ctccctggag aacgagaggc cgccgctgga gggggatgga   32820
ctgtcggagc gacactcagc gaccgcccta cctcctcccg ccccgcagcg acacgggcga   32880
ccgcaagcag atctacaaca tcctgagcac gctggggctg cgaccctcga ccaccgactg   32940
cgacatcgtg cgccgcgcct gcgagagcgt gtctacgcgc gctgcgcaca tgtgctcggc   33000
gggggctggcg ggcgtcatca accgcatgcg cgagagccgc agcgaggacg taatgcgcat   33060
cactgtgggc gtggatggct ccgtgtacaa gctgcacccc aggtgagccc gccccgctct   33120
ctccctggta aagtgggggcc caaaaagcgc gcgctccaag gttccttgcg gttcccaagc   33180
tccaagattt cgtagtcctc ttctcgtccc ccttggccta gatttggggg aagggtcgac   33240
tgcgtgcagg gcgcccggta atgaatgtgg aggatgaggt ggggaggaggg acggcagccc   33300
tgcttctctt ctgcccagct tcaaggagcg gttccatgcc agcgtgcgca ggctgacgcc   33360
cagctgcgag atcaccttca tcgagtcgga ggagggcagt ggccggggcg cggccctggt   33420
ctcggcggtg gcctgtaaga aggcctgtat gctgggccag tgagagcagt ggccgcaagc   33480
gcagggagga tgccacagcc ccacagcacc caggctccat ggggaagtgc tcccacacg   33540
tgctcgcagc ctggcggggc aggaggcctg gccttgtcag gacccaggcc gctgccata   33600
ccgctgggga acagagcggg cctcttccct cagttttcg gtgggacagc cccagggccc   33660
taacgggggt gcggcaggag caggaacaga gactctggaa gcccccccacc tttctcgctg   33720
gaatcaattt cccagaaggg agttgctcac tcaggacttt gatgcatttc cacactgtca   33780
gagctgttgg cctcgcctgg gcccaggctc tgggaagggg tgccctctgg atcctgctgt   33840
ggcctcactt ccctggggaac tcatcctgtg tggggaggca gctccaacag cttgaccaga   33900
cctagacctg ggccaaaagg gcagccaggg gctgctcatc acccagtcct ggccattttc   33960
```

```
ttgcctgagg ctcaagaggc ccagggagca atgggagggg gctccatgga ggaggtgtcc    34020
caagctttga atacccccag agaccttttc tctcccatac catcactgag tggcttgtga    34080
ttctgggatg gaccctcgca gcaggtgcaa gagacagagc ccccaagcct ctgcccaag     34140 gggcccacaa aggggagaag ggccagccct acatcttcag ctcccatagc gctggctcag    34200
gaagaaaccc caagcagcat tcagcacacc ccaagggaca accccatcat atgacatgcc    34260
accctctcca tgcccaacct aagattgtgt gggtttttta attaaaaatg ttaaaagttt    34320
taaacatggc ctgtccactg ttctttgact tctgtgcatt aggactgtgg ggacaatcta    34380
taaagagtct gcgtcacatg catgaagaca cttcagtatc tcggcaatgc cctccagaca    34440
gctcctccag ccatctgtgc caaggggagt gtgaggagtg acagaccagg ctgtaggaac    34500
aggaatgggg tgtcatgggg gatggcagag cagtggacag tacactgcct ggcccgggcc    34560
cctgcttgcc tgcccatgga atgtgtgcag agggagtgcc aggccaggtg ctgctctgga    34620
gaagtggggg aatgaggctg gtcctgctgc aggtcagtct cagcaccgtc ctgtccagtc    34680
agagtcactt aggtttgcca gtgagtaggg gcccagatac atgttggatt tctaaggtcc    34740
ctccagatgc tcctgtcagt ggaacgccta tttagagtta gccaagcgta ggcataatgc    34800
catctttctg cagcataaaa tacagtgaca tagaaacata tttgtgtgat tttcatgcat    34860 tcctttttg atgagagata ttacccagct aattaggaac aactgttttg tttccttcag    34920
atcataaccc aaagttgtga ttttgaaaag tcatgtcccc cttcagattt cttgttttct    34980
gctacttctc atgtggaatt gctttggctc ttcttagttc tcttgagtct aaattattcc    35040
ttataagttg gtgcaagcat ctgattattt tgttatcatt actgttatgc tcaagcattc    35100
acagagtgga acacatttta atatcaattg ctttctattt ctcctttata ttacagttca    35160
ggacattgta ttaattatta aaattctatt cgtaggtagg ttatatgact gaattgaaat    35220
agataaaatg aatttctttt ctagataaca aggaggtgt cataaaacac ttgttatggg     35280
ccagtgtgat ggctcatgcc tataatctca gtgctttgag aggctgaggt ggaggattgc    35340
ttgaggccag gaatttgaga ccagcctggg gcaacatagc aagacccat ctcttaaaaa     35400 aaaaagggtg gggcggggggg gcactgctgg gcgcggtggc tcatgcctgt aatcccagca    35460
ctttgggaag ccaaagcagg tggatcaaaa ggtcaggagt tcgagatcag cctggccaac    35520
atggtgaaac cccaactcta ctaaaaatac aaaaattagc cgggcatgat ggcgggtgct    35580
tataatccca gctactcagg aggctgaggc agaagaattg cttgaaccca ggaggcggag    35640
gttgcagtga gcagagattg caccactgca ctccagcctg gcaacagag cgaaactctg     35700 tctcaaaaat gaattaatta attaaaaaaa gaaaaaaaaa acactgggca gggtggtgtg    35760
cacctgtagt cccaactact ccagaggctg aggcaggaag gagcacttga gcccaggagg    35820
ttgtctgcag tgagctctac tcatgccact gcactccagc ctgggtgaca gagctcagtg    35880
gcttacacct gtaatcctag cactttggga ggctgaagca ggcagatcac ctaagatcag    35940
gagttcgaga ccggctggcc aacatgataa aaccccgtct ttactaaaaa taaaataaaa    36000 taaaaatat atataaaaat tagctgggtg tggtggcaca tgcctataat cccagctgct    36060
tgggaggctg aggaacaaga atggcttgaa cccggggagg agaggtggca gtgagctgag    36120
atcgcgccac tgcactccag cctgtgcgag agtgagactc tgtctcaaaa aaaaaaaagg    36180
gaatttaaga aatttaaaag aaaactcttg ttatataaaa agggtattgg gtctgacaga    36240
taagagctcc tgcactctac cagccagcta ctgacagaca taggtctggc tccagtggag    36300
```

```
gggcagcagc cagtgagccc agcctgggt ggcccactcc tgctgcctcc aggatgtccc     36360
ctgtttcccc agcccctctg ctgtgccctc ggccccagaa gctggcgaga ctgcttctct     36420
ggaacagcat cacgcaggcc tgcccatcgg cccactgtgc accaggcctt ctgggatac     36480
agatgtcaac caggtggggt gctcaggagg ggcacagaag ccaggaatga caaacacatc     36540
agccaccagg caaatgggaa atgtgcccca gaagctccct gctgaggatg ttagggagag     36600
cattctgaag tagtgtggtt gagatgaggc ttgaggaagg caaggctcca acagcaggg     36660
cagactggga gcaaggtaga ctgcatggga gggcagctga tggagctcct taaccctctg     36720
gaattgcccc aaagccaagc aaagtgttct tcttggggtc acagctagct cagggatgcc     36780
ttctgcccct tggtcagagg ggcaaaaggt cagagcctag ggtcaccaaa acctctggga     36840
agccccgggg gtctcaggcc acagaccatc ctcagaacta cacactgccc tcccatgcct     36900
ggcgggggcc ctggactggc cctcaccagc tgtcttcttg cactggccag ggttctggct     36960
ggactggcaa ggaggggtgg tcagatacag gagtaactgg atcccttcat caggacctag     37020
ggtggtgaga gctttgagcc tgctctgctc caggcagaca ttgtgtctgg ccctgccagg     37080
atggatagac agcaggatgt tacacgttga ggacatgaag gtcatcagga atgtggctgg     37140
aatctgttag gcctccccca gcccaggcgg gggctgccaa gtttgggcct atcctctgtt     37200
cctctcctta tttggacctt caggtgataa ggctgagaca taaaggaggc tgggccctgc     37260
caccacgaca gcagccacac ctctgcagag agaatggtga gtgcctgctg gggaagaaag     37320
gctagcggtc tcccaggtgc tggcctttgg gctgggggag cagagttttc tgtgcttgtg     37380
ttgggttgag ggtggtcccc agggagagga agaggatcct ggccctggct ctcctgggaa     37440
tgctctggga ctgtgcatga tgggtggggt ggggagactc tgaggagttg gggagaggac     37500
ccctccctac tcacagtgtt gcaggccagc aggaaggcgg ggacccgggg caaggtggca     37560
gccaccaagc aggcccaacg tggttcttcc aacgtctttt ccatgtttga acaagcccag     37620
atacaggagt tcaaagaagt gagtgcccac tcccagtagc ctcagatccc atcctggccc     37680
ccccacccca ccccacatac atacccccct tctaccctga ccttgcctct cacaccaccc     37740
aggtctctcc cccacctccc accttcccta gagctggggg ctgctcccac ctgaaggccc     37800
ccatcccaca ggccttcagc tgtatcgacc agaatcgtga tggcatcatc tgcaaggcag     37860
acctgaggga gacctactcc cagctgggtg cgtgcaccca cctcccaccc tgcgcactgg     37920
ggtccctact ctgagctgct gggcgggtgg gagtggctgg ggggacagga ctctgctccc     37980
ctgcttcccc tcctcccgt ctcctcacac tgccctcccc ccttgtcac gccttgcttc     38040
cacttcacct tcccgaccca cagctgcctc tgcccctcca gcccctgtgg ccaggatgga     38100
gggagggcgg cctgggcctt ctgggggaca cccagggtcc ctgtgtgcac ctcatgcccc     38160
accccacca gggaaggtga gtgtcccaga ggaggagctg gacgccatgc tgcaagaggg     38220
caagggcccc atcaacttca ccgtcttcct cacgctcttt ggggagaagc tcaatggtga     38280
gcctgggaca gagctgggca cccttggcca ggcagggagc ctgcaccctg cctgaacccc     38340
acctgaaccc tgcctgaacc ccacctgaac cttacatgaa ccccacctga accctaactg     38400
aaccccacct ggaccacct ggactcttcc tggccatgac ccattccaag cacatcctct     38460
gccccagaat cccatgtgca ctggtcaccc cagtgctgac ttggagccag gaaatgtgcc     38520
ttcagccccc accccaaat tccagtctcc cagccaagct gcccgcctca ggaggatgac     38580
cattcccagc cccactgatc cccgagaaac attttatgtt agggaatacc cccacctctt     38640
ctgggatgtg ggaggctcct catgcagccc agttcctcct gcgggggacc tgggatgctg     38700
```

```
gagacatgga tgctcacctg gctgcctcgg ccttccaggg acagacccccg aggaagccat   38760
cctgagtgcc ttccgcatgt ttgacccag cggcaaaggg gtggtgaaca aggatgagta    38820
agtatgggcc cagccagatg aggagcaccg tggtggaagc agagagcggg gtgaggcccc   38880
tagtgagggg ggctgcctgt gcttcggggc cttacactgc tctttggggt gcagccaacc   38940
cttccctgcg ccatgggagc ctccgtaccc accttccctg tgcagtcact cccccgcagt   39000
ctcctgctca gaccctcctc accccccagg ttcaagcagc ttctcctgac ccaggcagac   39060
aagttctctc cagctgaggt gaggctgccc agccccttca atactcatcc ccagcacctt   39120
ctctgggcct tcacccatga cccagagccc agtaccagtg aggcagttgc tggaagggtg   39180
agccgagggc ccttctggag gaggtgccat ctctgttgag acctagaggg taaagatgtg   39240
gagtcagaaa agagggcagg gtgcgccagg cagggagact gtgcacagac ctgggggaa    39300
gtggataggg agaggtttcg tacactcggg gtgggcctgt gcctgtggct ggagggggcgt  39360
cctttgcctc ttggcccaca tttgcactga ctcctcactc tgcccagagt cagccaagag   39420
aaaaacatta acccagagtc tggggtctag ggttgaaaag ctaaggcaaa aagcacagat   39480
gcaggggggca gacagaaagg ccacaggact caggtgaggt ctctgccggg ctgggccagg   39540
agccagggga ctgccactca ccagtgtccc ctgcaggtgg agcagatgtt cgccctgaca   39600
cccatggacc tggcggggaa catcgactac aagtcactgt gctacatcat cacccatgga   39660
gacgagaaag aggaatgagg ggcagggcca ggcccacggg ggggcacctc aataaactct   39720
gttgcaaaat tggaattgct gtggtgtctt gtctgtgaca gatgggttgg ggaccagcca   39780
aggggggatcc cagggtctca gtgcgcacat caccatgatc atggccacca tctacctcct  39840
gggagctggc ccctcgccag ctcaccttga ttcactccca tgatgccaag tgaagtgtga   39900
actatgatca tgcctagttt acagatgagg acactgaggc ccagaaagtg tgagcatctt   39960
accaaggcca gccctctaga agaggagatg gtgggatta caccacctcc accaagccca   40020
ggaatgagcc acaaagtggg cactgcccag ctacttgggg ctgtgcagag aagaggctgc   40080
ttgctgggca ctcagcaaac tctgcccaac agcccagcgg gtgggcagca gccctgggac   40140
ccccacaccc aaccacacag cctcccctgg cccactgctc gcaccccatc tcaatacact   40200
ggcttgggtg cctccctgca tgggccccttt gtgaaaggca gagaggtacc catttgaaac  40260
acaaccagct tctcattgca aatacaggca aggcactaag acatgaggaa catggacacc   40320
aaagcagggg ccaggtaaca tgcaaatttc tagaggaaat gcccagaacc tggcatcatg   40380
cctcctgagc ccctcatgcg ccgtgagggg taagagggtc agacagctgg agtgtaggga   40440
gacgacttct caggagagaa tagttagtgc tcccgtcacc cttcatctga gaacccaaga   40500
gctagaggag aaagtgatcc tcatgagtac cagaggagca gcaggggaca tccaaagcac   40560
cagagagaga aacagagaca gagacagg cagtgacagc tcaaacctca gccagatcca    40620
gagcatacaa agtctcctgc ctacaggaca gcccagtaag agctctcagc ttgcctcctt   40680
ccctccccac aagccctgct gcaatccctg tacctggggg tcagtgggaa ggaggtgagc   40740
gagaaaggag gggcacccct tcctgaaggc cccaagagga aaggcgtttt cacccagaca   40800
ggtgttcagt tttgatttta tctggcgcct ggcaatttaa ttactaaatt gaaacttgag   40860
actttctgga attatggcat tttctgttgc ttagagagat tacaaaagtc acgaactgcc   40920
tgagtttcca tcctgaaagc aggccaccag cccactccac tgaccatgct ggaacagtgg   40980
atgaacaaaa tcaagtacca ttaggattct accacatgag tctgcttgtt caacaagctg   41040
```

```
atttcataaa gtaagggatc atgttataat ccaagctcta caggggtaaa ttgtgaaaga   41100
ctaaaatgaa ccaaaaagat cataggtgtc cagttatctg atttgatggg gtgtctgaac   41160
cttttgttat ctttgagctg tttcaaaact ctctaaatta ttattattat ttttgagaca   41220
gagtctctct ctgtcaccca ggctggagtg cagtggcatg atctcagctc actgcaacct   41280
ccacctccca ggttcaagtg attctcatgc ctcaccctcc caagtagcta gtattacaga   41340
tgggcacacc ttgcctggct aattttttgta ttttttaatag agacgtggtt tcaccatgtt   41400
agccaggctg gtctcgaact cctgacctcc gttgatccac ctgcctctgc ctcccaaagt   41460
gctgggatta caggggtgag ccaccgtgcc ctgccacaac tctaaattat aactaatagc   41520
aaggcaatgg ttcttctcta ttaacgtgca aataaatgtt gtccagtgga agcacaactg   41580 attttccct tctctgtgga agaagccaat tttgcatcta ttaagcaaat tcatctgggc    41640
attcctaacc gtctacacat gcaccggctc tttgaattct tctctgaacc aggcccagga   41700
ataagccaca agatgagcac tgcccagctc cttgggctgt cacatcttat tgattcccac   41760
atgaattcac aagtaaataa atatttggc ggttgttcac ttagtatgca agtcaatatt    41820
ttgctttaaa aatattatcc tttcacactc ctgatatagt tgtctgataa ggttagtcct   41880
tcccacacca aaactgcctg tattagtgtt gtttggaata aactgagggt agaatgtata   41940
tggtgtgtgt atgtggtgtg tgtgtttgtg tgtgtgtgtg tgtgagagag agagagagac   42000
aaaagagaga gacagaagga tagagagaaa cagatgggca cagacccagg acatgagttc   42060
agcctacact gaccaatatg acagccactg gccacttgaa atgtggtgtg agttgggata   42120
tgccaaaagt gtaaaatgca cacaatattt tgaagatttc atacaaaaaa gaatgcaaac   42180
atctcattaa taactttat atagatcaca tgttgaaatg ataatgtttt ggatattaga    42240
ttattactaa aattaatttc acctatttct tttcactttt taaatgtggc tactagaata   42300
tttagaattc cataagtggc ttgcatttct ggctttcact cctgttggaa agcactgagt   42360
tagactgtgt agtacgtcta tttaagactg cagtttccag gccgaacacc gtggctcacg   42420
cctataatcc cagcactttg ggaggccgag gcgggcagat cacctgaggt caggagtttg   42480
agataagcct ggctaacgtg gtgaaaccct gtctctacta aaaatacaga aattagccag   42540
gtgtggtagt gcatgcctgt agtcccagct actagggagg ctgaggcagg agaatctctt   42600
gaacccagaa ggggaggttg cagtgagcca agatcaagcc actgcactcc agcctagatg   42660
acagagcaag actccatctc aaaaaaaaaa aagtagaata aaaataaata aataaataaa   42720
gactgcagtt tctgggagac tctgaggcag gcattagcct tctctgcaga gagtacttgc   42780
agcagggagc agcagttttg atgtcctcaa aaggagccaa tttcatttgg gtagggttgc   42840
ctctgagtat tctagcagta cagacagaaa ggagagaagg ctgtttccag aaagcagaga   42900
tcatacgaat tacttgtgag accaaacttg ttcctcaggt gaagctcagg catcccttat   42960
gtggagtgtc taacagtcta cacctgagga tgttggacat aagggggtgt gaggtgggca   43020
tggctgggga gagctctggg aggggaaaa ccagctccat gttgtccacc cactgaaagg    43080
aaagctccct ctgggggagg tagatgcccc ctggccaggc ctgcagggcc ctgctcactg   43140
tgagccctgt gtggtcctgg cctggtccc accagccatt gccaggcaac agctcccagt    43200
tggaaaacag agcaaggctc cctcttagaa aaaaaaaaa gaaagaaaga aagaaaaga    43260 aatacaacag gtaactaagc atgacggctc acgcctgaaa tcccagctac ttgggaggcc   43320
aaggcagagg attgcttgag actggaggt tgaggcagca gtgagccagg attctgcaat    43380
tgcactccag cctgggtgac aaagtgagac cctagtaaaa aaaaaaaaaa tagagacaga   43440
```

```
gaaagaaaga catgcaacag ggccaggcgc agtgactcat acctgtgatc ccaacacttt   43500
gggaggcaga gaagggagga ttgcttaaga ccaggagtgc aagaccaacc tgggcaacat   43560
ggcaaaaacc catctcttca aaaaataaaa aaattagcct gttgtggtgg tgcgcaccta   43620
tagtcccaga tattcaggga gcttgaacca ggtccaggct gcagtaagcc atgatcgtgc   43680
cactgcactc cagcctgggt gacagagcga gaccttgtga gaaagaaaag aaagaaggga   43740
aggaaggaag gagggaagga gggaaggagg gaggaaggga ggaaggaaga atataggacc   43800
caaaggccta aatgccccta ctgtgcccca gttctgcgtg actcaggacc agcctcctcc   43860
acactcccac caccacaacc ctgcacccta cttgttcctg ggggcccaa ggggagcctc    43920 accagaagcc tcctcataaa cccactgccc cttaccttc ctgtctttct agaagcctca    43980
gaagccttgc cactctaagg cacctccat ctgagccaag gcgctcgctc cagatgtccc     44040
agagctcctg gtcctgggtg tccctgccac acaaccccc atggagccct gctctggctc     44100
aagccccctg actgtgcatg agcaggcctg ttgccctcac tgggactgtc cagagccttc   44160
ccatctctct ggagggactt ccatcagttt ctgccccttc tcctctgcca agaactcacg   44220
ttcagtctga tagcagaaga atcatctggc accctcctga atggaaccca gagtacctcc   44280
tttgtggacc ggtctctgga ttttccccac tctctccctt cagccatgct gatggcagag   44340
aaggtaagaa cttccagccc acttctctgg cgagggggaac ttgtcatctg ggtctgcaga   44400
gaaggttcca ccttatgctc atagtacatt atctttacta tgtactagga tatcacattt   44460
aaaaggacaa aaaaggccag gcagtggctc atgcttgtaa tcctagcact ttgggaggct   44520
gaggcaggtg gattacctga ggccaggagt tcaagaccag cctgaccaac atggcgaaac   44580
cccatctcta ttaaaaatac aaaaattagc tgggtgtcgt ggcatgtgcc tacaatccca   44640
actacttggg aggctgaagc aagagaatca cttgaaccca ggaggcagag gatgcagtga   44700
gctgagatcg tgccactgca caccagcctg ggcgacaaac cgagactcca tctcaaaaaa   44760
taataataat aaaatacaac aaaataaaag aacaaaaaaa agaaatgta aaatacttga    44820 aggggcttgt ataacattaa taggattgac agtatctgct ttccaggctg aagtgattca   44880
ttcattattc tagacgtctt tagtcctttg caatttgtgg taattaggct tttcttttta   44940
acattaaaaa tatacaaaaa taaaaggcaa aaaaagcatc atcccattag tctgaccttc   45000
ccctcctcca tccctgcccc aacaccctga agaccctgga tgcaaacaaa ggcccgaggg   45060
agcctcttcc ctcgcagtgc aggcctcacc tggggctcag agtcagaatc tgcattttat   45120
tccctaggac aacctctagt cagggcagag gccggctgtg ctgcccaagt gccctaaccc   45180
tagctttgag gcaccagaag ggcaaatgca aattaaaaat gagaataagt ttattctcct   45240
tggtgaaaaa aaaaaaaaaa gactttcccc tctcctttt ctttagaaaa tctatcattg    45300
caagttcctt cctggacttt ttttatgtag atctgttcaa aagctaaata agcctctttc   45360
aagtttcaca tcccaggaat gtctccttaa ggacctagga gccaccattt gaagtgtaat   45420
caccaaggga gatacatcct tatctcccag tttccgtggg caaaggggag cctaacttta   45480
gcccggtgcc tagctcaagt tgcaaacaca cttccagtct taaaggaatg aatttatttt   45540 ttttcctttta ggcaaaccca ggtagccacc acagttacct ggggattcac agagaactgt   45600
gtgtgaccac tggtgctgtc aagtcctctt acctgagcac ctgtgacgtt tcccttgaga   45660
acgtgtacgg gatgggttgc acctggttat atacaagcgt gagacttctt tctgcctttg   45720
taatttatta gcagattatc tgtgatgagc atcgcaatct gtttaatgcc tattcaataa   45780
```

```
ttaaattttt ctttctcttc ttttgtggaa aggttttctg cattggcagg agattttgt    45840 tttcgattat gtccccaaca tgcctgatgt tccacccctc aagagcctca gccttgccca    45900
gggagggcat gggggtgagt ggcctctccc acagagagtg ctggccaagt tggcccaggt    45960
gcgcagcaag ggctgctgcc                                                45980

<210> SEQ ID NO 7
<211> LENGTH: 18999
<212> TYPE: DNA
<213> ORGANISM: Homo sapiens

<400> SEQUENCE: 7
ccctcctcca tccctgcccc aacaccctga agaccctgga tgcaaacaaa ggcccgaggg      60
agcctcttcc ctcgcagtgc aggcctcacc tggggctcag agtcagaatc tgcattttat     120
tccctaggac aacctctagt cagggcagag gccggctgtg ctgcccaagt gccctaaccc     180
tagctttgag gcaccagaag ggcaaatgca aattaaaaat gagaataagt ttattctcct     240
tggtgaaaaa aaaaaaaaaa gactttcccc tctccttttt ctttagaaaa tctatcattg     300
caagttcctt cctggacttt ttttatgtag atctgttcaa aagctaaata agcctctttc     360
aagtttcaca tcccaggaat gtctccttaa ggacctagga gccaccattt gaagtgtaat     420
caccaaggga gatacatcct tatctcccag tttccgtggg caaggggag cctaacttta      480 gcccggtgcc tagctcaagt tgcaaacaca cttccagtct taaggaatg aatttatttt      540 ttttcctttta ggcaaaccca ggtagccacc acagttacct ggggattcac agagaactgt    600
gtgtgaccac tggtgctgtc aagtcctctt acctgagcac ctgtgacgtt tcccttgaga    660
acgtgtacgg gatgggttgc acctggttat atacaagcgt gagacttctt tctgcctttg    720
taatttatta gcagattatc tgtgatgagc atcgcaatct gtttaatgcc tattcaataa    780
ttaaattttt ctttctcttc ttttgtggaa aggttttctg cattggcagg agattttgt     840 tttcgattat gtccccaaca tgcctgatgt tccacccctc aagagcctca gccttgccca    900
gggagggcat gggggtgagt ggcctctccc acagagagtg ctggccaagt tggcccaggt    960
gcgcagcaag ggctgctgcc caaaggctcc ctcctggttg gcatgggtcg ggaccctgtt   1020
gtgttgtgtt ttcgctcttt ttcgtagagt tcaagggggt cctgctatgt tgtccagact   1080
ggtcttgaac tgacctcaag ggatcctctc gtctcagcct cccaaagtgc tgggattact   1140
gtgcccagct ttgtgttgta ttttctgatc ttatcctgca acctcttgag cccccaacct   1200 gggcccagt tcctgctgtg ccccagcctg ccagccctct ctctctgcat attctttctt    1260
tagctgagtt aacaccactg ataaggttaa agacaggctc ttaaatttct gccctggcat   1320
gagaaatatg tgacccacat gcttctccag cttagctgtc cagtgtaact gtcagggact   1380
gatgggcgcg tgctggccca cagcccacct cagtcctgac cctccctgac aggctgagag   1440
aggccccagc ctgaacctgg actccccat gttctgatat tcctgcacaa gagtgcagag   1500
gcctggttaa gctggagaaa cataaggaat aggtaggtct gcacacactc acctcttcct    1560
ttgcagtgaa ccttctagaa tcttctagat ggaaaagctg ggggtgtgga ggtgtaggga   1620
taggacagct gggggaggcc ttggccaagg tcaaggagta gcccagtct ccctctctgt    1680 gtgcctgtct gggactcggt ttcctgtctg tgaagcaggg ctggacggga tattgacagc    1740
acctgatggt cattgagctc ctctgcccca ggcactcagc tgctgggcac agtgcacacg   1800
tggcagtccg gtgccctctc acgctccgtg atgactgagt ctgtagttac accccctggcc   1860 tcagaataaa gactacactt tctgcctccc tcactggcag gtatgactag gtgtggtggc    1920
```

```
agttttctcc ttaagagaca gatgtttgtg cctccctcca acccgctggc taacacctag    1980
ctggcacaca gcctcctggg gctatgaaga tgagggccac agccacaggg tgggggagcc    2040
gtgagctggg tctggctgcg tctctgacat atggggcat cacacatcac ctctacctcc     2100
catcgaatgc tacacgaaga gaacaaactc cacctgatgg aagctgctgt tgtttgaagt    2160 cttctcatgct cacaacagaa cctaacccca accaatacag tatgagtatt ggccccacgt   2220
ggttaagcaa gctgtccaag gttacacaca gctgggaggg ggtggagctg ggtttgagcc    2280
tgttattgac ctttgtgcag acagacctca gagcagagca caaggcagca aggctgtggg    2340 tctgggctc cctctccagg agaatcaact ggctgcacac agcctggaga gcccatgggc     2400
aacctgagtc cttgcacctg gaagtttctg tgtcccacac atatccagga gcttaaaatg    2460
aagatgtctg aattacccaa cctcttgata gcaccaaccc aaccttccca gcctcctctt    2520
ctgaggtcag cccagagcaa gccccttgca aagctgattt aactcagaac cactgggcat    2580
acccacaggg cagtgaccct gcagccctcg atcaaatgtg cagatggact tgggggtggg    2640
ctggtacccc agatggcctc attctcccag ggttgcagag cccctgaaag ccacagccct    2700
gtgtgcacac cactggggag tcatcacagg atacttcaag aattcagtgc caggcaaggt    2760
ggctcatggc tgtaatccca gcacttcggg aggctgaagc gggcagatca cctgaggtca    2820
ggagctagag accaccctgg tcaacatagg gaaacccat ctctactaaa aatacaaaaa      2880
ttatctgggc gtggtggcgg gtgcctgtaa tcccagctac tcaggaggct gagaccggaa    2940
aatcgcttga gcctgggagg cagaggttgc agtgagctga gattgcactg ctgcactcca    3000
gcttggggga cagagtaaga ctccatctca gaaaaaagag ttctgtgtat catttaatgt    3060
ggagatcctc ccatcacgag gatgaggctg tttctctact ccccagatct gggctggcct    3120
gtggtttgtt gacctcagcc ttgtagttct cactttcctg gaacctgaat gccaccacgc    3180
gacatccata agacaaagcc caggataaaa gatcacttgg agagacaggc ctggcctggc    3240
accaccccgg ctgaggctgg acccctggga aggagactct gatggacctc agacccagt     3300 caaatgacca cttccaaggt caggcaagaa gggacaaaga gccactggct cagcccacag    3360
catctgagaa ataagaaacc gctgcatttt ttgagccagt aagatttgac aggtttgttt    3420
tgcagcaata gatgagtggt acctcatctt agcccatgtt ctgatgaaga caaacagtag    3480
cattgacaaa gttttaagaa aagttaacca aaaactggga ttcctttctt cattttgacc    3540
ctttgttaca agaaacagag gcccacccca ccagactcac tgttcactgg tccctgagtg    3600
cctgtgagtc tcagtgggag ttaccttgag accagccctt ctgagtggag ggtgctgggt    3660
gctgaggtca agtcgagctc agtccaggct aaaaggagag cagctctggc caggctgtca    3720
gggctgtggc ctccccaaga acctcctacc ctggcccctc caggctttgc tgctatggtt    3780
gtgtgagggg agttgctgtc ccagcattct ggccccttg ccccagccc ctccctgacc      3840 tccacgggct tcaggcctca gtccagagtc acctcctcta ggaagccatc ccccagtgca    3900
agtctgggca acattcctcc ttgcctggcc cacctgctca ctctcatgct atggctttct    3960
gtaagcaaac acaaagatag gaacaactct gtccctggca cagagcagat gctctggcaa    4020
tatctcatga gtgaatgaag gcacatgaca aacctccaga cctgtggaga ctgaaggctg    4080
agagccttta tagatgctgt ggggccgagg agtttgccaa ctacagcagg tcatgcccag    4140
aggtttctct ctgggtagca aggtgtgtct cccaccaaag gccattggca tggggcccgc    4200
cctgctgacc cgaggcagtg cacagcagag gccagatgca gtgagaagga gcctctcctt    4260
```

```
ggcctgctgt ctgctgccat gcctgtgggg gcgtggacac aagtgtgtgg catagaaggt    4320
ggtgtggcag gtgagaggtt gggggtgtgt atgtagcagg tgtctgtgtg tgtatgtgca    4380
tgtgggggtg tgtgtgcatg catgtgtgtg tgtgcatatg cacgtgtgtg catatgcatg    4440
tgtgtgcatg gagagagaag acctcctctt tctggcccct ctcctagctg ccccctccc     4500 tcctgctgcc aacacactgt caaccccttca ctgtctttttt ccttgggact cgttgatctg   4560
tctctaccat cccaggtgtc tggagcagcc tctaaccttc catctgccaa ggtacttcag    4620
ccccacccct cccagctgtg aatgtcccc taggatgtgc cactgacaca aagagccaca     4680
cagctccaaa atagaatatt atctaaccca ctgctcccctt tgctgtcagc aacacctcca   4740
ccatgcttct cccaggaccc cccttgaact ctctgcttcc tccctgaggc caaaggaaag    4800
acaggaaagg ggccaccttc ctgtccttgg gtcccacaga gatgtatcct tgtaatgaaa    4860
cctactttat gcttgagttg tatccagtta gtttctgtgg cttgcaatca agacccacac    4920
ccacctcaac ccaggctcta gagagtagac ccttgttttt gcctggcttg ggtcgacctg    4980
gcacctgcca gggtcccagc ctctgagtca gcccaccttg ccctcatcgg tgccacctcc    5040
aggcggctgt acatagactc tggcttctgc cctggcctgg cctctgggaa ctgcagctgt    5100
ctgcttccat cctatgtgga tggtgcctga aagtgaatag ggatcagtta ccagcccagt    5160
atctgtcccc ttctcaatag cactgattcc tatggggaac tgcttttctt ggactatgta    5220
tgggtttggt gggagggtag ttcctgtaac caaccctaca gggtgtagga acctagactc    5280
tcagcaacat aacaggcagc aggctcccaa gctaagtctg gccagctggg ccacctctcc    5340
cagattctgt ttcatgagag catcatccaa gagcagtggg aacactgggg acggtccagc    5400
ctaggactgg tatgcagatc agagaatccc agatagaagg tgattgctgt tcttccagtt    5460
tcttggccct ccagagcaac catacttccc atctgcccca aaacctgatc ctccaaactc    5520
ccaccatttc tgtgcatccc caatatctaa tagatcaact gcctttcatt tacatttgtc    5580
acaaccaaat gatacacctg cccttcaccc actactgaac tgcagctggg ttagtccaaa    5640
ttcagggccc acgtgtcatt tcaagcctgt cttgaataat gtacaccttc ctgcaatgtg    5700
aggatggcca ccaccttggt cttatacca cgggtgtcct gagctacatt tctcataatc     5760
aaaaataaac tcaacacatc actccagcct gagcaacaga gcaagacact agctctaaaa    5820
ataaaaaata aaacaaaca aatgaaaaac ccagcaaact tggggaaaga ggaagcacct    5880
gatttccaga gtttccacat catgagatgc aaatgtccag ttttcaacaa caacaacaac    5940
aacaaaaaaa aaatcacaag gcatacaaag aaataggaga ctaagaccca ctcaaaggaa    6000
aagaataaat aagcagaagc cataccagag gaaaaccaga tggctgactt actagacaaa    6060
tactttaaaa caactgtctt aaagatgctt gaagagctaa aggaaaatgt gaacaaagtc    6120
aagaaagtga tggaacaaat ggaaattcca ataaagtgat agaaaacttt ttggagtttt    6180
ttttcttggt agcaaaaaat tatgaagctg aagaatacaa taaattccct agagggcttc    6240
aaaggcagat gtaagcaaac ttggccaggt gcagtggctc atgctcataa tccagcactt    6300
tggaaggctg aggcaggagg attgcttgag cccaggagtt tgaaccagc ctgggcaaca    6360 tagaaaaacc ctatctttaa aaaaactat ataaaattta aaattataa atttatttta     6420 aaaaatcagc aatttgaaga ctggacaggg aaattatcaa atttgaggaa cagaaaggaa    6480
aaagatggaa gaaaaataaa cagagcctaa gagacctgcg ggacaccatc aagcagacta    6540
atacccattg tggaaattcc agaaagaaaa gagagtgaag gaccagagag attattagga    6600
gaaataatgg ctgaaaatgt ctcaaatttg atgaatgaca tgaatatgaa cattcaaaaa    6660
```

| | |
|---|---|
| tctcgacaaa ctccaagtag gaaaaactca aagatactca tactgagatt catcataatc | 6720 |
| aaactgctga aagccaaaga caaggagaca atatcaaaag ctgcaagaga gaagtgactc | 6780 |
| atcacataca agggatcttc aaaaagatta tcagatatct tggctgggca cggtggctca | 6840 |
| cacctgtaat cttagcactt tgggaggccg aggcaggtgg atcacttgag gtcaggagtt | 6900 |
| tgagaccagc ctggccaaca tggcaaaaac ccatctccat taaaaataca aagattggtg | 6960 |
| aggcatggtg gtgcatgcct gtaatcccag ctactcggga ggctgaagca ggagaatcac | 7020 |
| ttgaacctgg gaggcggagg gtgcaccaag ccaagatcgt gccaccactg cactccagcc | 7080 |
| tgggtgacag agtgtgacct tgtttcaaaa aaaaagaaaa aagaaaaaga aaaaaaagat | 7140 |
| catcagctat ctcatcagaa acctcagagg ccaaaaggca gtagattgat atattcaaag | 7200 |
| tgctaaaaga aaaaaataaa tctgtcagct gagaatcctg tatctgtatc tcacttaacc | 7260 |
| attattttaa aataagggaa aatgaagaca ttcccagata aacacaagct gagggagttc | 7320 |
| attatcacta gatctgccct gcaaagaaag ccaaagaaag cctttcagga tgaaatgaaa | 7380 |
| ggatactaga cagtgactca aagctgaata aagaggccag gcatagtggc tcacacctgt | 7440 |
| aatctcagca ctttgggagg ctgagatggg cggatcacct gaggagttgg agaccagcct | 7500 |
| ggctaatatg gtggaacccc atctctacga aaaatacaaa aattagccag gtgtggtggc | 7560 |
| acatgcctgt aatcccagct acttgggagg ctgaggcaag agaatcacct gaacccagga | 7620 |
| ggcggaggtt gcagtgagcc gagattgtgc caccgcactc cagcctgggt gacagagtga | 7680 |
| taccctgtct caaaaaaaaa agccgaataa acgaataaag atctcatcta tggccgtacc | 7740 |
| accctgaatg tgtccaatct cagaagctaa gcagagttgg gcctggttag tacttggagg | 7800 |
| ggagaaataa cggtctatgc taaaggaaaa ttcaggtgca attaaagtaa aattaattat | 7860 |
| ataaagaga atacattaaa agctagtatt attgtaactt tggtttgtaa ttccaccaag | 7920 |
| tggaatttgt tcctgaaatg ctagaatggt tcaacataaa aatcaataaa tgtaatagac | 7980 |
| cacattaaca gaaaaaaaac ccacacggtc atctcaattg atgtcaaaaa agtatttgac | 8040 |
| aaaattcaac actcttttga agaagaaaa agctcaacaa actaagaata ggaggaaact | 8100 |
| acctcaaata ataaaatcca taggccaaat ccccaaactc acagctagca acatatttaa | 8160 |
| tgctaaagac tgaaagcttc ccctttaaga tccggaataa gacaaagatg cccactttca | 8220 |
| ccacttctac tcaacatagt atgggaagtt ctagccagag taatcaggta agaaaaaaga | 8280 |
| aataaaaagc atctgaattg gaaaggaaaa agtaaaatta tttgtttgcc caatacatgt | 8340 |
| acaatgtttc aggtgaaggc tcagaacagt acaaccttac cagcaagagt cctgctgtct | 8400 |
| ctgtgtgaat cccagctatt actcactagc tacatgatct ctcttgccct ccctgcctca | 8460 |
| atttcctcat gtgtaaagtg ggagaaaaat aatagttcat gcttcaaagg tttttttgttt | 8520 |
| gtttgcttgc tttgagacag cgtctggctc tgtcgctcag gctgaagtgc agtggtgcaa | 8580 |
| tcttaggtca ctgcaacctc agcctcctgg gcttaagcga tcctcccacc tcggcctccc | 8640 |
| aaagtgttgg gatacaggcg tgaaccactg tgtctgaccc aaaggattat ttgaggagca | 8700 |
| gatgaattaa tgtgtcataa cctcaaagca gttgcaaagg cgtttaataa ttaaaatatc | 8760 |
| acattttaaa ttaaaatata aggctgggcg tggtggctca tgcctgtaat cccagcactt | 8820 |
| tgggaggctg aggtgggagg atcacttgag cccaggagtt ccacactagc ctgggcacca | 8880 |
| ttgggagacc ctgtctctac acacacacgc acacacacac acacacacac aaacttaaag | 8940 |
| tagccaggcg tggtgctgcg cgcctgttgt cccagctact cgggaggctg aggcgggaga | 9000 |

| | |
|---|---|
| atcactggag cctgggagtt cgaggctgca gtgagccgag atcgcaccac tgcactccag | 9060 |
| cctgggccac agagcaagac gctgcctcaa acaaacaaac aaaaacaaaa attaaaatat | 9120 |
| taagtaataa ttaacgagtg ttaatatcca ctcgttgtgg agacaagacc tggacttagg | 9180 |
| aaacaggccc agggaagtag cagaacagta gcgctagagg acgcctggga gaatcagcgc | 9240 |
| gcggcgggaa gagcccggga agcttagtgg ggaagcgtct cttgatgggg tgaggaattc | 9300 |
| tataaattag tggagatgga aaaaaaaaaa aaaagtatt cccaaagtgg gagacagcac | 9360 |
| tcagaaagac gtggtggtaa aacgagtat gagtaacggg gacaacgagg acactggaga | 9420 |
| ttggggagtg ttgggctgga agctggtgtg cagctgtggg caagctaggg aggaccccga | 9480 |
| aaccgccaat gcgtttcccg gacgcagacg ctggcaggac gggaggaacc ccgagacccc | 9540 |
| gcgccatccc ttcaggaaga gttacttctc cccggccaag ttagtgggcc ttgggccttc | 9600 |
| tttctgttgg gatcctcctc gcgtgtcgcc atcgctacaa gtgggcagct ctgcggggaa | 9660 |
| agctgggacg ctgggggctt caccaaggag gctggcggcc gaccactggg aggtctggcg | 9720 |
| gggtgacgac cactgggagg tttgggcagg gcctgacggg gtgacgcggt cagcccactg | 9780 |
| gaggccgaca ccccccgtca gcccaacccc tgcacgcgcg gccgccaacc aaagacccgc | 9840 |
| ggcgccggcc tgcgagcccc cgcccgcgt tgcccaggaa accgagggtg tggctccgcg | 9900 |
| ttctctgggc gtcccaggga ctgggcgcac agtggtcggc gggatgaggc gcctggtgac | 9960 |
| ggacggggcg aggagggcag cgattggtga gattaggcga tgggcgggga agccgcgcgg | 10020 |
| ggattagcga gttgcggcga tgggcggggc aggcgcgcgg ggattggcgg gatgcggcgc | 10080 |
| gccgcgcgtt gagtggggtc cagggaaacg gggtcagctg ggggtggcag ttccaggccg | 10140 |
| cgaggccggg ctcctgggtc ggtgggctgg tgtcttggcg gacgtcccgc agctgccgcg | 10200 |
| tggatccgag ccggggcacc cgccgtgact gggacagccc ccaggcgct ctcggcccca | 10260 |
| tcccgagtag cgcggcctgg ctgctgccgc catcaagcac gttcgagcca aaagctccta | 10320 |
| acgagtcact cgttagacac gtgtgcggag cctgtgtccc aggccagtgc tgtcccgtgg | 10380 |
| agatagattg caagccgcta gggaattttt taactttcta gtaggtgtac gaaaaaagta | 10440 |
| aaacgaaaca aatcaattgg agtaaatcca taaatatatt caaactatta tttcaattgt | 10500 |
| atgtgaaaaa attattggga tattctttgt actattctta gaaatccatt gtgtgtccaa | 10560 |
| cccaaacatc acagttggac tcaccacatc tcctgtactt cgtagcccta ggtggctagt | 10620 |
| ggcataagac acaaaaatct cagctctcct ggagcttatg gtctagttgg agcaggcaga | 10680 |
| caatacattt aaaatataca gtttgttaga aggtaaatgt tgtaaacaac aataacagtt | 10740 |
| gaagtactgg ggagagttgc agttgtaaat cagatgggca gggcacaagg taacatttga | 10800 |
| gtaaagatgt aagaacttga aggagatggg caagtgagct ctataagtat acggagaggg | 10860 |
| ggcaagcaag agttcagagg cccttgctg tggggaggga tccaaggtgg aggagtggga | 10920 |
| accaggaggg gagaggacca gtggagcaga tctcataggc agttgtaagg acttggggcc | 10980 |
| ttattcaatg aaatgaggac actttggaga gttttgaaca gagcagtgac tgatttatgt | 11040 |
| tttggttttg gtttagttct attattattt aataataggc ttattatttc acagaagttt | 11100 |
| tatttaataa ggcagacctc ttgtctggaa atgagacagg tgccggagag ctggatgag | 11160 |
| gcagatcggg aattccattt ggggcaaact gaacttgatt gagaccctgg tagttgtcca | 11220 |
| gatggaacag gacacctgag tctagggttc gggaagaact ccagatggga caaacactcc | 11280 |
| tagctttcct tttctctttt tggatgaccg ctacagggtg agacatcggt atccaggcac | 11340 |
| gataaatttc caagtggaca caatgtctgg tgtcaactac agctgttctc cttcttttcc | 11400 |

```
cagtatcctt tgggtgcagt gagacaccag gagagctgct gctttggggg atggacaggg    11460
gcagcaggaa tgcctttgtg ttttcgcagt gaacctcctt ggcctgggcg aagctgtgtg    11520
gaccaagcaa gtcaggagtg tggccatgtt ttctgagcag gctgcccaga gggcccacac    11580
tctactgtcc ccaccatcag ccaacaatgc caccttgcc cgggtgccag tggcaaccta     11640
caccaactcc tcacaaccct tccggctagg agagcgcagc tttagccggc agtatgccca    11700
catttatgcc acccgcctca tccaaatgag acccttcctg gagaaccggg cccagcagca    11760
ctggggtaag tgagagtttg ggaaggtgct tcccccacag catccctgaa cttagaagtg    11820
ttctgcaaga gaatgggaac agtttatcta attgatccca cttcctgtta ccttgggaaa    11880
attaacctct ttttccctca gtttcttctt aagatagtaa caaggattaa attaagtaat    11940
ttgtgggttt ggagttagtt ttagttcaga ggctggttgg agatgaggac ttagttctgg    12000
cggtgatggc gattacttca ctggcagagg aaaatggttt tcctatcttc agtgcagatt    12060
attcaggtat ttgcctgtgc tgtagccaga gagcccctca gtgtggcaag cctggcgcca    12120
ggcaccagga gccaagactg gtgaggatgc actctctggt ctcgagggga cccctctgt    12180 tcactcatgt ctgtttgcct ctcctcctgg cccccatatt tgctggccat gaattttcct    12240
gtcccttggg ccctctgtct ttcctaataa agtggcctgc ccaacacaac ccttgttctt    12300
tgcccccatt tcttccctgg tgatctctcc tgcagttgga ttactcttgg tggtgaagca    12360
gggaccccca tctccccctt tgagtttatt tgagttttag gtgctgctgc attccccat    12420 tcctaccact tacataagag tggctttcca ggtaattttc aaatccatct cctattatat    12480
ttttaaactg aggatttagt aggtgagacc aggtcttact cattttact gtccttggca     12540 ccaggcaaaa tggatctcag ccctagttgc acattggaat ccctggga gctttgagaa      12600 gcccatctca tcccatgcca agccaagatc aattctcgtt ataggcaggc aggagaaccc    12660
tgggcctaga aatctagcta gaacctcaaa ttcattaggg atatgtatta gtccatttc     12720 acattgctat aaaaaactac ctgagatagg gtaatttata aagaaaagag gtttaattga    12780
ctcacagttc ctccatggctg gggaggcctc aggaaactta acaatcatgg cagaaggtga   12840
agggaaagca aggctctttt acatgatagc aggagagaga gagcaagggg aactgccaac    12900 cattttaaa ccatcagatc gcatgatggc ttgatctcac tcaccatcac aagaacagca    12960
tgggggaaat ccacccccac aatccagtca cctcccacca ggtccctccg tcaacaccgt    13020
gtggattata attccagatg agatgtgggt ggggacacag agccaaatca tatcaggatg    13080
ttttctgttt tgtttacctg agacaaagtg ctgttcacct ctcctctccc acataatcag    13140
gggctccctc ctgcggctcc ggtagctttt cctcactttc ctttcagccc tcgggacacc    13200
ttccttggct ccttttcagag ctcagttact acttgggccc aatgtcaatg ccaccttcta   13260
gattctttcc ggcagcacct cctctggtcg cacatttctc ttccagttat tggagctgtc    13320
aaaaaagctc cccagtgatg gacgatacg atttcactgt gctcacagac tggtcaggaa     13380
accaaacagc tgccacagtg aatgtgttga tagcagcggg gcagcagtag cactcgctca    13440
caggcctggt ggttggtgct ggccccacc ctgaatacct acatgtggct tctccatgtg     13500
gcctgtgcat cctcactgaa gctcagcctg tctctccaaa ttggtctttc cactcacctg    13560
ttccccaaac ctgcccagac cttcctgctg taggcttttc ccttcacttg gcacactctt    13620
tcccttgtct tccatggcc ccatctaagc cccactgtca gctgaagtgt tatattcttt     13680 gagggccac ctgaagccac cttgcaatga gggcctccgt tttctacctc agctcaccat     13740
```

```
ttgttcacag cacttgtcac tgtggcgagt tacttgtcta tggcctgttg tcgttctcct   13800
gcctagaccc agtgggctga gtgggggcaa gtgttggctt ttatgtccag ttttgatctt   13860
ggtgccagca cattgcctgg gtggaagcat gtcctactat cggttacagg gatgtcattc   13920
tgcccagtgc tcaggggcat acacttggat cccagttgtg tgcccttgga cacattgctt   13980
aacctctctg tgcatcagtt gggtgataat atctactcct ggcacatttt cagcgttggc   14040
tgagttacat gtacagtgct taggccacct gggggagagt aagagtggga tacgtgagga   14100
tgtggagtct gttgcatttc tgtctgctgc tggcatcctt cttgtcttgt tttgagttgc   14160
tcgcctctgt ctgctcccta gggcgtagat ttgaggaata ttcctggttc ttcccaggca   14220
gcagggctc aggctgtgct ggagtcagct aggctaaggg gctggtctgg catccgcgtt   14280
gtcctgtcac ctccttggtg ttttctccag gcctggatct gtgctgtgtg ggcacctgta   14340
ttcctccctc ctgccctcac tgattctcca tacctttctt ctcgagagtg ccaagcccct   14400
cccatgtgtt cttgttcata cctaggatcc cgggaagggg ctgggaagga cggtgcccag   14460
gtgccctggg taaacaaagc cacctgactc cacgggaatg gaatgggtgg aggggatctg   14520
aggtctgcat tttgagtatc tctggtctca gaggatgaag catttggtgg gggttggggg   14580
tgggggtag ggtggaagaa tctaaagtct taaaagaaaa tggcagttat ttgtgggaca   14640
gggctgtgtt gagacttggc atgcttcttt ttaagagtca gtgttgtaat ttaggtataa   14700
gtgaagcagt actttgtatt agtttcctgt aggcgctgta acaaagcacc acaaactggt   14760
tgacttaaaa caacagacat ggccgggcac ggtggctcac gactgtaatc ccagcacttt   14820
gggaggccga ggcgggcaga tcacaaggtc aagagattga gaccatcctg gctaacacgg   14880
tgaaaccctg tctctactaa aaatacaaaa aaaaaaaat tagctgggcg tggtggcaca   14940
cgcctgtagt cccagctact cgggaggctg aggcaggaga atggcgtgaa cccgggaggc   15000
ggagcttgca gtgagctgag atcgcgccac tgcactccag cctggatgac agcgagactc   15060
cgcctcaaaa caaaaacaaa aacagaaaca acaataacag aaaaacacag acatttactc   15120
tctggcagtt ctgaggcca aagttgaaa tccagatgtc agcaggattg ctccttctg   15180
aaggcccgag ggagggtcc ttcctggcct cctcccctggt gttcctgggc ttgtggccgc   15240
atcactccgc tctgcccgtc ttcacactcc ctcttgtctg tgtgtctgtc tctctgttct   15300
catgaggaca cttggcatcc agggcccaac cacacccaga gtccctggtc tcctgtggct   15360
gactcacttt ttactgtcac cgtgaagtcc agggggtcct tgtacttgat gttctctcct   15420
ggcaaggcca gggccctgtg attggcctct catggagtgc tgggcagggc ctccatggcc   15480
tctgtcgggc ggggggcta cttcatctct gagtctgtac ccctcgtgtc ccaggcagtg   15540
gagtgggagt gaagaagctg tgtgaactgc agcctgagga gaagtgctgt gtggtgggca   15600
ctctgttcaa ggccatgccg ctgcagccct ccatcctgcg ggaggtcagc gaggaggtga   15660
ggcagggtgc tacacagtgg ggccgccagg cagacctggc ctcccactag aacacctccc   15720
tggaggtggg gttgtgggga agcaggttca gagacaatgg actccagagg ggtggggct   15780
gcggtgccag ctcactaaca ccagagcttt ggtgggctct ggccccaaga ttatacctcc   15840
tgtctctgca ttccagcaca acctgctccc ccagcctcct cggagtaaat acatacccc   15900
agatgacgag ctggtcttgg aagatgaact gcagcgtatc aaactaaaag gcaccattga   15960
cgtgtcaaag ctggttacgg gtagggagcc caatgagagg atgtgggtga tgcaggtgaa   16020
gagcccagcg gtggtgtgtt agggatggtg tgagtgggga gcctgggggg agtgggggg   16080
tgtggcctgg gcacacgtgt gttcttgagg aggtaggtga ggctccaggc ggtcggaggc   16140
```

```
catcagattg ggtgagacct ggctgggaga tgggtctccc cacctccatc caagggcagt    16200
gactccagga agcaggcatg catcctggag tcctaggtga gaattcacca atgtggttgt    16260
ggagaactgg cttgttttgc ccgttggggt gactggaagg agtggtagca cctgggctc     16320 cctgctcagg cctgatgcca ctgctcccca gggactgtcc tggctgtgtt tggctccgtg    16380
agagacgacg ggaagtttct ggtggaggac tattgctttg ctgaccttgc tccccagaag    16440
cccgcacccc cacttgacac agataggtga gcagcagttc tcgggagctg aaccagctc     16500 atggtcagtg gaatctttga gttgcaccta ggaggggctg cctcccttct cggcaccctg    16560
gaggacccca ccttctcccg caggtttgtg ctactggtgt ccggcctggg cctgggtggc    16620
ggtggaggcg agagcctgct gggcacccag ctgctggtgg atgtggtgac ggggcagctt    16680
ggggacgaag gggagcagtg cagcgccgcc cacgtctccc gggttatcct cgctggcaac    16740
ctcctcagcc acagcaccca gagcagggat tctatcaata aggtatggag cccacctggc    16800
tgcattcagc cccagcccag gagcctgcaa gcctgtaaga ccctccttcc cagggcgag    16860 tagggtaccc tgtgaggtct cgcaggtcgg tgggaagcgc cctgcagtga ctctggggcc    16920
tcctgcaatg gggctcctca tgcccaggcc ctcgctgagg atggtgggag gcttgaaggg    16980
agtgagggtc tatgggacaa caactgcatc ttccagctgg tggggctcta ctctcctctg    17040
agcctgggac tcgcctgggc ctgatggcct tctgggcttc tattccaggc caaatacctc    17100
accaagaaaa cccaggcagc cagcgtggag gctgttaaga tgctggatga gatcctcctg    17160
cagctgagcg tgagcgagct gggggctgga ggggtgatgg ggattgcagt cttcaaagct    17220
gccactgggc aacagaaggc aggcaggagg gcaggggag tggccggagt tggtgtaggg     17280
ggctccttcg gggccctgtg agctctccct gccctgtgcc ttccaggcct cagtgccgt     17340 ggacgtgatg ccaggcgagt ttgatcccac caattacacg ctcccccagc agcccctcca    17400 ccctgcatg ttcccgctgg ccactgccta ctccacgctc cagctggtca ccaaccccta     17460
ccaggccacc attgatggag tcaggtagct ggcacagcca cacttcagtc tgacccagcc    17520
ttttgcctca ggaggcacaa agaagggagg ggagggaggg cccaggaagg tggcagggct    17580
gcagaggccc acctagcatc tgttccttct ctctggggca tccccacaag agcgccagat    17640
gagctctggg ctgaccacta tgggtggcac ccaaagccaa gagtcagctg agctttgcct    17700
tgcagatttt tggggacatc aggacagaac gtgagtgaca ttttccgata cagcagcatg    17760
gaggatcact tggagatcct ggagtggacc ctgcgggtcc gtcacatcag ccccacagcc    17820
ccggacactc taggtaacag gctcagccat acagggtggg agcagagggc caggaggcct    17880
ggcaggaccc tgaagtgcac agggtccccc tgtgggtttg cacttgccag cattgctgag    17940
aactgtctga ggagaagttc agaggcttgg cacctgctct ggaagctact ctggaatctt    18000
aattctaagg ccaatggctg cccaccccaa cgggcagcaa cagcagggcc aaggtcttgt    18060
gacaatgtct ggaggtgccc ctattgtcac actgggggtc tcctactggc ctgcaatggg    18120 aggagggct gcagcccac atcctgtgca gagtgctagt gctgaggcgg aaccctcctc      18180
agagctgccc cttctcctct aggttgttac cccttctaca aaactgaccc gttcatcttc    18240
ccagagtgcc cgcatgtcta cttttgtggc aacacccccca gctttggctc caaaatcatc   18300
cgaggtaatt tttgtcttct ggggccag gctgatttgc tgatttgctc tcacctgggg      18360
acaaggttca cagagaagaa aacctgcatt gtggagtccc cctggccctt gtgggatgga    18420
cagctgaggt cttctgcaca gctgccattt cactgtggga gccaagctgc ctcgccagct    18480
```

```
gggcagggac tggaacggct cccagcctgt gtgcctctca aggctaatct ctggtctcct    18540
attgtcactg ccccactgtg tgccaatggg gactcctgtt tatttctggc agcttctctt    18600
tgaggcagga cttacttgga acctacagtg ggtcctatgt gacttctttg caggtcctga    18660
ggaccagaca gtgctgttgg tgactgtccc tgacttcagt gccacgcaga ccgcctgcct    18720
tgtgaacctg cgcagcctgg cctgccagcc catcagcttc tcgggcttcg gggcagagga    18780
cgatgacctg ggaggcctgg ggctgggccc ctgactcaaa aaagtggttt tgaccagaga    18840
ggcccagatg gaggctgttc attccctgca gtgtcggcat tgtaaataaa gcctggcact    18900
tgctgatgcg agccttgagc cctgggcact ctggctatgg gactcctgca ggggtgccca    18960
cagtgaccat agcccatgca cccaccagcc ggtctccct                           18999

<210> SEQ ID NO 8
<211> LENGTH: 16161
<212> TYPE: DNA
<213> ORGANISM: Homo sapiens

<400> SEQUENCE: 8
cagcagggcc aaggtcttgt gacaatgtct ggaggtgccc ctattgtcac actgggggtc      60
tcctactggc ctgcaatggg aggaggggct gcagccccac atcctgtgca gagtgctagt     120
gctgaggcgg aaccctcctc agagctgccc cttctcctcc aggttgttac cccttctaca     180
aaactgaccc gttcatcttc ccagagtgcc cgcatgtcta cttttgtggc aacaccccca     240
gctttggctc caaaatcatc cgaggtaatt tttgtcttct gggggcccag gctgatttgc     300
tgatttgctc tcacctgggg acaaggttca cagagaagaa acctgcatt gtggagtccc      360 cctggccctt gtgggatgga cagctgaggt cttctgcaca gctgccattt cactgtggga     420
gccaagctgc ctcgccagct gggcagggac tggaacggct cccagcctgt gtgcctctca     480
aggctaatct ctggtctcct attgtcactg ccccactgtg tgccaatggg gactcctgtt     540
tatttctggc agcttctctt tgaggcagga cttacttgga acctacagtg ggtcctatgt     600
gacttctttg caggtcctga ggaccagaca gtgctgttgg tgactgtccc tgacttcagt     660
gccacgcaga ccgcctgcct tgtgaacctg cgcagcctgg cctgccagcc catcagcttc     720
tcgggcttcg gggcagagga cgatgacctg ggaggcctgg ggctgggccc ctgactcaaa     780
aaagtggttt tgaccagaga ggcccagatg gaggctgttc attccctgca gtgtcggcat     840
tgtaaataaa gcctgagcac ttgctgatgc gagccttgag ccctgggcac tctggctatg     900
ggactcctgc aggggtgccc acagtgacca tagcccatgc acccaccagc cggtctccct     960 cctcccatc cctgacacct cagaatgtga gcagtccgtg ccatgagctt gttttattgg    1020
agtgaccttg gctccctccc tctgccccta ctccaacact gcagcaaccc catctcttac    1080
gagactggca ggtggagcag gagcctctac acagcctctg gctcttaggt cccagtcatg    1140
tttgcacccc ctcaaagggg caggaccagc ccttcctttc agtgtccata ccaggggcct    1200
tccatgtgct gatgggtgat gtgactgtgg tcagcaggct tgggaagtgc tgctgctgta    1260
gcttgagttg gctgggggtc ttggtaggac gctgatctca gaagtcccca agttcactg     1320 tgtaggtctc tactgttgtg aaggggaatg cctggccagt ggctatctcc tcctcttcct    1380
cctcctcctc ctcttcctca aactcgggtt ccagctgggt ctcgaactca ggctccaact    1440
gggtctcaaa ctcgggctcc accttggtcc caaactcggg ctccacctcg gtcccaaact    1500
ctgtcaccac ctctgtgtag gtctcagtct ccgactcctc ccagccagcg gtggttggcg    1560
gtatgaggcc ccagggctct atggtagtgc tcagggtggt ggcagggca ggggcagcg      1620
```

```
tgggaggcac agtgtggggg cctagggtgg tggtggcgtt gaggcgccgc agccgcatct    1680
gtgcccgaag ccgcaggcgg tgttgtaggc gtcgctgctg caggcgtcgc tgttgggggg    1740
tcatagggcg cgatgggtct atgtgtggga taggccggtt cccgttcatg gccatgatct    1800 cccgatgcg cttccagttg gagcgagcca ggatgaagtt gcactgagtg gccccgatgt    1860
catagtcaac attgcaggtc ttggcgctcg gggtgtagcc ctccgcgtgg gctgtcacgc    1920
ggtactcacc cgggttcaag attcgccagt aatcaccacc actggctgcg gagggagaac    1980
gatccggctg cccagagcg cccctcccag gccccaccc tcccactcag tcctgccccc      2040
agccccgccc tccccctctg agttcccgcc ccagcaccg cctccctct ctgaatttcg      2100 ccccaggct cccagactc tacctgctcg ctgagttcct caagcccca ccctctctgg      2160 cgggtcctcc ctcagaaaga tggggtaaag gtgtgcacac taggtacctg tcttcacgcc    2220
gtgattaatg ccactcacag agatggtggc gttggcaatg gggatgcctt gctcgtccgt    2280
caccaccccc ttaatgccgc ggtgcaccta gggaagcagg tgagggctgc tggtcctcag    2340
gaaggtccaa tgtggtccgc tgctccctcc cgcccatcca ggagcctgtg cagcctcctc    2400
tccccaggca ttgccctagc caccccacct gctccatgaa ggtgagcagc gcctccttgt    2460
tgttctccca ctcgcggggc agctcactct catgagggaa cttgtcacag cccaggtaga    2520
aggagagctc caggcagttg gtatgcaggt aactgaagtc attgatagct ggccggggac    2580
agatacagac ccaaagtcag cccctctccg gaccaggccc cgcccacagc cctcccagg    2640 ctgactcact cccggtccgg gggttccact tggccccgtt gacgatgccc atgccgccgg    2700
tgtagtcctg ggcttggcag cctccgcggt agggctcggt caaggtgagg tgtgcggagg    2760
cgaaggagat ggcaagccac cggaagatgg cgtggtctgg agtctcctgg gcctcggaga    2820
cctcgtcctc atcctccccc cgggctgctg ccatggctgc ggccagcagc tgctcctggg    2880
taggcgtgcg ggccatatcg tagggtagg atactagccg ctcgccgccg ttcagatttg    2940
ctcccagcac gaaggggttc ttctccatcc aggcaatgat ggcccggacc tccgtggata    3000
cctggagtgg ccagcacgtg tgaggccagg gctgcagctc cggccactat ccccaaccta    3060
gcccgatcac cctccatgaa gcttcacacc agtactcgca cgatccctg tccccaacc     3120 cccagagcct cagcgtctgg agttcaggca ccgtcagccc cacccccaag cccagaacac    3180
caggacccca gggtccagct gctcctcct gcctttcag ccaggctgta gcctcaccgt     3240
ggcatctggc gaaaggtagc gttcagggat gggcaagtta ttgttgggga cccggtaggg    3300
gacccatttc ctctcctcag ctccccagag cacagagttg agatccggga aatcttcaaa    3360
gatgtcaaag ccctcctcag tccacagtcc cagcgcccag ttcccaaaact ctgagccctg   3420 tggggagcca gcagggtagg catcggctac ccacaccccc acaaccccca gctgcctgga    3480
ccctggccag cctcacccct caacccacca tctgcgctgc cacctcgtag ccatcagggt    3540
tcagtgaggg caccaggtgg atgcgtgtgt cctgcaccag gctgcgcaca cgtgggttcc    3600
catcgcggta ctctcggcac aggtactgca tgagcagcag caacagctct cggcccagca    3660
cctcgttgcc atggatccca gcagtgtagc ggaactcggg ctcccctgca agggcgggag    3720
cctcagtgag cactcagtct cccgaggccc agggcagctg aggaaggacc cagacccacc    3780
tcatacccga gggtctgggg gacagctggg gctcctaggg ccctgtaaga caagccagaa    3840
tccccagaga ggctccggaa caggcgggag gcagtgagct ctgcacatca gcagcagagg    3900
ccagctgctg gcccccacag accctccccc agttcatgct ccccagggtt gtctgagatc    3960
```

```
tccatggcat agatcttgag gcctcgtgag ctcttgccca ggctgtaagt gcgggtgatg    4020
gtggggcact cctcgttcac caccttcatg agctggcgca gagggggagg acgtggaatc    4080
aatcatgcaa tccgtccccc gctgaccatg ccccttccac ttccagggcc tgctctatgg    4140
cgagggacgg gcatgacccc ttcacgcagc ccccaggtac tggcctcctt cctaaggtga    4200
gggacagcca gcatccctgg aaccagtagg gactgggccc agtgacagaa gcaccaggca    4260
cacactcccg tcagccacag acaggtccca cccccagccc caggatatat gctcccaacc    4320
tggcgcatgt ccttgtagct gtggtgccgg aaatccaggt catcggtggc caccacctca    4380
ttctgtgcgt agtagctgta gacagctgca agggaggcgg ggttgtcttt agctgggtgc    4440
cggctggccc accctagcac cccacctcca ctcagagccc ctgccagccc tccacactca    4500
cgggccacag agcaccccag cacctccagg cgcatgcaca ggctgccatt ccaggtgagt    4560
gggtagatgc ggatgaaacg agccaccacc ggctctggga gctcactcag cacgggtgtg    4620
tccttgtcca cgttcccatg aaaggtctgg ggagaggcag gcctcagagc agtactgcca    4680
gcccctctga gagcccaccc ctcgcccaga caatgggagc agagccaaga gcctgggcat    4740
ggtgcccacc atttcctcat agccgttggt gtacatcacc catgtctggc tgtcattgct    4800
gaagcccacg aagaaggtgg tcacaaaatc gtcactgtgg agtggacagt ggtcagagca    4860
agggtcttcc ccctcccagg ccctcaggtg gcctgagcct ccctcttccg agccccaaga    4920
atttaagagc tagcagggtg gtgctgcacg gcccaggtgt tgagcctggg tcctatgccc    4980
gtcacatagc catgggcagg tgatctgtcc ctaaactcat gtgctatcag gacacagggg    5040
ctgactgacc aggctgagga gtggggatgg gcagggtgag tccctcactg atctttttgg    5100
ccttctttgg ctgggccaaa gaagggccca ctggaatctc cttaatggga cacagagcca    5160
tgcctatgta gccactcccc tctgccaact atccatgagc ctggccacgc actggatgct    5220
ggagtctctg ccctgggtga tgacgcctgt gaaccgggta gtcctcctgg tgtccacctc    5280
tatccactgg gtcctggcat cgtcctcggc acaccacgca ccatcatagt agtcgtcctc    5340
agtggcaccg gtctgtccag ggggcagggg aggctgagca tgggcggagg agtcccttat    5400
cccagttggg agatgggccc atcccaatgc ccacctgcat gttgagccgg ccgcgctgtg    5460
cccccaggcc gtggcgcagc atggaggagg ctcggatctg gttgtcctca atacggtgtg    5520
actccatccc aatgggggga cactctgagg acgcgtaccc cagaatggtg gctcactagc    5580
tccatccttc cctccaccaa acccagaacc aaggagccca gagcccactc ccggcacatc    5640
gggggcacag tcagagggca gctctggtca gctggtggct ccctggtgcc ctgcaccagc    5700
ccacctggaa tcgactcaaa gccaggccag gagctgtttc caatcccagc ctgtgcttcc    5760
cctccctggg cctcagctgc cccatctgga gaacgggctg accatgccca gctctcaggg    5820
gacacacgtg aaatcacagg tagagctccc ccagggcgca gccacagatg tcatccagat    5880
ggggaccgtc tgcacaatgg ccctgcaggg atacctgtga aggtacctga ggtcctcact    5940
ccccaccaag gccccaggtc ctcccccctac cacgcccagc cactagggggc cctggggagc    6000
tgccaccctc ctgaagcagg ccagcctggg gtccagggct ggggcagcca agcgaggcta    6060
tcctgggctc ccggggcccc tcccttctgg gtccaagaa tctgagtagg aaagggttcc    6120
ggggacctgg gtcctgtttg tgacattggg ccagtcactt gtcccagcac cccatcctg    6180
tggcccccac cctcaccccc ttgtgccccc cacttactga cttttctccgt aggcgtccac    6240
tcctcctcca actcctcgcc ctttcggggc tctagggaca atgaagggag acatggcac    6300
caagggcccg ggaggcaatc aggagtccag atgctgcccc acagggaccc aggccccaag    6360
```

```
ccccagccac acacctttgt ggtccttgcc cttctccact gcccacttgt cggtctcctc    6420
cttgggctg  ctgtcctcct  tttgggttt  ctctggaagg tgcaaggtag gaggggccag    6480
tcagcctggc tctgggcttt gaggaccatg tggggtggat caggcaggcc ccaggtggcc    6540
ttcagggcag gcctggtgtg ggaagtcctt ggtcccactc actcagctcc tccttctctt    6600
cgtccgtctg gcgctcagca tcgggcttct ggggcggagg aggcccaaag taatagtcca    6660
ctatggggag ggagagccag ctgaggctgc cctgaccctg ctgcggggcc tcagctcctg    6720
ggtccacagg agctcagcag acaggaccg  cgccagaggg gaggaggacg ggagatgggg    6780
gacagctgag ttgggagagg gtcttgcagg agtcaggagc agcccgagct caggggcagc    6840
tgagcaagac cctgctgaag tcaccagccc ggccttccag gagcatctgg cctggggaaa    6900
ggactcgagg cccagggcat gggaaaggcc tggaggggaca actggcacct gtgcctgggg    6960
ttgcgggctg gggggtgaga tggggagaca ttggaggcac tgatggggac ctggggcag    7020
ggaaatggcg atgcacgggc tgccacccag gaggaaaggg aacctgaggg ctccaggac    7080
gcagggcat  gagcaacagg gaggcaaaag ccctcgggct ccctgaagag agtggggcag    7140
tggccacgag ccagcgggaa gccagttaga gcacaggact gggagggctg gaacccacat    7200
gggtgacagg gcagagtgtg tgcctaggga caccctgtg  ggggtcacag ccaagcagga    7260
accagggaag cggccaagga aagaccagcc tgagggcaga ggagacaggg cagtggctgg    7320
ggtgggcacg cagggacagc agggacagcg aggtaaccac gggcacaggt ggggttgcaa    7380
ggtgggtgag ttgccccagc tggctcctga ccacacccca gccccgaccc ccacctgcct    7440
atgtccctca gactctgggg tgctgggtac tcactgtcat cgtagttggg gatcacgtaa    7500
ccatcaccat agtcaggggg cagcgggggc agcagaggct tcacaggagg ctctggggag    7560
gcggggaggt taggagggg  ccagagcgcc gtggccatgg cacctcctct cctgcccccc    7620
atcctaccaa tcctctcctc cgggctgggg gccgggcct  tctcctcagg gggctctggc    7680
cagacccgct cgggcctcct ccttctgctt gggggtggcc tgggttgctt ctggcgccga    7740
atgtactcaa ctgaggggga ggctggctca gagtggggcc caaggctggg atgggcccat    7800
tggcacatcc cccaggccag gggtccgacc caggtggggc tggcaggacc ctactcaaag    7860
tcctcatagt cctccctctc gatctggtca ttgtagtcca gtgtgggttg ctcggtctcc    7920
tcctccggct ctgaggggaa agcgctggta gctgcctgac aaccccaccc aggcctactc    7980
tggggaagcc ctcagtccaa ccagccaggg cagctggccc caaggccagg cggatgacgg    8040
ccactcacca ggctggtgct cctgtgcctc cacatgggtc tcctctcctg gattctgcca    8100
gttatttgag aggggcgccc ctgcaacaca ggagttccag aagcaggtgg gcgggaggcc    8160
tgctctgacc accttgggag cctcaggcca ccagccaccc atagagccca cacagagcct    8220
gtggacaccc tcctgaggcc gagctcactc caaggaggcc tgagctcctc tggccttcag    8280
catcctgctg gcatctcatg gggccagaga gctgggccca ccttctgggg aacctactgt    8340
gctgctggag gccctaccac aaagctgtcc ccagcgggag aaggcaggag ggaactccat    8400
gggctcagag cccagggaca tctgggcagg ggcctgaggg acagaggtcc cacccaaaag    8460
gctgccaagc cctctcccta cccaaaagag gctacagcac tgagggagcc caccaatcaa    8520
attgtgaaat ttatagcaaa agtgaggttc ccatccagtg gggagctgaa ggtctatagg    8580
aagcagggcc ccagaaacct gcctcccact ccctgcctcc acccgagcag gcagtcagag    8640
ccccatcacc ccagaggagc ccggcacaaa cctccctcct ggggtagctc ctcggggcca    8700
```

```
gggctggggg gtggggcag tggccactcc agggtttctg agggagccag aatgggggc      8760
ctcttccctg acggggcttt cttggtggcc ttgggtggct tctctttggg cttcttggtg    8820
gccttgggtg gctcctcctt gggcttcttg gtggccttag gtggcttctc cttgggcttc    8880
ttggtggcct tgggtggctt ctccttcccc ttcttgggcg gcctggggga ccctccaag     8940
gactccttgg gcaccttggg gcctttgtct ttcttgcctt tcttccctt gtctttggtc     9000
ttttccggag gcactgtcca agatgcagac tcgtgtcaaa tgaacagagc cagctctgtg    9060
cccccatgag gcccctctct agatgcccag aacctgggca cagggactct tgtcagttcc    9120
cagtgcggat cagcaaactg agaggttaag tcatttgccc aagtggcaaa ctgggatccg    9180
gacccagatt ttctgtctgc aagtctgggg ctgtgaccac caatctcaac ctctctaaag    9240
actgagcgta gggttcccag ttccaggggg aggccctca tccccccacc tgccaaaacc     9300
tcaataggg ttccttacta tccactcctc cactattctg ttctgggcac agaaggggca     9360
gagaggtgac tgagccatcc aggcctggag gagcatctgg tcatccctgc caactgccat    9420
acaaaggaag ggacatgggc ccaagacctt cccctggtct cctacggggc aagaaaagct    9480
tcaaagaaaa gggacacttg gttgagtatt gaagcccaaa gaagaggaag tggtctcctt    9540
tcgagaagta agggggtttgg aattgattgg aaggataggg agtcctgggg ggttcaggga   9600
tcacacagag gacagaaaag acaggtaggg agcttgtggc tgcacactca tttcagagtc    9660
tgggagagg agcagggact ggttgtgagg attccccatg ggaatcctcc caggaccct     9720
agcaggagct gcaagtgctg ttgagaacct gatgagaggt ggggagcatg agggaagttt   9780
ggcagaaaca caggaaagct accaaatgca gacagccagg ggacgcaggg ctgctagagc    9840
ggtgccccag agccaggaga gcaagcctgg aaggagagcc agaggcagga ggggcacagg    9900
cagcccaggg tgtgggaagc agccaggaaa gatctagagc tggggtggca ggggaggggc    9960
tgctgacatc aggaatgttg gatggtgcct tggaatctcc tgggagacag ggatcacaag   10020
accctctgcc accttccaga gggccacgat gaaaacagct aagatttact gacaactgat   10080
tatgcaagag gccgtggggtt aaatgcttca gtgatgcatc acctcatcta atttcctgta   10140
ctaatgtagg accacccatt gctcaccacc acctgaagcc ctgtgctcac caccacctga   10200
aactctctca cctacgtgag acctcctgga gtaggagggc aaaggcagga gggagggacg   10260
acgtgaagct gtgccaccaa cagggagagt ggtcccatta gtatggcagg gggtgacaca   10320
gcacagtccc ctgtggctca agcctagtac ctgtcgcgta ctggaggaat ggggataagc   10380
gacccgtaca accacagcac caaccctaga gccaccggcc cccaaaagcg gccctgccgc   10440
ccgggtgctg gatgtgcctc cacgccagcg ctgacctcgg cctagcacag ggtccctcca   10500
ggcatctggg ctcgcgtgcg cattagtaag ccagccattc ctcccctagc agactgggga   10560
gtggccagac cctaccgaat ccccctgttc ccacctgaga tgccagcccc ccacaccccc   10620
gccctgccct gggctcttac cttctgcggc cgtccctggc cgcttccctg gcttgccccc   10680
cgcctgggct tttcggaccc gcggggtggg ctcgggaggc ggcggggcct ccacgtcgtc   10740
ctcccggggc tcaggttcta gctctgacag gaagccctcg aggaactcct cgatctcgtc   10800
gtcggtcagc accgtctgcg ggcgcccctcc agggcacagg gccagcaacg ccaggaggca   10860
gctgagcagg ggcgccccgc gcacggccgc catggccgcg gcacgcgcgg ggggctccgg   10920
ggagggcgcg gggggtcagg ggctctgggt ctctgggaaa gggcggagag gggatcgaga   10980
cgggtgaggg aatccaggaa ggggcgggag agaggatggg gtgagcgagg gaatcccggga  11040
aagggaggga gagtggatta gggtgggcga ggggacccgg gaaggggtgc tggggggctc   11100
```

```
cgaagccaga ggggctcagg ggtggtcggg gcgctccgag gtctggcggc taataggcgc    11160
tccggccccg cgtggcgcac tcccgcgcgg atagccgtct ccaaagcgct ggcgggcccc    11220
ggggcggggg cgccggggct tccggagccg gctccccacc cccggggagg aggaggagga    11280
agagaaggag gagccgagag tggacggagg ggctgcgggg gggcggggg cggggggcgg     11340 ggggctaggg gcggggcagg cgggcgggcg ctggcggcga gcgtcccaag cccggagact    11400
tgcgcctagg acagagggc aggggcggg gcgactggga agacagaggg cctgagggaa      11460
ggaaaggtgg tggggagggc ctggggtgcg ggtctgaggg ggccgacatc cctcctcctt    11520
ctgccctagg caccccccctt aaggcgggac cccgagtcca ccggggctct gagccctccg   11580
cgggtgacca ggaaccctgg acggaaagcc gtggtgtcag gcctctgaga cctctctcaa    11640
ttcggagggc cacagaaagg ccaccccatc cttcccaggc tctggagcct ctgcccatgg    11700
gccctgctgc atcccagcgt caattcattc agtcatccta ccaacctctt caggtcggtg    11760
tggggccggg ccccgtgctg gccccaggg agggacagca cagtgggaac tcactttcca    11820
gccaggaggc aggtgcaaaa ctgccctcag agtggccagc tgccccgctg ggggtaggag    11880
tcccatgtaa gggcatgcca tccctcccct ccgggtccca acgtggacaa atagccattt    11940
atcaccttct tcttaccaga actcattttt taaaaagtgt ctaccatacc tccagctgcc    12000
acatggaccc agagggccca gaggacccag aaggcaggtg gattgagtgt caactgatcc    12060
caggatccat cagggatgtg caccttggtg cctggtgttt gccataaggc ttctccaggg    12120
caaatgttgg ctgccctaca acggccatca acaggcagag tggtcccatt agtatggcag    12180
ggcgtgacac agcacagtcc cccgtgactc aagcctagtc cctgtctcat actggaggaa    12240
tggggagcta aggacagagc tccgaggaca ttccccctta aaggaatgag gacacaagag    12300
aaagctcaca ggtagtccat gggccaagtg cagaggcaga cagccctaag ccacgattgt    12360
ctgcggggtt tggccccagt gaagtagtca ggtaggaag cctaggagcc cctgggatga     12420
ttgacagggc agagtttgga cctggggtca aaaggaaaga ggaaaagtgg gtcaggaagc    12480
acctgggtcc ccagagcagc cccgagtgag ttggagcagg cagcagccgg ggaggccaca    12540
gtggaggctg ctgggcctgg gatacatgcc accccctggg agcaggacca caaggaggcc    12600
ttgcctcctc tcacacctgg tcctgccaag accctgcctt tgctttctca ctgcatctcc    12660
ttgaaaaagc agtgggactg tgtcaggttc tggctctacc tcccaggcac cacatctcgg    12720
caggtagcct cagtgccgtc cacctgtgtc cctgttctcc ttgtcgttca tacaggatca    12780
tgcatgtgct gtgcctagca cacattcttg gcactcacac tgctgccttt tagctctcat    12840
catttgccct cagagatcaa cctgagctgt gcccactggg gcgctcagag cagaccctga    12900
gccccaacac ccaggctccc tgtgcacctg agcctgcctc tgcctgccac gtgccccag    12960 gccagtcctg gtggcagcaa ggatccgcaa gctctcccct ttcctcatcc tctgcaaagc    13020
tctgaatcat ctttctcaaa acttgttctg ggaatttgct ccgttgcccc agttgagcat    13080
gtcaagcccg gcggcccaag gctggggtga agcagcgtgg cacgtcactt ccctgggaac    13140
aactcacaca tggattggat ttgggtccaa catcctctgc cagggaaaat agaagccata    13200
agaaaacaaa aaaggaacag aaggaggctt ttcttcagtc acagcgagtc accaacaaaa    13260
acatgtgcaa aagctctcat ggagagctgg gccacaagga gggccatgat gttggggcc     13320 ctctgacacc aagggtgtgg gcaggtggat gggaggcagc tgcccctccat gccaggctga   13380 tgtgcctccc tttgggtggt ggggctggga ctcccactcc acttgaagac ctgcaccaaa    13440
```

```
aagtccttta gccctgtgcc caggctctgc cacggggccg gtgagggggac ttctcccctc  13500 tgctgccaga gtgaagccag tcaggggat gggaggcttg tagccaagag cacctagtgg  13560
ctttcagggt cccttacccc tgccacttag cagggtctgc acctgcatcc aagtgttctc  13620
ctgggctaca gtgggggct ggtagacact ctggtgatcc actttcagct tcccacatgg  13680
atgtggcagg gactgctttg gcatttccct accccaaggg acagccactg cggcaggact  13740
gggctgggga gggtggggcc tgcgctgggg agggtgcccc ctgtcccttg ctgctgctgg  13800
aatgggaagg agagttgttg agagagccag aactgtccaa gggtggaagc tggcgaaact  13860
gacctgcagg gaacagggag acagggagca tggcccagtg agtaggtcct atgtagctct  13920
gaggccatca accctgccat gagggctgag accccaagag agaagttgag gttgggtcag  13980
gggcctgtta gtgccagctg aggaggggga caggccagcc tcctcccact gggacccaag  14040
ctatagctcc tgagcctcca gagctgcctg gtgcctcaac ctggtcagag gtggaaactc  14100
acctgccagc aggcccagtg tgcctgagtt ctgactgtgg ggatctgcag ggcacagaag  14160
gataagaggt catcagggcc tggggacagg caggagtggc agggtctggg aggctgggag  14220
cagaccctcc caacctgccc catggcctcc gtggccccca ggaccccccat ggcagcagct  14280 cagacacggg ttgtgcctca gaaggaagtg aagctgtgtg taccgagatg gcccagcaaa  14340 cccttttgtat gtaaacttcc gccacagccc agctgtccag caccagcatg tgtatctggg  14400 ggaggggat aaatagaagg tctgggaggc ctggatctg gccagcaggc tactgggatc  14460
acagatgcca gcccctccat atctccgctt gagtcctgga tctgcctcct gggaccaaag  14520
gggaaaggac caggctaggc tccttcctttt tgttcttcc ctcttggggg aggctcctag  14580
aaactccccc ttctctgccg cccaagtgcc tggatattac cagtgggggtt agcctgtttg  14640 ggcccacaag atgggatggc tcccagagcc atgggacctg aggtctccca gacagtgtct  14700
agccaccctc acaactggca gaacaatttc cttggttttc aacaacttga aaaacatatg  14760
tgattttcca cagtccggtg cttctcaggc ctggctgctg agtgagcaga gttcatgctg  14820
aattccttcc actcaccaca gggcagacag caagcccagc tgtggggact cggttggggt  14880
gggggtcacc acagcaaggc gcgggggagtg gggaggggg caggcttcca gcactgatga  14940
gtaattctgc tgcccgaaga tctgggaaga gggcatgtga caacttagtg caacaatctg  15000
cccagtgtta ggtcagaagg aaggagaggt cgttcaaaat ggagtctggt ggaaaaaata  15060
atgtttggcc ccacctcata cctccctcaa aattaactcc agattaatga ggtagatgtt  15120
agaagaggaa ccaggaagg actacaagaa aatatggagt cttttatttac attgtgaggt  15180 tttcttttagg ttttgtttgt ttttgttttt gatatggagt ctcactctgt cacccaggct  15240
ggagtgcagt ggtgcgatcc cggctaactg caacctccgc ctcccaggtt caagagattc  15300
tcctgcctca gcctcccaag tatctgggga ttacaggcac atgccaccat gcccggcttt  15360
tttttttttt tttttttttt gtattttag tagagatggg gttttcaccat gttgaccagg  15420 cagatctcaa actcctgacc tcaagtgatc cacccgcctc agcctcccaa agtgctgggc  15480
gcccggcatg tgtgcccagc ctatattgac attcttgatg gagaagtctc ttaaggaagg  15540
acagagaagt ttggttgcat aaaagttttt accttctgta catcaaaata tactgaaaat  15600 gaaataaag agcaaacaaa atactgagaa agaatgcagt gcttagagag cgaacattcc  15660
tggcctcctg tagttttagg aagcagctgt ggcctcagac ccatctgctg tgaacctcta  15720
ctccatattt attgcacttt ctgtctgtga gcgtcggttt ctctcctcta taacaatagg  15780
ataataatga cactaccatg ccttgcaaaa atgctacaag ggttcactga gataaatctg  15840
```

```
gagagtcatg cctgaaaaat agtaagtcgt tgataaaggg aagctgctat taataaataa    15900
agctttttct ttttttttt  tttgagatgg aatctcactc tggcgcctag gctggagtgc    15960
agtgatgcaa tcttggctca ctgcaacctc cgcctcctgt gttcaagcaa tcctcctact    16020
tcagcatcct cagtagctgg gactacaggt gcgcaccacc atgcccggct agttttttac    16080
atttttaaag ctattaatag gccagccaca gtggctcatg cctataatcc cagcactttg    16140
ggaagctgag gcaggtggat c                                              16161
```